United States Patent
Ohtomo et al.

(10) Patent No.: US 11,376,326 B2
(45) Date of Patent: Jul. 5, 2022

(54) GPC3-TARGETING THERAPEUTIC AGENT WHICH IS ADMINISTERED TO PATIENT FOR WHOM THE GPC3-TARGETING THERAPEUTIC AGENT IS EFFECTIVE

(71) Applicant: CHUGAI SEIYAKU KABUSHIKI KAISHA, Tokyo (JP)

(72) Inventors: Toshihiko Ohtomo, Tokyo (JP); Takayoshi Tanaka, Tokyo (JP); Yasuo Sugitani, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 209 days.

(21) Appl. No.: 15/741,219

(22) PCT Filed: Jun. 30, 2016

(86) PCT No.: PCT/JP2016/069493
§ 371 (c)(1),
(2) Date: Dec. 29, 2017

(87) PCT Pub. No.: WO2017/002934
PCT Pub. Date: Jan. 5, 2017

(65) Prior Publication Data
US 2018/0169237 A1    Jun. 21, 2018

(30) Foreign Application Priority Data
Jul. 1, 2015    (JP) .............................. JP2015-133076

(51) Int. Cl.
*G01N 31/00*    (2006.01)
*G01N 33/53*    (2006.01)
*A61K 39/395*    (2006.01)
*A61K 45/06*    (2006.01)
*C12Q 1/02*    (2006.01)
*G01N 33/68*    (2006.01)
*G01N 33/574*    (2006.01)
*A61K 31/44*    (2006.01)
*A61K 45/00*    (2006.01)
*A61P 35/00*    (2006.01)
*C07K 16/46*    (2006.01)
*C07K 16/18*    (2006.01)
*A61K 39/00*    (2006.01)

(52) U.S. Cl.
CPC ........ *A61K 39/39558* (2013.01); *A61K 31/44* (2013.01); *A61K 39/395* (2013.01); *A61K 45/00* (2013.01); *A61K 45/06* (2013.01); *A61P 35/00* (2018.01); *C12Q 1/02* (2013.01); *G01N 33/574* (2013.01); *G01N 33/57438* (2013.01); *G01N 33/68* (2013.01); *A61K 2039/572* (2013.01); *A61K 2039/585* (2013.01); *C07K 16/18* (2013.01); *C07K 16/46* (2013.01); *G01N 2800/50* (2013.01); *G01N 2800/7028* (2013.01)

(58) Field of Classification Search
None
See application file for complete search history.

(56) References Cited

U.S. PATENT DOCUMENTS

| 5,322,678 | A | 6/1994 | Morgan, Jr. et al. |
| 5,693,762 | A | 12/1997 | Queen et al. |
| 6,436,411 | B1 | 8/2002 | Riordan et al. |
| 6,617,156 | B1 | 9/2003 | Doucette-Stamm et al. |
| 6,737,056 | B1 | 5/2004 | Presta |
| 7,297,775 | B2 | 11/2007 | Idusogie et al. |
| 7,317,091 | B2 | 1/2008 | Lazar et al. |
| 7,691,586 | B2 | 4/2010 | Watanabe et al. |
| 7,744,880 | B2 | 6/2010 | Aburatani et al. |
| 7,867,734 | B2 | 1/2011 | Nakano et al. |
| 7,871,613 | B2 * | 1/2011 | Kinoshita ............ C07K 16/303 424/130.1 |
| 7,919,086 | B2 | 4/2011 | Nakano et al. |
| 8,263,077 | B2 | 9/2012 | Aburatani et al. |
| 8,497,355 | B2 | 7/2013 | Igawa et al. |
| 8,663,929 | B2 | 3/2014 | Kataoka et al. |
| 8,937,158 | B2 | 1/2015 | Lazar et al. |
| 9,096,651 | B2 | 8/2015 | Igawa et al. |

(Continued)

FOREIGN PATENT DOCUMENTS

| CA | 2451493 A1 | 1/2003 |
| CA | 2801911 A1 | 3/2004 |

(Continued)

OTHER PUBLICATIONS

Ishiguro et al. (Cancer Research, 2008, 68(23): 9832-8,) (Year: 2008).*

(Continued)

*Primary Examiner* — Lisa V Cook

(74) *Attorney, Agent, or Firm* — Nixon & Vanderhye P.C.

(57) ABSTRACT

The present invention provides a method for determining the efficacy of a GPC3-targeting therapeutic agent for a liver cancer patient and a GPC3-targeting therapeutic agent or a preparation which is to be administered to a patient for whom it has been determined that the GPC3-targeting therapeutic agent is effective. The present invention provides, for example, a method for determining that a GPC3-targeting therapeutic agent is effective when the expression level of GPC3 per tumor cell is a predetermined value, and a GPC3-targeting therapeutic agent or a preparation which is to be administered to a patient for whom it has been determined that the GPC3-targeting therapeutic agent is effective.

16 Claims, 6 Drawing Sheets
Specification includes a Sequence Listing.

(56) References Cited

U.S. PATENT DOCUMENTS

| | | | |
|---|---|---|---|
| 9,102,739 | B2 | 8/2015 | Lazar et al. |
| 9,513,292 | B2 | 12/2016 | Aburatani et al. |
| 10,731,127 | B2 | 8/2020 | Li et al. |
| 10,782,300 | B2 | 9/2020 | Ohtomo et al. |
| 2002/0102254 | A1 | 8/2002 | Leung et al. |
| 2003/0195211 | A1 | 10/2003 | Sadhu et al. |
| 2004/0022793 | A1 | 2/2004 | Severn et al. |
| 2004/0110226 | A1 | 6/2004 | Lazar et al. |
| 2004/0236080 | A1 | 11/2004 | Aburatani et al. |
| 2005/0054832 | A1 | 3/2005 | Lazar et al. |
| 2005/0171339 | A1 | 8/2005 | Sugo et al. |
| 2005/0233392 | A1 | 10/2005 | Filmus et al. |
| 2006/0014223 | A1 | 1/2006 | Aburatani et al. |
| 2006/0040325 | A1 | 2/2006 | Wu et al. |
| 2006/0167232 | A1 | 7/2006 | Aburatani et al. |
| 2006/0188510 | A1 | 8/2006 | Aburatani et al. |
| 2006/0246550 | A1 | 11/2006 | Okumura |
| 2007/0087005 | A1 | 4/2007 | Lazar et al. |
| 2007/0190599 | A1 | 8/2007 | Nakano et al. |
| 2007/0258981 | A1 | 11/2007 | Hilbert et al. |
| 2007/0269444 | A1 | 11/2007 | Kinoshita et al. |
| 2008/0003623 | A1 | 1/2008 | Nakajima et al. |
| 2008/0008710 | A1 | 1/2008 | Aburatani et al. |
| 2008/0124330 | A1 | 5/2008 | Nakano et al. |
| 2008/0138827 | A1 | 6/2008 | Watanabe et al. |
| 2008/0166756 | A1 | 7/2008 | Tsuchiya et al. |
| 2009/0060907 | A1 | 3/2009 | Aburatani et al. |
| 2010/0167315 | A1 | 7/2010 | Thibault et al. |
| 2010/0239577 | A1 | 9/2010 | Igawa et al. |
| 2010/0248359 | A1* | 9/2010 | Nakano .......... A61P 43/00 435/325 |
| 2011/0033452 | A1 | 2/2011 | Nakano et al. |
| 2011/0091907 | A1 | 4/2011 | Kataoka et al. |
| 2011/0104157 | A1 | 5/2011 | Kinoshita et al. |
| 2015/0098941 | A1 | 4/2015 | Lazar et al. |
| 2015/0210763 | A1 | 7/2015 | Kuramochi et al. |
| 2015/0259417 | A1 | 9/2015 | Nakano et al. |
| 2015/0285806 | A1 | 10/2015 | Ohtomo et al. |
| 2015/0315278 | A1 | 11/2015 | Igawa et al. |
| 2017/0073426 | A1 | 3/2017 | Ohtomo et al. |

FOREIGN PATENT DOCUMENTS

| | | |
|---|---|---|
| CN | 1440295 A | 9/2003 |
| CN | 1440408 A | 9/2003 |
| CN | 1678740 A | 10/2005 |
| CN | 101377506 A | 3/2009 |
| CN | 102027372 A | 4/2011 |
| CN | 102046200 A | 5/2011 |
| CN | 102276721 A | 12/2011 |
| EP | 0329185 A2 | 8/1989 |
| EP | 1411118 A1 | 4/2004 |
| EP | 1541680 A1 | 6/2005 |
| EP | 1541686 A1 | 6/2005 |
| EP | 1548442 A1 | 6/2005 |
| EP | 1674111 A1 | 6/2006 |
| EP | 1816140 A1 | 8/2007 |
| EP | 1829962 A1 | 9/2007 |
| EP | 1548442 B1 | 1/2011 |
| EP | 2647706 A1 | 10/2013 |
| EP | 2863224 A1 | 4/2015 |
| EP | 2937697 A1 | 10/2015 |
| JP | H02028200 A | 1/1990 |
| JP | 2007093274 A | 4/2007 |
| JP | 2007300927 A | 11/2007 |
| JP | 2009232848 A | 10/2009 |
| JP | 201168682 A | 4/2011 |
| JP | 2015511702 A | 4/2015 |
| KR | 20050057205 A | 6/2005 |
| KR | 20100132060 A | 12/2010 |
| KR | 20110005812 A | 1/2011 |
| RU | 2001124907 A | 6/2003 |
| WO | WO-200047228 A1 | 8/2000 |
| WO | WO-200240545 A2 | 5/2002 |
| WO | WO-2003000883 A1 | 1/2003 |
| WO | WO-03057881 A1 | 7/2003 |
| WO | WO-2003100429 A2 | 12/2003 |
| WO | WO-2004022597 A1 | 3/2004 |
| WO | WO-2004022739 A1 | 3/2004 |
| WO | WO-2004022754 A1 | 3/2004 |
| WO | WO-2004023145 A1 | 3/2004 |
| WO | WO-2004029207 A2 | 4/2004 |
| WO | WO-2004038420 A1 | 5/2004 |
| WO | WO-2004099249 A2 | 11/2004 |
| WO | WO-2005023301 A1 | 3/2005 |
| WO | WO-2005106485 A1 | 11/2005 |
| WO | WO-2006006693 A1 | 1/2006 |
| WO | WO-2006038588 A1 | 4/2006 |
| WO | WO-2006046751 A1 | 5/2006 |
| WO | WO-2006067913 A1 | 6/2006 |
| WO | WO-2007005612 A2 | 1/2007 |
| WO | WO-2007047291 A2 | 4/2007 |
| WO | WO-2007059782 A1 | 5/2007 |
| WO | WO-2007137170 A2 | 11/2007 |
| WO | WO-2007137170 A3 | 11/2007 |
| WO | WO-2008032217 A2 | 3/2008 |
| WO | WO-2009041062 A1 | 4/2009 |
| WO | WO-2009116659 A1 | 9/2009 |
| WO | WO-2009122667 A1 | 10/2009 |
| WO | WO-2012145469 A1 | 10/2012 |
| WO | WO-2013118858 A1 | 8/2013 |
| WO | WO-2013127465 A1 | 9/2013 |
| WO | WO2013181543 A1 | 12/2013 |
| WO | WO-2014097648 A1 | 6/2014 |

OTHER PUBLICATIONS

Zhu et al. (Clin. Cancer Res., 2013, 19(4): 920-8, pub. online: Jan. 29, 2013) (Year: 2013).*

Hatjiharissi etal., Blood, 106, Abstract 776. (Year: 2007).*

Gluck etal., Clin. Cancer Res., 10: 2253-2264 (Year: 2004).*

Ffrench et al. (Journal of Pathology, Sep. 2015, vol. 237, Supp. Supp.1, p. S20) (Year: 2015).*

Hashiguchi et al. (Pathology International, Nov. 2010, vol. 60, No. 11, pp. 720-725). (Year: 2010).*

Almagro, J. C. and Fransson, J., "Humanization of antibodies," Frontiers in Bioscience, 13:1619-1633 (2008).

Amit, A. G., et al., "Three-Dimensional Structure of an Antigen-Antibody Complex at 2.8 Å Resolution," Science, 233(4765):747-753 (1986).

Pre-Examination Written Opinion for Brazilian Application No. PI0506125-3 dated Oct. 16, 2018, 6 pages.

Pre-Examination Written Opinion for Brazilian Application No. PI0617412-4 dated Nov. 7, 2018, 6 pages.

Brown, M., et al., "Tolerance to Single, but Not Multiple, Amino Acid Replacements in Antibody $V_H$ CDR2," J Immunol., 156:3285-3291 (1996).

Capurro, M. I., et al., "Overexpression of Glypican-3 in human hepatocellular carcinomas determined by immunohistochemistry using a monoclonal antibody," Proceedings of the American Association for Cancer Research, 93rd Annual Meeting, Mar. 2002, 93:219, Abstract No. 1097.

Chen, M., et al., "Reevaluation of glypican-3 as a serological marker for hepatocellular carcinoma," Clinical Chimica Acta., 423:105-111 (2013).

Colman, P. M., "Effects of amino acid sequence changes on antibody-antigen interactions," Research in Immunology 145:33-36 (1994).

Creative Diagnostics, Test and Assay Development, product page (2018).

Extended European Search Report for European Application No. 14874331.3 dated Feb. 7, 2019, 18 pages.

Partial Supplementary European Search Report for European Application No. 14874331.3 dated Nov. 7, 2018, 15 pages.

Extended European Search Report for European Application No. 16818042.0 dated Oct. 24, 2018, 12 pages.

Final Office Action for U.S. Appl. No. 15/309,391 dated Nov. 15, 2018, 16 pages.

Gluck, W. L., et al., "Phase I Studies of Interleukin (IL)-2 and Rituximab in B-Cell Non-Hodgkin's Lymphoma: IL-2 Mediated

(56) References Cited

OTHER PUBLICATIONS

Natural Killer Cell Expansion Correlations with Clinical Response," Clinical Cancer Research, 10:2253-2264 (2004).
Harlow, E. and Lane, D., Antibodies, A Laboratory Manual, Cold Spring Harbor Laboratory, 25-26 (1988).
Harlow, E. and Lane, D., Antibodies, A Laboratory Manual, Cold Spring Harbor Laboratory, 141-142 (1988).
Haruyama Y. et al., "High preoperative levels of serum glypican-3 containing N-terminal subunit are associated with poor prognosis in patients with hepatocellular carcinoma after partial hepatectomy," International Journal of Cancer, 137:1643-1651 (2015).
Hatjiharissi, E., et al., "Individuals Expressing FcγRIIIA-158 V/V and V/F Show Increased NK Cell Surface Expression of FcgRIIIA (CD16), Rituximab Binding, and Demonstrate Higher Levels of ADCC Activity in Response to Rituximab," Blood 106:Abstract 776 (2005).
Hatjiharissi, E., et al., "Increased natural killer cell expression of CD16, augmented binding and ADCC activity to rituximab among individuals expressing the FcγRIIIa-158 V/V and V/F polymorphism," Blood, 110:2561-2564 (2007).
Hippo, Y., et al., "Identification of Soluble $NH_2$-Terminal Fragment of Glypican-3 as a Serological Marker for Early-Stage Hepatocellular Carcinoma," Cancer Research, 64:2418-2423 (2004).
Hearing Notice dated Jan. 29, 2018 in Indian Patent Application No. 2357/CHENP/2010.
Ishiguro, T., et al., "Anti-Glypican 3 Antibody as a Potential Antitumor Agent for Human Liver Cancer," Cancer Res., 68(23):9832-9838 (2008).
Khantasup, K., et al., "Design and Generation of Humanized Single-chain Fv Derived from Mouse Hybridoma for Potential Targeting Application," Monoclonal Antibodies in Immunodiagnosis and Immunotherapy, 34(6):404-417 (2015).
Kim, M., et al., "Structure of the protein core of the glypican Dally-like and localization of a region important for hedgehog signaling," PNAS, 108(32):13112-13117 (2011).
Lei, J., et al., "Prediction of HLA-A2 restricted cytotoxic T lymphocyte epitope in high expression of tumor antigen glypican-3 in primary liver cancer," Jiefangjun Yiyao Zazhi, Journal, 25(8):26-28 (2013).
Li, S., et al., "Prokaryotic Expression of GPC3/MXR7 and Preparation of Anti-GPC3/MXR7 Antibody," China Journal of Modern Medicine 13(8):15-17 (2003), with English Abstract.
Mavilio, D., et al., "Characterization of $CD56^-/CD16^+$ natural killer (NK) cells: A highly dysfunctional NK subset expanded in HIV-infected viremic individuals," PNAS, 102(8):2886-2891 (2005).
Nakano, K., et al., "Anti-glypican 3 antibodies cause ADCC against human hepatocellular carcinoma cells," Biochem Biophys Res Comm., 378:279-284 (2009).
Office Action for Australian Application No. 2013365430 dated Dec. 13, 2018, 8 pages.
Office Action for Brazilian Application No. PI0909672-8 dated Apr. 18, 2018, 7 pages.
Office Action for Chinese Application No. 201580024198.X dated Sep. 5, 2018, 19 pages.
Office Action for Chinese Application No. 201610183223.5 dated Jan. 9, 2019, 23 pages.
Office Action for Japanese Application No. 2015-554492 dated Jun. 19, 2018, 6 pages.
Office Action for Mexican Application No. MX/a/2015/007714 dated Sep. 26, 2018, 6 pages.
Office Action for Norwegian U.S. Appl. No. 20/063,539 dated Feb. 8, 2018, 9 pages.
Office Action for Russian Application No. 2015129697 dated Dec. 7, 2017, 12 pages.
Office Action for U.S. Appl. No. 14/713,416 dated Aug. 15, 2018, 16 pages.
Office Action for U.S. Appl. No. 15/107,316 dated May 4, 2018, 50 pages.
Office Action for U.S. Appl. No. 15/288,508 dated Jan. 9, 2018, 52 pages.
Office Action for U.S. Appl. No. 15/288,508 dated Sep. 21, 2018, 23 pages.
Office Action for U.S. Appl. No. 15/309,391 dated May 15, 2018, 44 pages.
Pilia, G., et al., "Mutations in GPC3, a glypican gene, cause the Simpson-Golabi-Behmel overgrowth syndrome," Nature Genetics, 12:241-247 (1996).
Restriction Requirement for U.S. Appl. No. 15/309,391 dated Jan. 19, 2018, 10 pages.
Rudikoff, S., et al., "Single amino acid substitute altering antigen-binding specificity," Proc Natl Acad Sci., 79:1979-1983 (1982).
Semenova, A. I., "Monitoring treatment efficacy and detecting relapses using biomarkers," Practical Oncology, 12(4):171-177 (2011), with English Abstract.
Sun, C., et al., "Suppression of Glypican 3 Inhibits Growth of Hepatocellular Carcinoma Cells through Up-Regulation of TGF-β2," Neoplasia 13(8):735-747 (2011).
United States Patent and Trademark Office, Federal Register Notice, 66(4):1099-1111 (2001).
Vajdos, F. F., "Comprehensive Functional Maps of the Antigen-binding Site of an Anti-ErbB2 Antibody Obtained with Shotgun Scanning Mutagenesis," J Mol Biol., 320(2):415-428 (2002).
Van Regenmortel, M. H. V., "Mapping Epitope Structure and Activity: From One-Dimensional Prediction to Four-Dimensional Description of Antigenic Specificity," Methods: A Companion to Methods in Enzymology 9(54):465-472 (1996).
Weisstein, E. W., "Combination," MathWorld—A Wolfram Web Resource (2018).
Yamauchi, N., et al., "The glypican 3 oncofetal protein is a promising disgnostic marker for hepatocellular carcinoma," Modern Pathology, 18:1591-1598 (2005).
Yorita, K., et al., "Prognostic significance of circumferential cell surface immunoreactivity of glypican-3 in hepatocellular carcinoma," Liver International 21 (1):120-131 (2011).
Zhang, Q., et al., "Comparision of chemiluminescence enzyme immunoassay based on magnetic microparticles with traditional colorimetric ELISA for the detection of serum α-fetoprotein," Journal Pharmaceutical Analysis, 2(2):130-135 (2012).
Zynger, D. L., et al., "Glypican 3: A Novel Marker in Testicular Germ Cell Tumors," Am J Surg Pathol., 30:1570-1575 (2006).
Office Action dated Sep. 18, 2019 in Thai Patent Application No. 0501003166, filed Jul. 8, 2005.
Office Action dated Jul. 10, 2019 in U.S. Appl. No. 15/309,391, Ohtomo, T., et al., filed Nov. 7, 2016.
Tefferi, A., et al., "How to Interpret and Pursue an Abnormal Complete Blood Cell Count in Adults," Mayo Clin Proc., 80(7):923-936 (2005).
Kappel, C. A., et al., "Regulating gene expression in transgenic animals," Current Opinion in Biotechnology 3:548-553 (1992).
Paul, W. E., "Fundamental Immunology," Third Edition, 292-295 (1993).
Portolano, S., et al., "Lack of Promiscuity in Autoantigen-Specific H and L Chain Combinations as Revealed by Human H and L Chain Roulette," J Immunol 150(3):880-887 (1993).
Houdebine, L. M., "Production of pharmaceutical proteins from transgenic animals," J Biotech 34:269-287 (1994).
Takai, H., et al., "Histopathological analyses of the antitumor activity of anti-glypican-3 antibody (GC33) in human liver cancer xenograft models," Cancer Biology & Therapy 8(10):930-938 (2009).
Takenaka, K., et al., "Results of 280 Liver Resections for Hepatocellular Carcinoma," Arch Surg 131:71-76 (1996).
Wall, R. J., "Transgenic Livestock: Progress and Prospects for the Future," Theriogenology, 45:57-68 (1996).
Lund, J., et al., "Multiple Interactions of IgG with Its Core Oligosaccharide Can Modulate Recognition by Complement and Human Fcγ Receptor I and Influence the Synthesis of Its Oligosaccharide Chains," J Immunol 157:4963-4969 (1996).
Lage, H., et al., "Expression of a glypican-related 62-kDa antigen is decreased in hepatocellular carcinoma in correspondence to the grade of tumor differentiation," Virchows Arch 438(6):567-573 (2001).
Yen, C. J., et al., "Randomized phase II trial of intravenous RO5137382/GC33 at 1600 mg every other week and placebo in

(56) References Cited

OTHER PUBLICATIONS previously treated patients with unresectable advanced hepatocellular carcinoma (HCC; NCT01507168)," J Clin Oncol 32(15):4102, abstract (2014).
Llovet, J. M., et al., "Hepatocellular carcinoma," Lancet 362:1907-1917 (2003).
Nakatsura, T., et al., "Glypican-3, overexpressed specifically in human hepatocellular carcinoma, is a novel tumor marker," Biochemical & Biophysical Research Communications 306(1):16-25 (2003).
Sung, Y. K., et al., "Glypican-3 is overexpressed in human hepatocellular carcinoma," Cancer Sci 94(3):259-262 (2003).
Abou-Alfa, G. K., et al., "Randomized phase II placebo controlled study of codrituzumab in previously treated patients with advanced hepatocellular carcinoma," J Hepatology 65(2):289-295 (2016).
Capurro, M., et al., "Glypican-3: A Novel Serum and Histochemical Marker for Hepatocelluar Carcinoma," Gastroenterology 125(1):89-97 (2003).
De Cat, B., et al. "Processing by proprotein convertases is required for glypican-3 modulation of cell survival, Wnt signaling, and gastrulation movements," J Cell Biol 163(3):625-635 (2003).
Bosch, F. X., et al., "Primary Liver Cancer: Worldwide Incidence and Trends," Gastroenterology 127(5):S5-S16 (2004).
Yamane-Ohnuki, N., et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnol Bioeng 87(5):614-622 (2004).
Yeo, W., et al., "Randomized Phase III Study of Doxorubicin Versus Cisplatin/lnterferon α-2b/Doxorubicin/Fluorouracil (PIAF) Combination Chemotherapy for Unresectable Hepatocellular Carcinoma," J Natl Cancer Inst 97(20):1532-1538 (2005).
Traister, A., et al., "Mammalian Notum induces the release of glypicans and other GPI-anchored proteins from the cell surface," Biochem J 410:503-511 (2008).
Llovet, J. M., et al., "Sorafenib in Advanced Hepatocelluar Carcinoma," N Engl J Med 359(4):378-390 (2008).
Cheng, A. L., et al., "Efficacy and safety of sorafenib in patients in the Asia-Pacific region with advanced hepatocellular carcinoma: a phase III radomised, double-blind, placebo-controlled trial," Lancet Oncol 10:25-34 (2009).
Ho, M. and Kim, H., "Glypican-3: A new target for cancer immunotherapy," European Journal of Cancer 47:333-338 (2011).
Sawada, Y., et al., "Phase I Trial of a Glypican-3-Derived Peptide Vaccine for Advanced Hepatocellular Carcinoma: Immunologic Evidence and Potential for Improving Overall Survival," Clin Cancer Res 18(13):3686-3696 (2012).
Zhu, A. X., et al., "First-in-Man Phase I Study of GC33, a Novel Recombinant Humanized Antibody Against Glypican-3, in Patients with Advanced Hepatocellular Carcinoma," Clin Cancer Res 19(4):920-928 (2013).
Midorikawa, Y., et al., "Glypican-3, Overexpressed in Hepatocellular Carcinoma, Modulates FGF2 and BMP-7 Signaling," Int J Cancer 103(4):455-465 (2003).
Raju, T. S., "Glycosylation Variations with Expression Systems," BioProcess International 44-53 (2003).
Konno, Y., et al., "Fucose content of monoclonal antibodies can be controlled by culture medium osmolality for high antibody-dependent cellular cytotoxicity," Cytotechnology 64(3):249-265 (2012).
Kunkel, J. P., et al., "Comparisons of the Glycosylation of a Monoclonal Antibody Produced under Nominally Identical Cell Culture Conditions in Two Different Bioreactors," Biotechnol Prog 16(3):462-470 (2000).
Kawaida, M. et al., "104$^{th}$ Conference of the Japanese Society of Pathology—Nagoya Congress Center" 104(1):324 (2015), including partial English translation.
Ikeda, M., et al., "Japanese phase I study of GC33, a humanized antibody against glypican-3 for advanced hepatocellular carcinoma," Cancer Sci 105(4):455-462 (2014).
Endo, M., "A novel molecular targeted therapy, humanized anti-glypican 3 antibody (GC33), for the treatment of unresectable hepatocellular cancer," Medical Science Digest 39(9):440-443 (2013), including English translation.
Hashiguchi, A., et al., "Using immunofluorescent digital slide technology to quantify protein expression in archival paraffin-embedded tissue sections," Pathol Intl 60(11):720-725 (2010).
Fischer, L., et al., "The anti-lymphoma effect of antibody-mediated immunotherapy is based on an increased degranulation peripheral blood natural killer (NK) cells," Exp Hematol 34(6):753-759 (2006).
Bendig, M. M., "Humanization of Rodent Monoclonal Antibodies by CDR Grafting," Methods: A Comparison to Methods in Enzymology 8:83-93 (1995).
Ofuji, K. and Nakatsura, T., "Vaccine Therapy for Hepatic Cancer," Consensus of Cancer Therapy 12(2):114-117 (2013), including English translation.
Declaration of Dr. Greg A. Lazar Under 35 U.S.C. §1.131 dated Dec. 27, 2010 in U.S. Appl. No. 11/841,654, filed Aug. 20, 2007.
Llovet, J. M., et al., "A Molecular Signature to Discriminate Dysplastic Nodules From Early Hepatocellular Carcinoma in HCV Cirrhosis," Gastroenterology 131(6):1758-1767 (2006).
Chugai Pharmaceutical (Organization Study ID GC-001US), ClinicalTrials.gov, NCT00746317 dated Nov. 16, 2010, "A Phase I, Open-Label, Multi-center, Dose-escalation Study of the Safety, Tolerability, and Pharmacokinetics of GC33 Administered Weekly in Patients With Advanced or Metastatic Hepatocellular Carcinoma (HCC)," 4 pages.
International Search Report dated Sep. 20, 2016 for International Application No. PCT/JP2016/069493, 7 pages, including English translation.
Bikoue, A., et al., "Quantitative Analysis of Leukocyte Membrane Antigen Expression: Normal Adult Values," Cytometry (Communications in Clinical Cytometry), 26:137-147 (1996).
Communication pursuant to Article 94(3) EPC from the European Patent Office dated Oct. 9, 2020 in European Patent Application No. 15 789 676.2, 6 pages.
Korean Office Action from The Korean Intellectual Property Office in Korean Application No. 10-2015-7013955 dated Dec. 17, 2019.
Korean Notice of Allowance from The Korean Intellectual Property Office in Korean Application No. 10-2015-7013955 dated Nov. 23, 2020, 4 pages.
New Zealand Office Action from the New Zealand Intellectual Property Office dated Jun. 25, 2020 in New Zealand Patent No. 707774, 10 pages.
Phung, Y., et al., "High-affinity monoclonal antibodies to cell surface tumor antigen glypican-3 generated through a combination of peptide immunization and flow cytometry screening," mAbs, 4(5):592-599 (2012).
Final Office Action dated Apr. 5, 2021 in U.S. Appl. No. 14/713,416, filed May 15, 2015, Nakano et al.
Office Action dated Jul. 15, 2021 in U.S. Appl. No. 15/309,391, filed Nov. 7, 2016, Ohtomo et al.

* cited by examiner

SEQUENCE LISTING

```
<160> NUMBER OF SEQ ID NOS: 82

<210> SEQ ID NO 1
<211> LENGTH: 580
<212> TYPE: PRT
<213> ORGANISM: homo sapiens

<400> SEQUENCE: 1

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Asp
                20                  25                  30

Ala Thr Cys His Gln Val Arg Ser Phe Phe Gln Arg Leu Gln Pro Gly
            35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
```

```
                100             105             110
Glu Ala Phe Glu Ile Val Val Arg His Ala Lys Asn Tyr Thr Asn Ala
            115             120             125
Met Phe Lys Asn Asn Tyr Pro Ser Leu Thr Pro Gln Ala Phe Glu Phe
            130             135             140
Val Gly Glu Phe Phe Thr Asp Val Ser Leu Tyr Ile Leu Gly Ser Asp
145             150             155             160
Ile Asn Val Asp Asp Met Val Asn Glu Leu Phe Asp Ser Leu Phe Pro
                165             170             175
Val Ile Tyr Thr Gln Leu Met Asn Pro Gly Leu Pro Asp Ser Ala Leu
                180             185             190
Asp Ile Asn Glu Cys Leu Arg Gly Ala Arg Arg Asp Leu Lys Val Phe
                195             200             205
Gly Asn Phe Pro Lys Leu Ile Met Thr Gln Val Ser Lys Ser Leu Gln
                210             215             220
Val Thr Arg Ile Phe Leu Gln Ala Leu Asn Leu Gly Ile Glu Val Ile
225             230             235             240
Asn Thr Thr Asp His Leu Lys Phe Ser Lys Asp Cys Gly Arg Met Leu
                245             250             255
Thr Arg Met Trp Tyr Cys Ser Tyr Cys Gln Gly Leu Met Met Val Lys
                260             265             270
Pro Cys Gly Gly Tyr Cys Asn Val Val Met Gln Gly Cys Met Ala Gly
                275             280             285
Val Val Glu Ile Asp Lys Tyr Trp Arg Glu Tyr Ile Leu Ser Leu Glu
                290             295             300
Glu Leu Val Asn Gly Met Tyr Arg Ile Tyr Asp Met Glu Asn Val Leu
305             310             315             320
Leu Gly Leu Phe Ser Thr Ile His Asp Ser Ile Gln Tyr Val Gln Lys
                325             330             335
Asn Ala Gly Lys Leu Thr Thr Thr Ile Gly Lys Leu Cys Ala His Ser
                340             345             350
Gln Gln Arg Gln Tyr Arg Ser Ala Tyr Tyr Pro Glu Asp Leu Phe Ile
                355             360             365
Asp Lys Lys Val Leu Lys Val Ala His Val Glu His Glu Glu Thr Leu
                370             375             380
Ser Ser Arg Arg Arg Glu Leu Ile Gln Lys Leu Lys Ser Phe Ile Ser
385             390             395             400
Phe Tyr Ser Ala Leu Pro Gly Tyr Ile Cys Ser His Ser Pro Val Ala
                405             410             415
Glu Asn Asp Thr Leu Cys Trp Asn Gly Gln Glu Leu Val Glu Arg Tyr
                420             425             430
Ser Gln Lys Ala Ala Arg Asn Gly Met Lys Asn Gln Phe Asn Leu His
                435             440             445
Glu Leu Lys Met Lys Gly Pro Glu Pro Val Val Ser Gln Ile Ile Asp
                450             455             460
Lys Leu Lys His Ile Asn Gln Leu Leu Arg Thr Met Ser Met Pro Lys
465             470             475             480
Gly Arg Val Leu Asp Lys Asn Leu Asp Glu Glu Gly Phe Glu Ser Gly
                485             490             495
Asp Cys Gly Asp Asp Glu Asp Glu Cys Ile Gly Gly Ser Gly Asp Gly
                500             505             510
Met Ile Lys Val Lys Asn Gln Leu Arg Phe Leu Ala Glu Leu Ala Tyr
                515             520             525
```

```
Asp Leu Asp Val Asp Asp Ala Pro Gly Asn Ser Gln Gln Ala Thr Pro
            530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 2
<211> LENGTH: 9
<212> TYPE: PRT
<213> ORGANISM: homo sapiens

<400> SEQUENCE: 2

Phe Val Gly Glu Phe Phe Thr Asp Val
1               5

<210> SEQ ID NO 3
<211> LENGTH: 9
<212> TYPE: PRT
<213> ORGANISM: homo sapiens

<400> SEQUENCE: 3

Glu Tyr Ile Leu Ser Leu Glu Glu Leu
1               5

<210> SEQ ID NO 4
<211> LENGTH: 5
<212> TYPE: PRT
<213> ORGANISM: Mus musculus

<400> SEQUENCE: 4

Asp Tyr Ser Met His
1               5

<210> SEQ ID NO 5
<211> LENGTH: 17
<212> TYPE: PRT
<213> ORGANISM: Mus musculus

<400> SEQUENCE: 5

Trp Ile Asn Thr Glu Thr Gly Glu Pro Thr Tyr Ala Asp Asp Phe Lys
1               5                   10                  15

Gly

<210> SEQ ID NO 6
<211> LENGTH: 2
<212> TYPE: PRT
<213> ORGANISM: Mus musculus

<400> SEQUENCE: 6

Leu Tyr
1

<210> SEQ ID NO 7
<211> LENGTH: 16
<212> TYPE: PRT
<213> ORGANISM: Mus musculus

<400> SEQUENCE: 7

Lys Ser Ser Gln Ser Leu Leu His Ser Asp Gly Lys Thr Phe Leu Asn
```

```
1               5                  10                 15
```

<210> SEQ ID NO 8
<211> LENGTH: 7
<212> TYPE: PRT
<213> ORGANISM: Mus musculus

<400> SEQUENCE: 8

Leu Val Ser Arg Leu Asp Ser
1               5

<210> SEQ ID NO 9
<211> LENGTH: 9
<212> TYPE: PRT
<213> ORGANISM: Mus musculus

<400> SEQUENCE: 9

Cys Gln Gly Thr His Phe Pro Arg Thr
1               5

<210> SEQ ID NO 10
<211> LENGTH: 111
<212> TYPE: PRT
<213> ORGANISM: Mus musculus

<400> SEQUENCE: 10

Gln Ile Gln Leu Glu Gln Ser Gly Pro Glu Leu Lys Lys Pro Gly Glu
1               5                  10                 15

Thr Val Lys Ile Ser Cys Lys Ala Ser Gly Tyr Ile Phe Arg Asp Tyr
                20                  25                 30

Ser Met His Trp Val Lys Gln Ala Pro Gly Lys Gly Leu Lys Trp Met
            35                  40                 45

Gly Trp Ile Asn Thr Glu Thr Gly Glu Pro Thr Tyr Ala Asp Asp Phe
    50                  55                 60

Lys Gly Arg Phe Ala Phe Ser Leu Glu Thr Ser Ala Ser Thr Ala Tyr
65                  70                  75                 80

Leu Gln Ile Asn Asn Leu Lys Asn Glu Asp Thr Ala Thr Tyr Phe Cys
                85                  90                 95

Thr Ser Leu Tyr Trp Gly Gln Gly Thr Leu Val Thr Val Ser Ala
            100                 105                110

<210> SEQ ID NO 11
<211> LENGTH: 112
<212> TYPE: PRT
<213> ORGANISM: Mus musculus

<400> SEQUENCE: 11

Asp Val Val Met Thr Gln Thr Pro Leu Thr Leu Ser Val Thr Leu Gly
1               5                  10                 15

Gln Pro Ala Ser Ile Ser Cys Lys Ser Ser Gln Ser Leu Leu His Ser
                20                  25                 30

Asp Gly Lys Thr Phe Leu Asn Trp Leu Leu Gln Arg Pro Gly Gln Ser
            35                  40                 45

Pro Lys Arg Leu Ile Tyr Leu Val Ser Arg Leu Asp Ser Gly Val Pro
    50                  55                 60

Asp Arg Phe Thr Gly Ser Gly Ser Gly Thr Asp Phe Thr Leu Lys Ile
65                  70                  75                 80

Ser Arg Val Glu Ala Glu Asp Leu Gly Val Tyr Tyr Cys Cys Gln Gly
                85                  90                 95

-continued

Thr His Phe Pro Arg Thr Phe Gly Gly Gly Thr Arg Leu Glu Ile Lys
            100                 105                 110

<210> SEQ ID NO 12
<211> LENGTH: 7
<212> TYPE: PRT
<213> ORGANISM: Mus musculus

<400> SEQUENCE: 12

Thr Tyr Gly Met Gly Val Gly
1               5

<210> SEQ ID NO 13
<211> LENGTH: 16
<212> TYPE: PRT
<213> ORGANISM: Mus musculus

<400> SEQUENCE: 13

Asn Ile Trp Trp His Asp Asp Lys Tyr Tyr Asn Ser Ala Leu Lys Ser
1               5                   10                  15

<210> SEQ ID NO 14
<211> LENGTH: 14
<212> TYPE: PRT
<213> ORGANISM: Mus musculus

<400> SEQUENCE: 14

Ile Ala Pro Arg Tyr Asn Lys Tyr Glu Gly Phe Phe Ala Phe
1               5                   10

<210> SEQ ID NO 15
<211> LENGTH: 16
<212> TYPE: PRT
<213> ORGANISM: Mus musculus

<400> SEQUENCE: 15

Arg Ser Ser Gln Ser Ile Val His Ser Asn Gly Asn Thr Tyr Leu Glu
1               5                   10                  15

<210> SEQ ID NO 16
<211> LENGTH: 7
<212> TYPE: PRT
<213> ORGANISM: Mus musculus

<400> SEQUENCE: 16

Lys Val Ser Asn Arg Phe Ser
1               5

<210> SEQ ID NO 17
<211> LENGTH: 9
<212> TYPE: PRT
<213> ORGANISM: Mus musculus

<400> SEQUENCE: 17

Phe Gln Gly Ser His Val Pro Trp Thr
1               5

<210> SEQ ID NO 18
<211> LENGTH: 124
<212> TYPE: PRT
<213> ORGANISM: Mus musculus

<400> SEQUENCE: 18

Gln Val Thr Leu Lys Glu Ser Gly Pro Gly Ile Leu Gln Pro Ser Gln
1               5                   10                  15

```
Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
            35                  40                  45

Trp Leu Ala Asn Ile Trp Trp His Asp Asp Lys Tyr Tyr Asn Ser Ala
 50                      55                  60

Leu Lys Ser Arg Leu Thr Ile Ser Lys Asp Ile Ser Asn Asn Gln Val
 65                  70                  75                  80

Phe Leu Lys Ile Ser Ser Val Asp Thr Ala Asp Thr Ala Thr Tyr Tyr
                 85                  90                  95

Cys Ala Gln Ile Ala Pro Arg Tyr Asn Lys Tyr Glu Gly Phe Phe Ala
            100                 105                 110

Phe Trp Gly Gln Gly Thr Leu Val Thr Val Ser Ala
            115                 120
```

<210> SEQ ID NO 19
<211> LENGTH: 112
<212> TYPE: PRT
<213> ORGANISM: Mus musculus

<400> SEQUENCE: 19

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
            100                 105                 110
```

<210> SEQ ID NO 20
<211> LENGTH: 5
<212> TYPE: PRT
<213> ORGANISM: Mus musculus

<400> SEQUENCE: 20

```
Asp Tyr Glu Met His
 1               5
```

<210> SEQ ID NO 21
<211> LENGTH: 17
<212> TYPE: PRT
<213> ORGANISM: Mus musculus

<400> SEQUENCE: 21

```
Ala Leu Asp Pro Lys Thr Gly Asp Thr Ala Tyr Ser Gln Lys Phe Lys
 1               5                  10                  15

Gly
```

<210> SEQ ID NO 22
<211> LENGTH: 6
<212> TYPE: PRT

```
<213> ORGANISM: Mus musculus

<400> SEQUENCE: 22

Phe Tyr Ser Tyr Thr Tyr
1               5

<210> SEQ ID NO 23
<211> LENGTH: 16
<212> TYPE: PRT
<213> ORGANISM: Mus musculus

<400> SEQUENCE: 23

Arg Ser Ser Gln Ser Leu Val His Ser Asn Arg Asn Thr Tyr Leu His
1               5                  10                  15

<210> SEQ ID NO 24
<211> LENGTH: 7
<212> TYPE: PRT
<213> ORGANISM: Mus musculus

<400> SEQUENCE: 24

Lys Val Ser Asn Arg Phe Ser
1               5

<210> SEQ ID NO 25
<211> LENGTH: 9
<212> TYPE: PRT
<213> ORGANISM: Mus musculus

<400> SEQUENCE: 25

Ser Gln Asn Thr His Val Pro Pro Thr
1               5

<210> SEQ ID NO 26
<211> LENGTH: 115
<212> TYPE: PRT
<213> ORGANISM: Mus musculus

<400> SEQUENCE: 26

Gln Val Gln Leu Gln Gln Ser Gly Ala Glu Leu Val Arg Pro Gly Ala
1               5                  10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Ile
        35                  40                  45

Gly Ala Leu Asp Pro Lys Thr Gly Asp Thr Ala Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ala
        115

<210> SEQ ID NO 27
<211> LENGTH: 112
<212> TYPE: PRT
<213> ORGANISM: Mus musculus

<400> SEQUENCE: 27
```

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Phe Cys Ser Gln Asn
                85                  90                  95

Thr His Val Pro Pro Thr Phe Gly Ser Gly Thr Lys Leu Glu Ile Lys
            100                 105                 110
```

<210> SEQ ID NO 28
<211> LENGTH: 5
<212> TYPE: PRT
<213> ORGANISM: Mus musculus

<400> SEQUENCE: 28

```
Ile Asn Ala Met Asn
1               5
```

<210> SEQ ID NO 29
<211> LENGTH: 19
<212> TYPE: PRT
<213> ORGANISM: Mus musculus

<400> SEQUENCE: 29

```
Arg Ile Arg Ser Glu Ser Asn Asn Tyr Ala Thr Tyr Tyr Gly Asp Ser
1               5                   10                  15

Val Lys Asp
```

<210> SEQ ID NO 30
<211> LENGTH: 8
<212> TYPE: PRT
<213> ORGANISM: Mus musculus

<400> SEQUENCE: 30

```
Glu Val Thr Thr Ser Phe Ala Tyr
1               5
```

<210> SEQ ID NO 31
<211> LENGTH: 16
<212> TYPE: PRT
<213> ORGANISM: Mus musculus

<400> SEQUENCE: 31

```
Lys Ser Ser Lys Ser Leu Leu His Ser Asn Gly Asn Thr Tyr Leu Asn
1               5                   10                  15
```

<210> SEQ ID NO 32
<211> LENGTH: 7
<212> TYPE: PRT
<213> ORGANISM: Mus musculus

<400> SEQUENCE: 32

```
Trp Met Ser Asn Leu Ala Ser
1               5
```

<210> SEQ ID NO 33
<211> LENGTH: 9
<212> TYPE: PRT
<213> ORGANISM: Mus musculus

<400> SEQUENCE: 33

Met Gln His Ile Glu Tyr Pro Phe Thr
1               5

<210> SEQ ID NO 34
<211> LENGTH: 119
<212> TYPE: PRT
<213> ORGANISM: Mus musculus

<400> SEQUENCE: 34

Glu Val Gln Leu Val Glu Thr Gly Gly Gly Leu Val Gln Pro Glu Gly
1               5                   10                  15

Ser Leu Lys Leu Ser Cys Ala Ala Ser Gly Phe Ser Phe Asn Ile Asn
                20                  25                  30

Ala Met Asn Trp Val Arg Gln Ala Pro Gly Lys Gly Leu Glu Trp Val
            35                  40                  45

Ala Arg Ile Arg Ser Glu Ser Asn Asn Tyr Ala Thr Tyr Tyr Gly Asp
        50                  55                  60

Ser Val Lys Asp Arg Phe Thr Ile Ser Arg Asp Asp Ser Gln Asn Met
65                  70                  75                  80

Leu Tyr Leu Gln Met Asn Asn Leu Lys Thr Glu Asp Thr Ala Ile Tyr
                85                  90                  95

Tyr Cys Val Arg Glu Val Thr Thr Ser Phe Ala Tyr Trp Gly Gln Gly
            100                 105                 110

Thr Leu Val Thr Val Ser Ala
        115

<210> SEQ ID NO 35
<211> LENGTH: 112
<212> TYPE: PRT
<213> ORGANISM: Mus musculus

<400> SEQUENCE: 35

Asp Ile Val Met Thr Gln Ser Ala Pro Ser Val Pro Val Thr Pro Gly
1               5                   10                  15

Glu Ser Val Ser Ile Ser Cys Lys Ser Ser Lys Ser Leu Leu His Ser
                20                  25                  30

Asn Gly Asn Thr Tyr Leu Asn Trp Phe Leu Gln Arg Pro Gly Gln Ser
            35                  40                  45

Pro Gln Leu Leu Ile Tyr Trp Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Ile Glu Tyr Pro Phe Thr Phe Gly Thr Gly Thr Lys Leu Glu Ile Lys
            100                 105                 110

<210> SEQ ID NO 36
<211> LENGTH: 5
<212> TYPE: PRT
<213> ORGANISM: Mus musculus

<400> SEQUENCE: 36

Ala Ser Ala Met Asn
1               5

<210> SEQ ID NO 37
<211> LENGTH: 19
<212> TYPE: PRT
<213> ORGANISM: Mus musculus

<400> SEQUENCE: 37

Arg Ile Arg Ser Lys Ser Asn Asn Tyr Ala Ile Tyr Tyr Ala Asp Ser
1               5                   10                  15

Val Lys Asp

<210> SEQ ID NO 38
<211> LENGTH: 12
<212> TYPE: PRT
<213> ORGANISM: Mus musculus

<400> SEQUENCE: 38

Asp Pro Gly Tyr Tyr Gly Asn Pro Trp Phe Ala Tyr
1               5                   10

<210> SEQ ID NO 39
<211> LENGTH: 16
<212> TYPE: PRT
<213> ORGANISM: Mus musculus

<400> SEQUENCE: 39

Arg Ser Ser Lys Ser Leu Leu His Ser Tyr Asp Ile Thr Tyr Leu Tyr
1               5                   10                  15

<210> SEQ ID NO 40
<211> LENGTH: 7
<212> TYPE: PRT
<213> ORGANISM: Mus musculus

<400> SEQUENCE: 40

Gln Met Ser Asn Leu Ala Ser
1               5

<210> SEQ ID NO 41
<211> LENGTH: 9
<212> TYPE: PRT
<213> ORGANISM: Mus musculus

<400> SEQUENCE: 41

Ala Gln Asn Leu Glu Leu Pro Pro Thr
1               5

<210> SEQ ID NO 42
<211> LENGTH: 123
<212> TYPE: PRT
<213> ORGANISM: Mus musculus

<400> SEQUENCE: 42

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Ala Ser
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Ile Tyr Tyr Ala Asp

```
            50                  55                  60
Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Met Tyr
                 85                  90                  95

Tyr Cys Val Arg Asp Pro Gly Tyr Tyr Gly Asn Pro Trp Phe Ala Tyr
            100                 105                 110

Trp Gly Gln Gly Thr Leu Val Thr Val Ser Ala
            115                 120

<210> SEQ ID NO 43
<211> LENGTH: 112
<212> TYPE: PRT
<213> ORGANISM: Mus musculus

<400> SEQUENCE: 43

Asp Ile Val Met Thr Gln Ala Ala Phe Ser Asn Pro Val Thr Leu Gly
  1               5                  10                  15

Thr Ser Ala Ser Ile Ser Cys Arg Ser Lys Ser Leu Leu His Ser
                 20                  25                  30

Tyr Asp Ile Thr Tyr Leu Tyr Trp Tyr Leu Gln Lys Pro Gly Gln Ser
             35                  40                  45

Pro Gln Leu Leu Ile Tyr Gln Met Ser Asn Leu Ala Ser Gly Val Pro
         50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Pro Thr Phe Gly Gly Gly Thr Lys Leu Glu Ile Lys
            100                 105                 110

<210> SEQ ID NO 44
<211> LENGTH: 115
<212> TYPE: PRT
<213> ORGANISM: Artificial Sequence
<220> FEATURE:
<223> OTHER INFORMATION: modified antibody fragment

<400> SEQUENCE: 44

Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Glu Met His Trp Val Arg Gln Ala Pro Gly Gln Gly Leu Glu Trp Met
             35                  40                  45

Gly Ala Leu Asp Pro Lys Thr Gly Asp Thr Ala Tyr Ser Gln Lys Phe
         50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Tyr Ser Tyr Thr Tyr Trp Gly Gln Gly Thr Leu Val Thr
            100                 105                 110

Val Ser Ser
        115

<210> SEQ ID NO 45
```

```
<211> LENGTH: 115
<212> TYPE: PRT
<213> ORGANISM: Artificial Sequence
<220> FEATURE:
<223> OTHER INFORMATION: modified antibody fragment

<400> SEQUENCE: 45

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 46
<211> LENGTH: 115
<212> TYPE: PRT
<213> ORGANISM: Artificial Sequence
<220> FEATURE:
<223> OTHER INFORMATION: modified antibody fragment

<400> SEQUENCE: 46

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 47
<211> LENGTH: 115
<212> TYPE: PRT
<213> ORGANISM: Artificial Sequence
<220> FEATURE:
<223> OTHER INFORMATION: modified antibody fragment

<400> SEQUENCE: 47

Gln Val Gln Leu Val Glu Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 48
<211> LENGTH: 115
<212> TYPE: PRT
<213> ORGANISM: Artificial Sequence
<220> FEATURE:
<223> OTHER INFORMATION: modified antibody fragment

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 49
<211> LENGTH: 115
<212> TYPE: PRT
<213> ORGANISM: Artificial Sequence
<220> FEATURE:
<223> OTHER INFORMATION: modified antibody fragment

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
 65                  70                  75                  80
```

Met Glu Leu Ser Ser Leu Arg Ser Glu Asp Thr Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 50
<211> LENGTH: 115
<212> TYPE: PRT
<213> ORGANISM: Artificial Sequence
<220> FEATURE:
<223> OTHER INFORMATION: modified antibody fragment

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
            85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 51
<211> LENGTH: 112
<212> TYPE: PRT
<213> ORGANISM: Artificial Sequence
<220> FEATURE:
<223> OTHER INFORMATION: modified antibody fragment

<400> SEQUENCE: 51

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Pro Thr Phe Gly Gln Gly Thr Lys Leu Glu Ile Lys
            100                 105                 110

<210> SEQ ID NO 52
<211> LENGTH: 112
<212> TYPE: PRT

```
<213> ORGANISM: Artificial Sequence
<220> FEATURE:
<223> OTHER INFORMATION: modified antibody fragment

<400> SEQUENCE: 52

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: modified antibody fragment

<400> SEQUENCE: 53

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: modified antibody fragment

<400> SEQUENCE: 54

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Glu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 55
<211> LENGTH: 112
<212> TYPE: PRT
<213> ORGANISM: Artificial Sequence
<220> FEATURE:
<223> OTHER INFORMATION: modified antibody fragment

<400> SEQUENCE: 55

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Phe Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: modified antibody fragment

<400> SEQUENCE: 56

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn His Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: modified antibody fragment

<400> SEQUENCE: 57

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Asn Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 58
<211> LENGTH: 112
<212> TYPE: PRT
<213> ORGANISM: Artificial Sequence
<220> FEATURE:
<223> OTHER INFORMATION: modified antibody fragment

<400> SEQUENCE: 58

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Thr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 59
<211> LENGTH: 112
<212> TYPE: PRT
<213> ORGANISM: Artificial Sequence
<220> FEATURE:
<223> OTHER INFORMATION: modified antibody fragment

<400> SEQUENCE: 59

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gln Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Ser Gln Asn
            85                  90                  95

Thr His Val Pro Pro Thr Phe Gly Gln Gly Thr Lys Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: modified antibody fragment

<400> SEQUENCE: 60

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ile Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Pro Thr Phe Gly Gln Gly Thr Lys Leu Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: modified antibody fragment

<400> SEQUENCE: 61

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Lys Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Pro Thr Phe Gly Gln Gly Thr Lys Leu Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: modified antibody fragment

<400> SEQUENCE: 62

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Leu Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: modified antibody fragment

<400> SEQUENCE: 63

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ser Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 64
<211> LENGTH: 112
<212> TYPE: PRT
<213> ORGANISM: Artificial Sequence
<220> FEATURE:
<223> OTHER INFORMATION: modified antibody fragment

<400> SEQUENCE: 64

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Trp Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Asn
                85                  90                  95

```
Thr His Val Pro Pro Thr Phe Gly Gln Gly Thr Lys Leu Glu Ile Lys
            100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: modified antibody fragment

<400> SEQUENCE: 65

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Tyr Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 66
<211> LENGTH: 112
<212> TYPE: PRT
<213> ORGANISM: Artificial Sequence
<220> FEATURE:
<223> OTHER INFORMATION: modified antibody fragment

<400> SEQUENCE: 66

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 67
<211> LENGTH: 115
<212> TYPE: PRT
<213> ORGANISM: Artificial Sequence
<220> FEATURE:
<223> OTHER INFORMATION: modified antibody fragment

<400> SEQUENCE: 67

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Glu Met His Trp Ile Arg Gln Pro Gly Lys Gly Leu Glu Trp Ile
        35                  40                  45

Gly Ala Ile Asn Pro Lys Thr Gly Asp Thr Ala Tyr Ser Gln Lys Phe
50                  55                  60

Lys Gly Arg Val Thr Leu Thr Ala Asp Lys Ser Ser Thr Ala Tyr
65                  70                  75                  80

Met Glu Leu Ser Ser Leu Thr Ser Glu Asp Thr Ala Val Tyr Tyr Cys
            85                  90                  95

Thr Arg Phe Tyr Ser Tyr Thr Tyr Trp Gly Arg Gly Thr Leu Val Thr
            100                 105                 110

Val Ser Ser
        115

<210> SEQ ID NO 68
<211> LENGTH: 112
<212> TYPE: PRT
<213> ORGANISM: Artificial Sequence
<220> FEATURE:
<223> OTHER INFORMATION: modified antibody fragment

<400> SEQUENCE: 68

Asp Ile Val Met Thr Gln Ser Pro Leu Ser Leu Pro Val Thr Pro Gly
1               5                   10                  15

Gln Pro Ala Ser Ile Ser Cys Arg Ala Ser Arg Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
            85                  90                  95

Thr His Val Pro Pro Thr Phe Gly Arg Gly Thr Lys Leu Glu Ile Lys
            100                 105                 110

<210> SEQ ID NO 69
<211> LENGTH: 115
<212> TYPE: PRT
<213> ORGANISM: Artificial Sequence
<220> FEATURE:
<223> OTHER INFORMATION: modified antibody fragment

<400> SEQUENCE: 69

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Gly Glu Gly Leu Glu Trp Ile
        35                  40                  45

Gly Ala Ile Asp Pro Lys Thr Gly Asp Thr Ala Tyr Ser Gln Ser Phe
50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
            85                  90                  95
```

```
Thr Arg Phe Tyr Ser Tyr Thr Tyr Trp Gly Gln Gly Thr Leu Val Thr
                100                 105                 110

Val Ser Ser
        115

<210> SEQ ID NO 70
<211> LENGTH: 112
<212> TYPE: PRT
<213> ORGANISM: Artificial Sequence
<220> FEATURE:
<223> OTHER INFORMATION: modified antibody fragment

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 71
<211> LENGTH: 115
<212> TYPE: PRT
<213> ORGANISM: Artificial Sequence
<220> FEATURE:
<223> OTHER INFORMATION: modified antibody fragment

<400> SEQUENCE: 71

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Gly Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 72
<211> LENGTH: 112
<212> TYPE: PRT
<213> ORGANISM: Artificial Sequence
<220> FEATURE:
<223> OTHER INFORMATION: modified antibody fragment
```

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 73
<211> LENGTH: 112
<212> TYPE: PRT
<213> ORGANISM: Artificial Sequence
<220> FEATURE:
<223> OTHER INFORMATION: modified antibody fragment

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

<210> SEQ ID NO 74
<211> LENGTH: 330
<212> TYPE: PRT
<213> ORGANISM: homo sapiens

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
                    85                  90                  95
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 326
<212> TYPE: PRT
<213> ORGANISM: homo sapiens

<400> SEQUENCE: 75

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125
```

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 76
<211> LENGTH: 377
<212> TYPE: PRT
<213> ORGANISM: homo sapiens

<400> SEQUENCE: 76

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

-continued

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
370                 375

<210> SEQ ID NO 77
<211> LENGTH: 327
<212> TYPE: PRT
<213> ORGANISM: homo sapiens

<400> SEQUENCE: 77

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe 165                 170                 175
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 78
<211> LENGTH: 374
<212> TYPE: PRT
<213> ORGANISM: homo sapiens

<400> SEQUENCE: 78

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

```
Thr Leu Ser Cys Glu Thr Lys Leu Leu Gln Arg Pro Gly Leu Gln
    210                 215                 220
Leu Tyr Phe Ser Phe Tyr Met Gly Ser Lys Thr Leu Arg Gly Arg Asn
225                 230                 235                 240
Thr Ser Ser Glu Tyr Gln Ile Leu Thr Ala Arg Arg Glu Asp Ser Gly
                245                 250                 255
Leu Tyr Trp Cys Glu Ala Ala Thr Glu Asp Gly Asn Val Leu Lys Arg
                260                 265                 270
Ser Pro Glu Leu Glu Leu Gln Val Leu Gly Leu Gln Leu Pro Thr Pro
            275                 280                 285
Val Trp Phe His Val Leu Phe Tyr Leu Ala Val Gly Ile Met Phe Leu
290                 295                 300
Val Asn Thr Val Leu Trp Val Thr Ile Arg Lys Glu Leu Lys Arg Lys
305                 310                 315                 320
Lys Lys Trp Asp Leu Glu Ile Ser Leu Asp Ser Gly His Glu Lys Lys
                325                 330                 335
Val Ile Ser Ser Leu Gln Glu Asp Arg His Leu Glu Glu Glu Leu Lys
            340                 345                 350
Cys Gln Glu Gln Lys Glu Glu Gln Leu Gln Glu Gly Val His Arg Lys
            355                 360                 365
Glu Pro Gln Gly Ala Thr
            370

<210> SEQ ID NO 79
<211> LENGTH: 316
<212> TYPE: PRT
<213> ORGANISM: homo sapiens

<400> SEQUENCE: 79

Met Thr Met Glu Thr Gln Met Ser Gln Asn Val Cys Pro Arg Asn Leu
1               5                   10                  15
Trp Leu Leu Gln Pro Leu Thr Val Leu Leu Leu Leu Ala Ser Ala Asp
            20                  25                  30
Ser Gln Ala Ala Pro Pro Lys Ala Val Leu Lys Leu Glu Pro Pro Trp
        35                  40                  45
Ile Asn Val Leu Gln Glu Asp Ser Val Thr Leu Thr Cys Gln Gly Ala
50                  55                  60
Arg Ser Pro Glu Ser Asp Ser Ile Gln Trp Phe His Asn Gly Asn Leu
65                  70                  75                  80
Ile Pro Thr His Thr Gln Pro Ser Tyr Arg Phe Lys Ala Asn Asn Asn
                85                  90                  95
Asp Ser Gly Glu Tyr Thr Cys Gln Thr Gly Gln Thr Ser Leu Ser Asp
            100                 105                 110
Pro Val His Leu Thr Val Leu Ser Glu Trp Leu Val Leu Gln Thr Pro
        115                 120                 125
His Leu Glu Phe Gln Glu Gly Glu Thr Ile Met Leu Arg Cys His Ser
    130                 135                 140
Trp Lys Asp Lys Pro Leu Val Lys Val Thr Phe Phe Gln Asn Gly Lys
145                 150                 155                 160
Ser Gln Lys Phe Ser His Leu Asp Pro Thr Phe Ser Ile Pro Gln Ala
                165                 170                 175
Asn His Ser His Ser Gly Asp Tyr His Cys Thr Gly Asn Ile Gly Tyr
            180                 185                 190
Thr Leu Phe Ser Ser Lys Pro Val Thr Ile Thr Val Gln Val Pro Ser
        195                 200                 205
```

Met Gly Ser Ser Ser Pro Met Gly Val Ile Val Ala Val Ile Ala
     210                 215                 220
Thr Ala Val Ala Ala Ile Val Ala Ala Val Val Ala Leu Ile Tyr Cys
225                 230                 235                 240
Arg Lys Lys Arg Ile Ser Ala Asn Ser Thr Asp Pro Val Lys Ala Ala
                245                 250                 255
Gln Phe Glu Pro Pro Gly Arg Gln Met Ile Ala Ile Arg Lys Arg Gln
            260                 265                 270
Leu Glu Glu Thr Asn Asn Asp Tyr Glu Thr Ala Asp Gly Gly Tyr Met
        275                 280                 285
Thr Leu Asn Pro Arg Ala Pro Thr Asp Asp Lys Asn Ile Tyr Leu
    290                 295                 300
Thr Leu Pro Pro Asn Asp His Val Asn Ser Asn Asn
305                 310                 315

<210> SEQ ID NO 80
<211> LENGTH: 291
<212> TYPE: PRT
<213> ORGANISM: homo sapiens

<400> SEQUENCE: 80

Met Gly Ile Leu Ser Phe Leu Pro Val Leu Ala Thr Glu Ser Asp Trp
1               5                   10                  15
Ala Asp Cys Lys Ser Pro Gln Pro Trp Gly His Met Leu Leu Trp Thr
                20                  25                  30
Ala Val Leu Phe Leu Ala Pro Val Ala Gly Thr Pro Ala Ala Pro Pro
            35                  40                  45
Lys Ala Val Leu Lys Leu Glu Pro Gln Trp Ile Asn Val Leu Gln Glu
        50                  55                  60
Asp Ser Val Thr Leu Thr Cys Arg Gly Thr His Ser Pro Glu Ser Asp
65                  70                  75                  80
Ser Ile Gln Trp Phe His Asn Gly Asn Leu Ile Pro Thr His Thr Gln
                85                  90                  95
Pro Ser Tyr Arg Phe Lys Ala Asn Asn Asn Asp Ser Gly Glu Tyr Thr
            100                 105                 110
Cys Gln Thr Gly Gln Thr Ser Leu Ser Asp Pro Val His Leu Thr Val
        115                 120                 125
Leu Ser Glu Trp Leu Val Leu Gln Thr Pro His Leu Glu Phe Gln Glu
    130                 135                 140
Gly Glu Thr Ile Val Leu Arg Cys His Ser Trp Lys Asp Lys Pro Leu
145                 150                 155                 160
Val Lys Val Thr Phe Phe Gln Asn Gly Lys Ser Lys Lys Phe Ser Arg
                165                 170                 175
Ser Asp Pro Asn Phe Ser Ile Pro Gln Ala Asn His Ser His Ser Gly
            180                 185                 190
Asp Tyr His Cys Thr Gly Asn Ile Gly Tyr Thr Leu Tyr Ser Ser Lys
        195                 200                 205
Pro Val Thr Ile Thr Val Gln Ala Pro Ser Ser Ser Pro Met Gly Ile
    210                 215                 220
Ile Val Ala Val Val Thr Gly Ile Ala Val Ala Ala Ile Val Ala Ala
225                 230                 235                 240
Val Val Ala Leu Ile Tyr Cys Arg Lys Lys Arg Ile Ser Ala Asn Pro
                245                 250                 255
Thr Asn Pro Asp Glu Ala Asp Lys Val Gly Ala Glu Asn Thr Ile Thr

```
                260                 265                 270
Tyr Ser Leu Leu Met His Pro Asp Ala Leu Glu Glu Pro Asp Asp Gln
            275                 280                 285

Asn Arg Ile
        290

<210> SEQ ID NO 81
<211> LENGTH: 254
<212> TYPE: PRT
<213> ORGANISM: homo sapiens

<400> SEQUENCE: 81

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 82
<211> LENGTH: 233
<212> TYPE: PRT
<213> ORGANISM: homo sapiens

<400> SEQUENCE: 82

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
```

```
                    35                      40                      45
Gly Ala Tyr Ser Pro Glu Asp Asn Ser Thr Gln Trp Phe His Asn Glu
            50                      55                  60

Ser Leu Ile Ser Ser Gln Ala Ser Ser Tyr Phe Ile Asp Ala Ala Thr
65                      70                  75                      80

Val Asn Asp Ser Gly Glu Tyr Arg Cys Gln Thr Asn Leu Ser Thr Leu
                85                      90                  95

Ser Asp Pro Val Gln Leu Glu Val His Ile Gly Trp Leu Leu Leu Gln
                100                     105             110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
            130                 135                 140

Gly Lys Asp Arg Lys Tyr Phe His His Asn Ser Asp Phe His Ile Pro
145                     150                 155                 160

Lys Ala Thr Leu Lys Asp Ser Gly Ser Tyr Phe Cys Arg Gly Leu Val
                165                     170                 175

Gly Ser Lys Asn Val Ser Ser Glu Thr Val Asn Ile Thr Ile Thr Gln
                180                     185                 190

Gly Leu Ala Val Ser Thr Ile Ser Ser Phe Ser Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile
225                 230
```

GPC3-TARGETING THERAPEUTIC AGENT WHICH IS ADMINISTERED TO PATIENT FOR WHOM THE GPC3-TARGETING THERAPEUTIC AGENT IS EFFECTIVE

CROSS-REFERENCE TO RELATED APPLICATIONS

This application is a U.S. National Phase of PCT Application No. PCT/JP2016/069493, filed Jun. 30, 2016, which claims the benefit of Japanese Patent Application No. 2015-133076, filed Jul. 1, 2015, each of which is incorporated herein by reference in its entirety.

REFERENCE TO SEQUENCE LISTING SUBMITTED ELECTRONICALLY

The content of the electronically submitted sequence listing (Name: 6663_0055_Sequence_Listing.txt; Size: 76.5 kilobytes; and Date of Creation: Dec. 29, 2017) filed with the application is incorporated herein by reference in its entirety.

TECHNICAL FIELD

The present invention provides a method for determining the efficacy of a GPC3-targeting therapeutic agent for cancer in a patient, and a GPC3-targeting therapeutic agent or a preparation which is to be administered to (only) a patient for whom it has been determined that the GPC3-targeting therapeutic agent is effective.

BACKGROUND ART

Hepatocellular carcinoma is reportedly the fifth leading cause of cancer deaths worldwide, accounting for approximately 600,000 deaths each year (Non Patent Literature 1). Most patients with hepatocellular carcinoma die within 1 year after being diagnosed with the disease. Unfortunately, hepatocellular carcinoma cases are frequently diagnosed at a late stage which rarely responds to curative therapies. Still, medical procedures including chemotherapy, chemoembolization, ablation, and proton beam therapy are insufficiently effective for such patients. Many patients manifest the recurrence of the disease with vascular invasion and multiple intrahepatic metastases, which rapidly progresses to the advanced stage, and their 5-year survival rates are only 7% (Non Patent Literature 2). Patients with hepatocellular carcinoma amenable to the resection of local nodule have relatively good prognosis, though their 5-year survival rates still remain at a level of 15% and 39% (Non Patent Literature 3). Thus, there has been a demand in the art for novel therapy for such a malignant disease hepatocellular carcinoma.

Hepatocellular carcinoma is reportedly responsible for more than 90% of primary liver cancer cases in Japan. Medical methods for treating such hepatocellular carcinoma include, for example, chemotherapy-based TAE (transcatheter arterial embolization) therapy, which involves inducing the selective necrosis of the hepatocellular carcinoma by the injection of a mixture of an oil-based contrast medium (Lipiodol), an anticancer agent, and an obstructing substance (Gelfoam) into the hepatic artery (which serves as a nutrient supply pathway to the tumor) resulting in the obstruction of the nutrient artery. In addition, invasive approaches are used, such as percutaneous ethanol injection, percutaneous microwave coagulation therapy, and radiofrequency ablation. Also, clinical trials have been conducted on systemic chemotherapy using chemotherapeutic agents such as 5-FU (fluorouracil), UFT (uracil-tegafur), MMC (mitomycin C), DHAD (mitoxantrone), ADR (adriamycin), EPI (epirubicin), and CDDP (cisplatin) either alone or in combination with IFN (interferon) (Non Patent Literature 4).

Meanwhile, an orally active form of sorafenib (Nexavar, BAY43-9006) has been approved, which is more advantageously effective than the chemotherapeutic agents described above in such a way that this agent blocks the growth of cancer cells by inhibiting Raf kinase in Raf/MEK/ERK signal transduction while the agent exerts antiangiogenic effects by targeting VEGFR-2, VEGFR-3, and PDGFR-β tyrosine kinases. The efficacy of sorafenib has been studied in two phase III multicenter placebo-controlled trials (Sorafenib HCC Assessment Randomized Protocol (SHARP) trial and Asia-Pacific trial) targeting advanced hepatocellular carcinoma. Sorafenib was confirmed to prolong survival durations, with HR of 0.68, in both of these trials. In the SHARP trial, sorafenib prolonged the survival duration to 10.7 months versus 7.9 months with the placebo. In the Asian trial, sorafenib prolonged the survival duration to 6.5 months versus 4.2 months with the placebo. This agent, however, had a low objective response rate and showed no prolongation of a time to symptomatic progression, though the agent prolonged a time to tumor radiological progression (5.5 months versus 2.8 months in the European and American trial and 2.8 months versus 1.4 months in the Asian trial). The Asian cohorts exhibited a short duration of life prolongation, which is probably because their treatments were started at a slightly later stage during the disease process in the Asian region compared with Europe and the United States (Non Patent Literatures 5 and 6).

As liver cancer progresses, its specific symptoms associated with liver dysfunction are generally observed, such as anorexia, weight loss, general malaise, palpable right hypochondrial mass, right hypochondrial pain, sense of abdominal fullness, fever, and jaundice. The chemotherapeutic agents (e.g., sorafenib), however, have complications to be overcome, including their inherent adverse reactions such as diarrhea or constipation, anemia, suppression of the immune system to cause infection or sepsis (with lethal severity), hemorrhage, cardiac toxicity, hepatic toxicity, renal toxicity, anorexia, and weight loss.

Although particular early-stage symptoms are not initially observed in liver cancer, its specific symptoms associated with liver dysfunction, such as anorexia, weight loss, general malaise, palpable right hypochondrial mass, right hypochondrial pain, sense of abdominal fullness, fever, and jaundice, are generally observed with progression of the liver cancer. Enhancement in such symptoms caused by use of the chemotherapeutic agents described above are clinically observed. For example, anorexia in a patient with detectable liver cancer cells and symptoms such as weight loss associated with or independent of the anorexia may be more enhanced by the administration of the chemotherapeutic agents to the patient than without the use of the chemotherapeutic agents. In some cases, the use of the chemotherapeutic agents must be discontinued for the patient having such symptoms. These enhanced symptoms are impediments to treatments with the chemotherapeutic agents. Thus, there has been a demand for the establishment of better treatment methods from the viewpoint of, for example, improving therapeutic effects or improving QOL of patients to be treated.

Glypican 3 (GPC3) is frequently expressed at a high level in liver cancer and as such, seems to be useful in the identification of its functions in liver cancer or as a therapeutic or diagnostic target of liver cancer.

Under the circumstances described above, therapeutic agents are under development with GPC3 as a therapeutic target of liver cancer. A therapeutic agent for liver cancer comprising an anti-GPC3 antibody as an active ingredient has been developed, the antibody exerting antibody-dependent cellular cytotoxicity (hereinafter, referred to as "ADCC") activity and/or complement-dependent cytotoxicity (hereinafter, referred to as "CDC") activity against cells expressing GPC3 (Patent Literature 1). Also, a GPC3-targeting therapeutic agent comprising a humanized anti-GPC3 antibody having ADCC activity and CDC activity as an active ingredient has been developed (Patent Literature 2). Further, GPC3-targeting therapeutic agents have been developed, which comprise a humanized anti-GPC3 antibody with enhanced ADCC activity (Patent Literatures 3 and 4) or an anti-GPC3 antibody having ADCC activity and CDC activity as well as improved plasma kinetics (Patent Literature 5). These anti-GPC3 antibodies in combination therapy with the chemotherapeutic agents such as sorafenib have been found to attenuate the adverse reactions, for example, brought about by the sole therapy of the chemotherapeutic agents (e.g., sorafenib) and also found to exhibit synergistic effects based on these agents (Patent Literature 6). Accordingly, excellent methods for treating liver cancer are in the process of being established by using GPC3-targeting therapeutic agents as the base therapy from the viewpoint of, for example, improving therapeutic effects or improving QOL of patients to be treated.

Meanwhile, GPC3-targeting methods for diagnosing liver cancer are also under development. GPC3 is known to be processed, at its particular site, by convertase, phospholipase D, Notum, or an unidentified mechanism during or after expression on cell surface (Non Patent Literatures 7 and 8). By use of such a phenomenon, a diagnostic agent or a diagnostic method for liver cancer has been developed, which involves an antibody binding to an epitope in a soluble form of GPC3 secreted into the plasma of a patient after processing (Patent Literature 7). Also, a diagnostic agent or a diagnostic method for liver cancer has been developed, which involves an antibody binding to an epitope in an anchored form of GPC3 still existing on cell surface after processing in a tissue preparation or the like isolated from a patient (Patent Literature 8). These diagnostic agents or diagnostic methods, however, are directed to detecting the presence of liver cancer in a patient to be tested. Neither a method for identifying a patient for which the efficacy of a GPC3-targeting therapeutic agent can be expected nor a method for determining the continuation of the administration of a GPC3-targeting therapeutic agent to a patient treated with the GPC3-targeting therapeutic agent has been known yet.

The relationship between results of immunostaining tumor tissue preparations by immunohistochemical staining using anti-GPC3 antibodies and the therapeutic effects of GPC3-targeting therapeutic agents has been studied in the phase I clinical trials of GPC3 sequence-derived peptide vaccines or humanized anti-GPC3 antibodies, but has not yet reached evident conclusion, probably, due to low prediction accuracy (Non Patent Literatures 9, 10, and 11).

References cited herein are as listed below. The contents described in these literatures are incorporated herein by reference in their entirety. It should be noted that none of these literatures are admitted to be the prior art to the present invention.

CITATION LIST

Patent Literature

Patent Literature 1: WO2003/000883
Patent Literature 2: WO2006/006693
Patent Literature 3: WO2006/046751
Patent Literature 4: WO2007/047291
Patent Literature 5: WO2009/041062
Patent Literature 6: WO2009/122667
Patent Literature 7: WO2004/038420
Patent Literature 8: WO2009/116659

Non Patent Literature

Non Patent Literature 1: Llovet J M, Burroughs A, Bruix J; Lancet (2003), 362, 1907-17
Non Patent Literature 2: Bosch F X, Ribes J, Cleries R; Gastroenterology (2004), 127, S5-16
Non Patent Literature 3: Takenaka K, Kawahara N, Yamamoto K, Kajiyama K, Maeda T, Itasaka H, Shirabe K, Nishizaki T, Yanaga K, Sugimachi K; Arch Surg (1996), 131, 71-6
Non Patent Literature 4: Yeo W, Mok T S, Zee B, Leung T W, Lai P B, Lau W Y, Koh J, Mo F K, Yu S C, Chan A T, Hui P, Ma B, Lam K C, Ho W M, Wong H T, Tang A, Johnson P J; J Natl Cancer Inst (2005), 97, 1532-8
Non Patent Literature 5: Llovet J, Ricci S, Mazzaferro V, Hilgard P, Gane E, et al. Sorafenib in advanced hepatocellular carcinoma. New Eng. J. Med. (2008) 359, 378-90
Non Patent Literature 6: Cheng A L, Chen Z, Tsao C J, Qin S, Kim J S, et al. Efficacy and safety of sorefanib in patients in the Asia-Pacific region with advanced hepatocellular carcinoma: a phase III randomized, double-blind, placebo-controlled trial. Lancet Oncol. (2009) 10, 25-34
Non Patent Literature 7: De Cat B, Muyldermans S-Y, Coomans C, Degeest G, Vanderschueren B, et al. Processing by proprotein convertases is required for glypican-3 modulation of cell survival, Wnt signaling, and gastrulation movements. J. Cell. Biol. (2003) 163, 625-635
Non Patent Literature 8: Traister A, Shi W and Filmus J. Mammalian Notum induces the release of glypicans and other GPI-anchored proteins from the cell surface. Biochem. J. (2008) 410, 503-511
Non Patent Literature 9: Sawada Y, Yoshikawa T, Nobuoka D, Shirakawa H, Kuronuma T et al. Phase I trial of a glypican-3-derived peptide vaccine for advanced hepatocellular carcinoma: Immunologic evidence and potential for improving overall survival. Clin. Cancer Res. (2012) 18, 3686-3696
Non Patent Literature 10: Zhu A. X, Gold P. J, El-Koueiry A. B, Abrams T. A, Morikawa H et al. First-in-man phase I study of GC33, a novel recombinant humanized antibody against glypican-3, in patients with advanced hepatocellular carcinoma. Clin. Cancer Res. (2013) 19, 920-928
Non Patent Literature 11: Ikeda M, Ohkawa S, Okusaka T, Mitsunaga S, Kobayashi S, et al. Japanese phase I study of GC33, a humanized antibody against glypican-3 for advanced hepatocellular carcinoma. Cancer Sci. (2014) 105, 455-462

SUMMARY OF INVENTION

Technical Problem

The present invention has been made in light of the situations as described above, and an object of the present invention is to provide a method for determining the efficacy of a GPC3-targeting therapeutic agent for a liver cancer patient. Another object of the present invention is to provide a GPC3-targeting therapeutic agent or a preparation which is to be administered to (only) a patient for whom it has been determined that the GPC3-targeting therapeutic agent is effective.

Solution to Problem

The present inventors have conducted diligent studies under the situations as described above and measured the expression level of GPC3 in a biological sample isolated from a patient before the start of administration of a GPC3-targeting therapeutic agent to thereby found only the expression level of GPC3 per tumor cell exhibits high correlation with the efficacy of the GPC3-targeting therapeutic agent for the patient. The present inventors have consequently created a method wherein it has been determined that the GPC3-targeting therapeutic agent is effective when the expression level of GPC3 per tumor cell is a predetermined value. The present inventors have also created a GPC3-targeting therapeutic agent or a preparation which is to be administered to (only) a patient for whom it has been determined that the GPC3-targeting therapeutic agent is effective in this way.

More specifically, the present invention provides the following aspects:

[1] A method for determining the efficacy of a GPC3-targeting therapeutic agent for liver cancer in a patient, the method comprising measuring an expression level of GPC3 per tumor cell in a biological sample isolated from the patient.

[2] The method according to [1], further comprising determining that the GPC3-targeting therapeutic agent is effective when the expression level of GPC3 per tumor cell in the biological sample is a predetermined value.

[3] The method according to [1] or [2], wherein the biological sample is a liver cancer tissue sample.

[4] The method according to any of [1] to [3], wherein the expression level of GPC3 per tumor cell is indicated by IQD cell score.

[5] The method according to any of [1] to [4], wherein the GPC3-targeting therapeutic agent is administered to achieve a blood trough level of 200 μg/ml or higher in the patient.

[6] The method according to any of [1] to [5], wherein the GPC3-targeting therapeutic agent is a therapeutic agent comprising an anti-GPC3 antibody as an active ingredient.

[7] The method according to [6], wherein the anti-GPC3 antibody is an antibody having antibody-dependent cellular cytotoxicity (ADCC) activity and/or complement-dependent cytotoxicity (CDC) activity.

[8] The method according to [6] or [7], wherein the anti-GPC3 antibody is an anti-GPC3 chimeric antibody or a humanized anti-GPC3 antibody comprising any of the following (1) to (5):

(1) heavy chain CDR1, heavy chain CDR2, and heavy chain CDR3 represented by SEQ ID NO: 4, SEQ ID NO: 5, and SEQ ID NO: 6, respectively, and light chain CDR1, light chain CDR2, and light chain CDR3 represented by SEQ ID NO: 7, SEQ ID NO: 8, and SEQ ID NO: 9, respectively;

(2) heavy chain CDR1, heavy chain CDR2, and heavy chain CDR3 represented by SEQ ID NO: 12, SEQ ID NO: 13, and SEQ ID NO: 14, respectively, and light chain CDR1, light chain CDR2, and light chain CDR3 represented by SEQ ID NO: 15, SEQ ID NO: 16, and SEQ ID NO: 17, respectively;

(3) heavy chain CDR1, heavy chain CDR2, and heavy chain CDR3 represented by SEQ ID NO: 20, SEQ ID NO: 21, and SEQ ID NO: 22, respectively, and light chain CDR1, light chain CDR2, and light chain CDR3 represented by SEQ ID NO: 23, SEQ ID NO: 24, and SEQ ID NO: 25, respectively;

(4) heavy chain CDR1, heavy chain CDR2, and heavy chain CDR3 represented by SEQ ID NO: 28, SEQ ID NO: 29, and SEQ ID NO: 30, respectively, and light chain CDR1, light chain CDR2, and light chain CDR3 represented by SEQ ID NO: 31, SEQ ID NO: 32, and SEQ ID NO: 33, respectively; and (5) heavy chain CDR1, heavy chain CDR2, and heavy chain CDR3 represented by SEQ ID NO: 36, SEQ ID NO: 37, and SEQ ID NO: 38, respectively, and light chain CDR1, light chain CDR2, and light chain CDR3 represented by SEQ ID NO: 39, SEQ ID NO: 40, and SEQ ID NO: 41, respectively.

[9] The method according to any of [6] to [8], wherein the anti-GPC3 antibody is an antibody comprising any of the following (1) to (6):

(1) a heavy chain variable region selected from the group of heavy chain variable regions represented by SEQ ID NO: 44, SEQ ID NO: 45, SEQ ID NO: 46, SEQ ID NO: 47, SEQ ID NO: 48, SEQ ID NO: 49, and SEQ ID NO: 50, and a light chain variable region represented by SEQ ID NO: 51;

(2) a heavy chain variable region selected from the group of heavy chain variable regions represented by SEQ ID NO: 44, SEQ ID NO: 45, SEQ ID NO: 46, SEQ ID NO: 47, SEQ ID NO: 48, SEQ ID NO: 49, and SEQ ID NO: 50, and a light chain variable region selected from the group of light chain variable regions represented by SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, and SEQ ID NO: 66;

(3) a heavy chain variable region represented by SEQ ID NO: 67 and a light chain variable region represented by SEQ ID NO: 68;

(4) a heavy chain variable region represented by SEQ ID NO: 69 and a light chain variable region represented by SEQ ID NO: 70;

(5) a heavy chain variable region represented by SEQ ID NO: 71 and a light chain variable region represented by SEQ ID NO: 72; and (6) a heavy chain variable region represented by SEQ ID NO: 71 and a light chain variable region represented by SEQ ID NO: 73.

[10] The method according to [6], wherein the anti-GPC3 antibody is an antibody conjugated with a cytotoxic substance.

[11] The method according to any of [1] to [10], wherein the GPC3-targeting therapeutic agent is administered concurrently with or separately from one or two or more anticancer agent(s).

[12] The method according to [11], wherein the anticancer agent is sorafenib.

[13] A drug comprising a GPC3-targeting therapeutic agent as an active ingredient, wherein the drug is to be administered to a patient having a predetermined value of an expression level of GPC3 per tumor cell in a biological sample isolated from the patient.

[14] The drug according to [13], wherein the patient is a patient for whom it has been determined that the expression level of GPC3 per tumor cell in the biological sample isolated from the patient is the predetermined value.

[15] The drug according to [13], wherein the patient is a patient for whom it has been determined that the GPC3-targeting therapeutic agent is effective on the ground that the expression level of GPC3 per tumor cell in the biological sample isolated from the patient is the predetermined value.

[16] The drug according to any of [13] to [15], wherein the expression level of GPC3 per tumor cell is indicated by IQD cell score.

[17] The drug according to any of [13] to [16], wherein the patient is a liver cancer patient.

[18] The drug according to [17], wherein the liver cancer is liver cancer for which the GPC3-targeting therapeutic agent is effective.

[19] The drug according to [18], wherein the liver cancer for which the GPC3-targeting therapeutic agent is effective is characterized in that the expression level of GPC3 indicated by IQD cell score in the biological sample isolated from the patient is the predetermined value.

[20] The drug according to any of [13] to [19], wherein the biological sample is a liver cancer tissue sample.

[21] The drug according to any of [13] to [20], wherein the GPC3-targeting therapeutic agent is administered to achieve a blood trough level of 200 μg/ml or higher in the patient.

[22] The drug according to any of [13] to [21], wherein the GPC3-targeting therapeutic agent is a therapeutic agent comprising an anti-GPC3 antibody as an active ingredient.

[23] The drug according to [22], wherein the anti-GPC3 antibody is an antibody having antibody-dependent cellular cytotoxicity (ADCC) activity and/or complement-dependent cytotoxicity (CDC) activity.

[24] The drug according to [22] or [23], wherein the anti-GPC3 antibody is an anti-GPC3 chimeric antibody or a humanized anti-GPC3 antibody comprising any of the following (1) to (5):
(1) heavy chain CDR1, heavy chain CDR2, and heavy chain CDR3 represented by SEQ ID NO: 4, SEQ ID NO: 5, and SEQ ID NO: 6, respectively, and light chain CDR1, light chain CDR2, and light chain CDR3 represented by SEQ ID NO: 7, SEQ ID NO: 8, and SEQ ID NO: 9, respectively;
(2) heavy chain CDR1, heavy chain CDR2, and heavy chain CDR3 represented by SEQ ID NO: 12, SEQ ID NO: 13, and SEQ ID NO: 14, respectively, and light chain CDR1, light chain CDR2, and light chain CDR3 represented by SEQ ID NO: 15, SEQ ID NO: 16, and SEQ ID NO: 17, respectively;
(3) heavy chain CDR1, heavy chain CDR2, and heavy chain CDR3 represented by SEQ ID NO: 20, SEQ ID NO: 21, and SEQ ID NO: 22, respectively, and light chain CDR1, light chain CDR2, and light chain CDR3 represented by SEQ ID NO: 23, SEQ ID NO: 24, and SEQ ID NO: 25, respectively;
(4) heavy chain CDR1, heavy chain CDR2, and heavy chain CDR3 represented by SEQ ID NO: 28, SEQ ID NO: 29, and SEQ ID NO: 30, respectively, and light chain CDR1, light chain CDR2, and light chain CDR3 represented by SEQ ID NO: 31, SEQ ID NO: 32, and SEQ ID NO: 33, respectively; and
(5) heavy chain CDR1, heavy chain CDR2, and heavy chain CDR3 represented by SEQ ID NO: 36, SEQ ID NO: 37, and SEQ ID NO: 38, respectively, and light chain CDR1, light chain CDR2, and light chain CDR3 represented by SEQ ID NO: 39, SEQ ID NO: 40, and SEQ ID NO: 41, respectively.

[25] The drug according to any of [22] to [24], wherein the anti-GPC3 antibody is an antibody comprising any of the following (1) to (6):
(1) a heavy chain variable region selected from the group of heavy chain variable regions represented by SEQ ID NO: 44, SEQ ID NO: 45, SEQ ID NO: 46, SEQ ID NO: 47, SEQ ID NO: 48, SEQ ID NO: 49, and SEQ ID NO: 50, and a light chain variable region represented by SEQ ID NO: 51;
(2) a heavy chain variable region selected from the group of heavy chain variable regions represented by SEQ ID NO: 44, SEQ ID NO: 45, SEQ ID NO: 46, SEQ ID NO: 47, SEQ ID NO: 48, SEQ ID NO: 49, and SEQ ID NO: 50, and a light chain variable region selected from the group of light chain variable regions represented by SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, and SEQ ID NO: 66;
(3) a heavy chain variable region represented by SEQ ID NO: 67 and a light chain variable region represented by SEQ ID NO: 68;
(4) a heavy chain variable region represented by SEQ ID NO: 69 and a light chain variable region represented by SEQ ID NO: 70;
(5) a heavy chain variable region represented by SEQ ID NO: 71 and a light chain variable region represented by SEQ ID NO: 72; and
(6) a heavy chain variable region represented by SEQ ID NO: 71 and a light chain variable region represented by SEQ ID NO: 73.

[26] The drug according to [22], wherein the anti-GPC3 antibody is an antibody conjugated with a cytotoxic substance.

[27] The drug according to any of [13] to [26], further comprising one or two or more anticancer agent(s) as an active ingredient.

[28] The drug according to any of [13] to [26], wherein the drug is administered concurrently with or separately from one or two or more anticancer agent(s).

[29] The drug according to [27] or [28], wherein the anticancer agent is sorafenib.

[30] A method for selecting a patient for which a GPC3-targeting therapeutic agent is effective from a patient group with liver cancer, the method comprising the step of determining that the GPC3-targeting therapeutic agent is effective for a patient when the expression level of GPC3 per tumor cell in a biological sample isolated from the patient is a predetermined value.

[31] The method according to [30], wherein the GPC3-targeting therapeutic agent is a therapeutic agent comprising an anti-GPC3 antibody as an active ingredient.

[32] A kit for determining the efficacy of a GPC3-targeting therapeutic agent for liver cancer in a patient, the kit comprising a reagent for measuring an expression level of GPC3 per tumor cell in a biological sample isolated from the patient.

[33] The kit according to [32], further comprising an instruction stating that it is determined that the GPC3-targeting therapeutic agent is effective when the expression level of GPC3 per tumor cell in the biological sample is a predetermined value.

[34] The kit according to [32] or [33], further comprising the GPC3-targeting therapeutic agent.

[35] The kit according to any of [32] to [34], wherein the GPC3-targeting therapeutic agent is a therapeutic agent comprising an anti-GPC3 antibody as an active ingredient.

[36] A preparation comprising a GPC3-targeting therapeutic agent and an instruction stating that the GPC3-targeting therapeutic agent is administered to a patient having a predetermined value of an expression level of GPC3 per tumor cell in a biological sample isolated from the patient.

[37] The preparation according to [36], wherein the GPC3-targeting therapeutic agent is a therapeutic agent comprising an anti-GPC3 antibody as an active ingredient.

[38] A kit for the treatment of liver cancer comprising the following factors:
(1) a GPC3-targeting therapeutic agent; and
(2) an instruction stating that it is determined that the GPC3-targeting therapeutic agent is effective for a patient having a predetermined value of an expression level of GPC3 per tumor cell in a biological sample isolated from the patient.

[39] The kit according to [38], wherein the GPC3-targeting therapeutic agent is a therapeutic agent comprising an anti-GPC3 antibody as an active ingredient.

According to the present invention, whether a GPC3-targeting therapeutic agent is effective for a patient can be determined conveniently and accurately. This can improve the effects of the GPC3-targeting therapeutic agent and improve QOL of a patient to be treated. As a result, the better treatment of cancer is achieved.

BRIEF DESCRIPTION OF DRAWINGS

FIG. 7A shows the analysis of a group in which the GPC3-IHC membrane H score was larger than the median value. FIG. 7B shows the analysis of a group in which the GPC3-IHC cytoplasm H score was larger than the median value. FIG. 7C shows the analysis of a group in which the GPC3-IQD intensity score was larger than the median value.

DESCRIPTION OF EMBODIMENTS

Definitions

Figure 1:
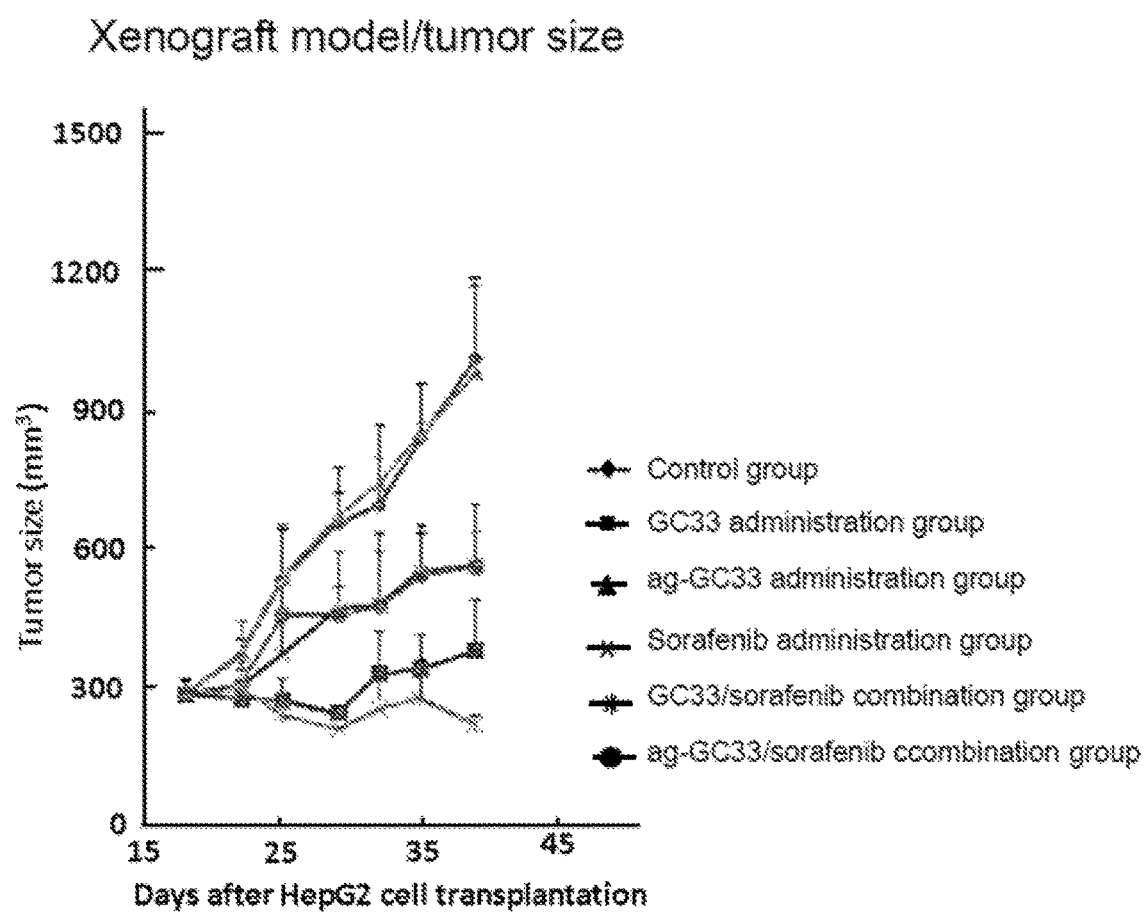
FIG. 1 shows the relationship between therapeutic agent administration and a tumor size in mouse graft models using a human cell line HepG2 strongly expressing GPC3.

Chemical terms and technical terms used in relation to the present invention have meanings generally understood by those skilled in the art, unless otherwise defined herein.

Indefinite Article

In the present invention, the indefinite articles "a" and "an" refer to one or two or more (i.e., at least one) object(s) grammatically represented by the indefinite articles. For example, "a factor" means one factor or two or more factors.

Antibody

The "antibody" according to the present invention is not limited to the whole molecule of an antibody and may be a fragment of the antibody or a modified form of the antibody or the fragment. The antibody of the present invention also includes a bivalent antibody and a monovalent antibody. Examples of the antibody fragment include Fab, F(ab')2, Fv, Fab/c having one Fab and complete Fc, and single-chain Fv (scFv) containing H and L chain Fvs linked through an appropriate linker. Specifically, the antibody fragment is formed by the treatment of the antibody with an enzyme, for example, papain or pepsin, or is expressed in appropriate host cells after construction of a gene encoding the antibody fragment and subsequent transfer of this gene to an expression vector (see, for example, Co, M. S. et al., J. Immunol. (1994) 152, 2968-2976, Better, M. & Horwitz, A. H. Methods in Enzymology (1989) 178, 476-496, Academic Press, Inc., Plueckthun, A. & Skerra, A. Methods in Enzymology (1989) 178, 476-496, Academic Press, Inc., Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

The scFv is obtained by linking the H chain V region and the L chain V region of the antibody. In this scFv, the H chain V region and the L chain V region are linked via a linker, preferably a peptide linker (Huston, J. S. et al., Proc. Natl. Acad. Sci. U.S.A. (1988) 85, 5879-5883). The H chain V region and the L chain V region in the scFv may be derived from any of those described as the antibody in the present specification. For example, an arbitrary single-chain peptide composed of 12 to 19 amino acid residues is used as the peptide linker for linking the V regions.

A DNA encoding the scFv is obtained by using, as a template, each DNA moiety encoding the whole or desired amino acid sequence, in the sequences of a DNA encoding the H chain or the H chain V region of the antibody and a DNA encoding the L chain or the L chain V region of the antibody, and amplifying the template by PCR using a primer pair annealing to both ends thereof, followed by amplification by the combination of a DNA encoding the peptide linker moiety and a primer pair annealing thereto such that the both ends of the peptide linker are linked to the H chain and the L chain, respectively.

Once the scFv-encoding DNA is prepared, an expression vector containing the DNA, and a host transformed with the expression vector can be obtained according to routine methods. Also, the scFv can be obtained according to a routine method by using the host.

These antibody fragments can be expressed through the obtainment of their genes in the same way as above and produced by the host. The "antibody" according to the present invention also encompasses these antibody fragments.

The antibody used in the present invention may be a bispecific antibody. The bispecific antibody may be prepared by linking the HL pairs of two types of antibodies, or may be obtained by fusing hybridomas producing different monoclonal antibodies to prepare bispecific antibody-producing fusion cells. Alternatively, the bispecific antibody may be prepared by a genetic engineering approach.

Amino Acid

In the present specification, each amino acid is indicated by single-letter code or three-letter code, or both, as represented by, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, and Val/V.

Amino Acid Alteration

A method known in the art such as site-directed mutagenesis (Kunkel et al., Proc. Natl. Acad. Sci. USA (1985) 82, 488-492) or overlap extension PCR can be appropriately adopted for the alteration of an amino acid in the amino acid sequence of an antigen-binding molecule. Also, a plurality of methods known in the art can be adopted as methods for altering an amino acid to substitute the amino acid by an amino acid other than natural one (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

In the present specification, the term "and/or" used to represent amino acid alteration sites is meant to include every combination appropriately represented by "and" and "or". Specifically, for example, the phrase "amino acids at positions 43, 52, and/or 105 are substituted" includes the following variations of amino acid alteration: (a) position 43, (b) position 52, (c) position 105, (d) positions 43 and 52, (e) positions 43 and 105, (f) positions 52 and 105, and (g) positions 43, 52, and 105.

EU Numbering and Kabat Numbering

According to a method used in the present invention, amino acid positions assigned to antibody CDRs and FRs are defined according to the Kabat method (Sequences of Proteins of Immunological Interest, National Institute of Health, Bethesda, Md., 1987 and 1991). In the present specification, when the antigen-binding molecule is an antibody or an antigen-binding fragment, amino acids in variable regions are indicated according to the Kabat numbering. Amino acids in constant regions are indicated by the "EU numbering" or the "EU index" reported in the Kabat method (Sequences of Proteins of Immunological Interest, National Institute of Health, Bethesda, Md., 1987 and 1991) described above.

Measurement of Expression Level of GPC3

The present invention relates to a method for determining the efficacy of a GPC3-targeting therapeutic agent for a patient, the method comprising the step of measuring an expression level of GPC3 per tumor cell in a biological sample isolated from the patient.

Biological Sample

In the present invention, the "biological sample" refers to a sample of a tissue or a fluid isolated from a subject. In a non-limiting aspect, examples of such samples include plasma, serum, spinal fluid, lymph, external sections of skin, respiratory tract, intestinal tract, and genitourinary tract, tear, saliva, sputum, milk, whole blood or any blood fraction, blood derivatives, blood cells, tumor, nervous tissues, organs or any type of tissue, any sample obtained by lavage (e.g., samples derived from the bronchi), and samples of components constituting cell cultures in vitro.

The term "isolated" refers to "artificially" changed from a natural state, i.e., changed and/or extracted from the original environment of naturally occurring matter. The term "isolated" means that, for example, a cell, a polynucleotide, or a polypeptide present in an organism is in an unisolated state, whereas the same cell, polynucleotide, or polypeptide thereas is isolated when separated from a material present with the cell, the polynucleotide, or the polypeptide in a natural state. A polynucleotide or a polypeptide transferred into an organism by transformation, genetic manipulation, or any other recombination method is in an isolated state even when present in the organism (regardless of being alive or dead).

In the present invention, preferred examples of the biological sample used for detecting the expression level of GPC3 per tumor cell in tissues include test subject-derived preparations. The test subject-derived preparation is preferably a tissue obtained from the test subject, more preferably a liver cancer or hepatocellular carcinoma tissue of the test subject. The liver cancer or hepatocellular carcinoma tissue is preferably collected by use of biopsy, a method known in the art. The liver biopsy refers to a method of directly inserting a thin long needle into the liver from skin surface and collecting liver tissues. The needling site is typically the intercostal space of the right lower chest. Before the operation, the safety of the needling site is confirmed using an ultrasonic examination apparatus. Then, the needling site is disinfected. A region from the skin to the surface of the liver is subject to anesthesia. After small incision of the skin at the needling site, a puncture needle is inserted thereto.

For the microscopic observation of the tissue preparation by transmitted beams, the tissue preparation is sliced to a degree that allows beams of light for use in the microscope to sufficiently penetrate the tissue slice. At a stage prior to the slicing, the tissue preparation is fixed. Specifically, proteins in tissues or cells are coagulated by dehydration or denaturation to thereby rapidly kill the cells constituting the tissues so that the structures thereof are stabilized and insolubilized. First, the tissue preparation to be fixed is cut into a fragment with a size and a shape suitable for the preparation of paraffin-embedded sections by use of a knife such as a surgical knife. Subsequently, the fragment is dipped in a fixative, which is a reagent used for carrying out fixation. Formalin, more preferably neutral buffered formalin, is preferably used as the fixative. The concentration of the neutral buffered formalin is appropriately selected according to the characteristics or physical properties of the tissue preparation. The concentration used can be appropriately changed between 1 and 50%, preferably 5 and 25%, more preferably 10 and 15%. The fixative with the tissue preparation dipped therein is appropriately degassed using a vacuum pump. The fixation is carried out by leaving the tissue preparation for several hours in the fixative under conditions of ordinary pressure and room temperature. The time required for the fixation can be appropriately selected within the range of 1 hour to 7 days, preferably 2 hours to 3 days, more preferably 3 hours to 24 hours, further preferably 4 hours to 16 hours. The tissue preparation thus fixed is appropriately dipped in a phosphate buffer solution or the like for additional several hours (which can be appropriately selected within the range of 2 hours to 48 hours, preferably 3 hours to 24 hours, more preferably 4 hours to 16 hours).

Next, sections can be preferably prepared by freeze sectioning or paraffin sectioning from the tissue preparation thus fixed. Preferred examples of the freeze sectioning include a method which involves adding tissues into O.C.T. Compound (Miles Inc.), freezing the mixture, and slicing the frozen mixture using a cryostat (frozen section preparation apparatus). In the paraffin sectioning, the fixed tissue preparation is dipped in an embedding agent, which is then solidified to thereby impart thereto uniform and appropriate hardness. Paraffin can be preferably used as the embedding agent. The fixed tissue preparation is dehydrated using ethanol. Specifically, the tissue preparation is dipped in 70% ethanol, 80% ethanol, and 100% ethanol in this order and thereby dehydrated. The time required for the dipping and the number of runs can be appropriately selected within the ranges of 1 hour to several days and 1 to 3 times, respectively. The tissue preparation may be dipped therein at room temperature or 4° C. In the case of dipping at 4° C., a longer dipping time (e.g., overnight) is more preferred. After replacement of the liquid phase with xylene, the tissue preparation is embedded in paraffin. The time required for the replacement of the liquid phase with xylene can be appropriately selected within the range of 1 hour to several hours. This replacement may be performed at room temperature or may be performed at 4° C. In the case of replacement at 4° C., a longer replacement time (e.g., overnight) is more preferred. The time required for the embedding in paraffin and the number of runs can be appropriately selected within the ranges of 1 hour to several hours and 1 to 4 times, respectively. This embedding may be performed at room temperature or may be performed at 4° C. In the case of embedding at 4° C., a longer embedding time (e.g., overnight) is more preferred. Alternatively, the tissue preparation may be preferably embedded in paraffin by using a paraffin embedding apparatus (EG1160, Leica, etc.) which automatically performs paraffin embedding reaction.

The tissue preparation thus paraffin-embedded is bonded to a block base to prepare a "block". This block is sliced into the desired thickness selected from thicknesses of 1 to 20 μm by use of a microtome. The sliced tissue section is left standing on a glass slide as a permeable support and thereby fixed thereon. In this case, the glass slide coated with 0.01% poly-L-lysine (Sigma-Aldrich Co., LLC) and then dried can be preferably used in order to prevent the tissue section from coming off. The fixed tissue section is dried in air for an appropriate time selected from between several minutes and 1 hour.

Epitope Retrieval

In a preferred aspect, an epitope in an antigen whose reactivity with an antibody has been attenuated due to formalin fixation is retrieved. In the present invention, protease-induced epitope retrieval (PIER) may be applied to the retrieval, or heat-induced epitope retrieval (HIER) may be applied thereto. In a non-limiting aspect, PIER may be applied to one of "two identifiable tissue preparations" prepared as shown below, while HIER may be applied to the other preparation. A difference in the degree of staining between these preparations reacted with antibodies can be digitized.

In a non-limiting aspect, a set of two tissue preparations is prepared, which are prepared as shown in the paragraph "Biological sample" and attached onto permeable supports. The tissue preparations are desirably two histologically identifiable tissue preparations. The term "identifiable" means that two tissue preparations to be mutually compared are composed of substantially the same cells or tissues in test subject-derived preparations serving as origins of the tissue preparations. For example, two tissue preparations prepared as adjacent sections correspond to the two identifiable tissue preparations. In the present invention as well, the "two identifiable tissue preparations" refer to two tissue preparations prepared as adjacent sections, unless otherwise specified. In addition, two tissue preparations composed of cells or tissues structurally identifiable between the preparations correspond to the "two identifiable tissue preparations", even if the tissue preparations are not prepared as adjacent sections. Preferred examples of such two tissue preparations composed of cells or tissues structurally identifiable therebetween include (1) tissue sections containing cells derived from the same cells at the same positions on plane coordinates in the sections, and (2) tissue sections in which at least 50% or more, preferably 60% or more, more preferably 70% or more, further preferably 80% or more, still further preferably 90% or more, particularly preferably 95% or more of the cells are present at the same positions on the plane coordinates.

The heat-induced epitope retrieval appropriately employs, for example, a heating method using microwave, a heating method using an autoclave, or a heating method using boiling treatment. In the case of boiling treatment at an output of 780 W so as to keep a liquid temperature at approximately 98° C., the time required for the retrieval including the treatment is appropriately selected from between 5 minutes and 60 minutes and is, for example, 10 minutes. The epitope retrieval treatment can be performed in a 10 mM sodium citrate buffer solution as well as commercially available Target Retrieval Solution (DakoCytomation Inc.), for example. Target Retrieval Solution is used in Examples described below. Any buffer solution or aqueous solution is preferably used as long as a result of the retrieval treatment, an epitope in the antigen that is recognized by an anti-GPC3 antibody acquires binding activity against the antibody, which permits detection of an antigen-antibody complex mentioned later.

The protease for use in the protease-induced epitope retrieval is not particularly limited by its type or origin. Generally available protease can be appropriately selected for use. Preferred examples of the protease used include pepsin with 0.05% concentration in 0.01 N hydrochloric acid, trypsin with 0.1% concentration further containing $CaCl_2$ with 0.01% concentration in a Tris buffer solution (pH 7.6), and protease K with a concentration of 1 to 50 μg/ml in a 10 mM Tris-HCl buffer solution (pH 7.8) containing 10 mM EDTA and 0.5% SDS. In the case of using protease K, the pH of the reaction solution is appropriately selected from between 6.5 and 9.5, and an SH reagent, a trypsin inhibitor, or a chymotrypsin inhibitor can be appropriately used. Specific examples of such preferred protease also include protease attached to Histofine HER2 kit (MONO) (Nichirei Biosciences Inc.). The protease-induced epitope retrieval is usually performed at 37° C. The reaction temperature can be appropriately changed within the range of 25° C. to 50° C. The reaction time of the protease-induced epitope retrieval performed at 37° C. is appropriately selected from between, for example, 1 minute and 5 hours and is, for example, 15 minutes, 30 minutes, 45 minutes, 1 hour, 2 hours, 3 hours, or 4 hours. After the completion of the retrieval treatment, the tissue preparation thus treated is washed with a buffer solution for washing. PBS (phosphate buffered saline) is preferably used as the buffer solution for washing. Alternatively, a Tris-HCl buffer solution may be preferably used. The washing conditions adopted in this method usually involve three runs of washing at room temperature for 5 minutes. The washing time and temperature can be appropriately changed.

Reaction Between Tissue Preparation and Anti-GPC3 Antibody

The tissue preparation thus treated by the heat-induced epitope retrieval and/or the tissue preparation thus treated by the protease-induced epitope retrieval are reacted with an anti-GPC3 antibody mentioned later as a primary antibody. The reaction is carried out under conditions appropriate for the formation of an antigen-antibody complex through the recognition of an epitope in the antigen by the anti-GPC3 antibody. The reaction is usually carried out overnight at 4° C. or at 37° C. for 1 hour. The reaction conditions can be appropriately changed within a range appropriate for the formation of an antigen-antibody complex through the recognition of an epitope in the antigen by the antibody. For example, the reaction temperature can be changed within the range of 4° C. to 50° C., and the reaction time can be changed between 1 minute and 7 days. A longer reaction time is more preferred for the reaction carried out at a low temperature. After the completion of the primary antibody reaction, the tissue preparation is washed with a buffer solution for washing. PBS (phosphate buffered saline) is preferably used as the buffer solution for washing. Alternatively, a Tris-HCl buffer solution may be preferably used. The washing conditions adopted in this method usually involve three runs of washing at room temperature for 5 minutes. The washing time and temperature can be appropriately changed.

Subsequently, the tissue preparation thus reacted with the primary antibody is reacted with a secondary antibody that recognizes the primary antibody. A secondary antibody labeled in advance with a labeling material for visualizing the secondary antibody is usually used. Preferred examples of the labeling material include: fluorescent dyes such as FITC (fluorescein isothiocyanate), Cy2 (GE Healthcare Japan Corp.), Alexa 488 (Life Technologies Corp.), and Qdot 655 (Life Technologies Corp.); enzymes such as peroxidase and alkaline phosphatase; and gold colloid.

The reaction with the secondary antibody is carried out under conditions appropriate for the formation of an antigen-antibody complex between the anti-GPC3 antibody and the secondary antibody that recognizes the anti-GPC3 antibody. The reaction is usually carried out at room temperature or 37° C. for 30 minutes to 1 hour. The reaction conditions can be appropriately changed within a range appropriate for the formation of an antigen-antibody complex between the anti-GPC3 antibody and the secondary antibody. For example, the reaction temperature can be changed within the range of 4° C. to 50° C., and the reaction time can be changed between 1 minute and 7 days. A longer reaction time is more preferred for the reaction carried out at a low temperature. After the completion of the secondary antibody reaction, the tissue preparation is washed with a buffer solution for washing. PBS (phosphate buffered saline) is preferably used as the buffer solution for washing. Alternatively, a Tris-HCl buffer solution may be preferably used. The washing conditions adopted in this method usually involve three runs of washing at room temperature for 5 minutes. The washing time and temperature can be appropriately changed.

Next, the tissue preparation thus reacted with the secondary antibody is reacted with a substance that visualizes the labeling material. In the case of using peroxidase as the labeling material in the secondary antibody, a 0.02% aqueous hydrogen peroxide solution and a DAB (diaminobenzidine) solution concentration-adjusted to 0.1% with a 0.1 M Tris-HCl buffer solution (pH 7.2) are mixed in equal amounts immediately before incubation and the tissue preparation is incubated in the resulting reaction solution. A chromogenic substrate such as DAB-Ni or AEC+ (both from Dako Japan Inc.) can be appropriately selected instead of DAB. During the course of incubation, the visualization reaction can be stopped by the dipping of the tissue preparation in PBS at the stage where appropriate color development is confirmed by the occasional microscopic observation of the degree of color development.

In the case of using alkaline phosphatase as the labeling material in the secondary antibody, the tissue preparation is incubated in a BCIP (5-bromo-4-chloro-3-indolyl phosphoric acid)/NBT (nitro blue tetrazolium) (Zymed Laboratories, Inc.) substrate solution (solution of NBT and BCIP dissolved at concentrations of 0.4 mM and 0.38 mM, respectively, in a 50 mM sodium carbonate buffer solution (pH 9.8) containing $MgCl_2$ with a concentration of 10 mM and NaCl with a concentration of 28 mM). Alternatively, for example, Permanent Red, Fast Red, or Fuchsin+ (all from Dako Japan Inc.) may be appropriately used instead of BCIP and NBT. Prior to the incubation, the tissue preparation may be pre-incubated at room temperature for 1 minute to several hours with a 0.1 M Tris-HCl buffer solution (pH 9.5) containing levamisole chloride (Nacalai Tesque, Inc.), an inhibitor of endogenous alkaline phosphatase, with a concentration of 1 mM, 0.1 M sodium chloride, and 50 mM magnesium chloride. During the course of incubation, the tissue preparation is washed with water, or washed with TBST (TBS containing 0.1% TWEEN® 20) after stop of the reaction by the addition of TBS containing 2% polyvinyl alcohol, at the stage where the deposition of a final reaction product purple formazan is confirmed by occasional microscopic observation. In the case of using gold colloid as the label in the secondary antibody, metallic silver is attached to gold particles by silver intensification to thereby visualize the gold colloid. The silver intensification method is known to those skilled in the art.

In the case of using a fluorescent dye such as FITC (fluorescein isothiocyanate), Cy2 (GE Healthcare Japan Corp.), Alexa 488 (Life Technologies Corp.), or Qdot 655 (Life Technologies Corp.) as the labeling material in the secondary antibody, the reaction step of the visualizing substance is unnecessary. The tissue preparation is irradiated with light at an excitation wavelength for the fluorescent material. Emitted light can be appropriately detected using a fluorescence microscope. Also, the light emitted by irradiation with light at an excitation wavelength for the fluorescent material can be appropriately detected using a virtual slide scanner or the like. Preferred examples of the virtual slide scanner for use in the detection of the fluorescent material include Nano Zoomer (Hamamatsu Photonics K.K.).

Digitization of GPC3 Expression Level

The present invention provides a method for digitizing a GPC3 expression level by calculating the GPC3 expression level per unit area or the GPC3 expression level per tumor cell in tumor tissues in a tissue preparation from GPC3 detected in the tissue preparation by the method described above. The tumor tissues in the tissue preparation can be appropriately identified by a method known to those skilled in the art. The GPC3 expression level per unit area in the tumor tissues in the tissue preparation can be calculated by dividing, for example, total staining intensity or fluorescence intensity detected from the tumor tissues in the tissue preparation by the area of the tumor tissues in a region used in this detection. The GPC3 expression level per tumor cell in the tissue preparation can be calculated by dividing, for example, total staining intensity or fluorescence intensity detected from the tumor tissues in the tissue preparation by the number of cells present in the tumor tissues (i.e., the number of tumor cells) used in this detection. The number of cells in the tumor tissues used in the detection can be calculated from the number of cell nuclei present in the tumor tissues. In short, the GPC3 expression level per tumor cell in the tissue preparation is a numerical value determined by dividing the abundance of GPC3 in tumor cells and on tumor cell membranes by the number of tumor cells (or the number of tumor cell nuclei).

Immunohistochemical Staining Score

As for the GPC3 expression level in cytoplasms or cell membranes, the respective scores of positive cell rate (PR), detected staining intensity of cytoplasm (SI-cp) or staining intensity of cell membrane (SI-cm), and staining pattern of cell membrane (Sp-cm) are calculated according to the criteria shown in Table 1 by a method described in WO2009116659 and added on the basis of calculation expressions 1 and 2. The resulting score is exemplified as a non-limiting immunohistochemical staining score of GPC3 (referred to as "composite score 1" for the sake of convenience) of the present invention.

IHC total=PR+SI-Cp+SI-Cm+Sp-Cm          Expression 1

IHC cm=PR+SI-Cm+Sp-Cm          Expression 2

TABLE 1-2

| Composite score 1 | IHC total score |
|---|---|
| High expression | 7 or higher |
| Low or moderate expression | Lower than 7 |

In addition, the GPC3 expression can be calculated by division by the area of a region in cell membranes or cytoplasms. The GPC3 expression level per tumor cell in the tissue preparation can be calculated by classifying detected staining intensity into 0 to 3, calculating, for example, H scores (literature: K S. McCarty Jr. et al., Use of a monoclonal anti-Estrogen receptor antibody in the immunohistochemical evaluation of human tumors. Cancer Res. (1986) 46, 4244s-4248s) on the basis of the proportion of cells that exhibit each staining or fluorescence intensity, and dividing the total H score by the number of cells present in the region used in this detection. The number of cells in the region used in the detection can be calculated from the number of cell nuclei present in this region.

Another example of the immunohistochemical staining score includes the following scoring algorithm for classification of 0 to 3+ on the basis of the staining intensity of membrane, the staining intensity of cytoplasm, and the degree of staining, and an evaluation score based on the algorithm (composite score 2).

TABLE 1-1

| Criterion | Evaluation | Score |
|---|---|---|
| Positive cell rate (PR) | 0 | 0 |
| | 1% or more and less than 20% | 1 |
| | 20% or more and less than 50% | 2 |
| | 50% or more | 3 |
| Staining intensity (SI) | Slightly positive | 0 |
| Cytoplasm (SI-cp) | Weakly positive | 1 |
| Cell membrane (SI-cm) | Moderately positive and/or weakly positive with strong positivity | 2 |
| | Moderately positive | 3 |
| | Strongly positive | 4 |
| Staining pattern of cell membrane (SP-cm) | Negative | 0 |
| | When only a portion of the cell membranes of cells was stained | 1 |
| | When a portion of the cell membranes of most of these cells was stained and the cell membranes of some of the cells were circumferentially stained | 2 |
| | When the cell membranes of most of these cells were circumferentially stained | 3 |

(In the evaluation of Sp-cm, cell staining in the visual field was evaluated by microscopy using an objective lens with a magnification of 4 or 10 or using total fluorescence intensity or the like in the detection.)

TABLE 2

| Composite score 2 | Evaluation |
|---|---|
| 0 | When cell membranes were not stained |
|  | When less than 10% of tumor cells exhibited intracytoplasmic staining |
| 1+ | When less than 10% of tumor cells exhibited cell membrane staining and/or |
|  | When 10% or more of tumor cells exhibited intracytoplasmic staining (note that strong intracytoplasmic staining, if any, remains at less than 50% of the tumor cells) |
| 2+ | When 10% or more of tumor cells exhibited weak or moderate cell membrane staining (note that strong cell membrane staining, if any, remains at less than 10% of the tumor cells) regardless of the presence or absence of intracytoplasmic staining in 10% or more of the tumor cells (note that intracytoplasmic staining, if any, remains at less than 50% of the tumor cells) |
| 3+ | When 10% or more of tumor cells exhibited strong cell membrane staining regardless of the presence or absence of intracytoplasmic staining or |
|  | When 50% or more of tumor cells exhibited strong intracytoplasmic staining |

In the present invention, for example, the composite score 1, the H score, and the composite score 2 may be used alone or in combination as the "immunohistochemical staining score of GPC3". In a non-limiting aspect, the composite score 1 can be used as the "immunohistochemical staining score of GPC3". In another non-limiting aspect, the composite score 2 can be used as the "immunohistochemical staining score of GPC3". In a non-limiting aspect, the "immunohistochemical staining score of GPC3" is a cell membrane H score or a cytoplasm H score in the immunohistochemical staining of GPC3.

Tumor Cell Density and Tumor Cell Size in Tissue Preparation

The density of tumor cells can be determined by counting the number of cells per unit area in tumor tissues (i.e., the number of tumor cells) in the tissue preparation. The size of each tumor cell can be determined by dividing the area of the tumor tissues in the tissue preparation by the number of cells present in the tumor tissues (i.e., the number of tumor cells). The density of tumor cells expressing GPC3 can be determined by counting the number of GPC3-expressing cells per unit area in tumor tissues (i.e., the number of tumor cells expressing GPC3) in the tissue preparation. The size of each tumor cell expressing GPC3 can be determined by dividing the total area of tumor cells in the tissue preparation by the number of GPC3-expressing cells (i.e., the number of tumor cells expressing GPC3). In this aspect, the subject can be a patient untreated with the GPC3-targeting therapeutic agent.

Immunofluorescent Quantification Digital Slide (IQD)

In the present specification, the "immunofluorescent quantification digital slide" means a computer-captured immunohistochemical image derived from reaction with a fluorescently labeled secondary antibody. It is known that digitization and storage in computers allow fluorescent images to be stored as slides (digital slides) immune to breakage, color degradation, or the like. The digital slides can store non-fluorescent stained tissue images because of the high storage stability of staining images and the high quantitative performance of the degree of staining. In the present specification, the digital slide is also referred to as a "virtual slide". In a preferred aspect of the present invention, the tissue preparation reacted with a secondary antibody is evaluated by immunofluorescent quantification digital slide (IQD) to calculate a GPC3 expression level per unit area or a GPC3 expression level per tumor cell in tumor tissues in the tissue preparation. In the evaluation by the immunofluorescent quantification digital slide, the tissue preparation reacted with a secondary antibody is scanned in the virtual slide scanner described above to prepare a virtual slide from the tissue preparation. A region suitable for the measurement of the expression level of GPC3 is selected from the prepared virtual slide (IQD image), and the fluorescence intensity of tumor tissues in the region is measured. For example, ViwePlus software (Hamamatsu Photonics K.K.) is preferably used as software in the measurement of fluorescence intensity.

In a non-limiting aspect of the present invention, the expression level of GPC3 measured using IQD can be indicated by, for example, IQD intensity score or IQD cell score. The IQD intensity score is a score that represents a GPC3 expression level per unit area in tumor tissues in the tissue preparation, and is calculated by dividing the total fluorescence intensity of tumor tissues in the selected region by the area of the tumor tissues. The IQD cell score is a score that represents a GPC3 expression level per tumor cell in the tissue preparation, and is calculated by dividing the total fluorescence intensity of tumor tissues in the selected region by the number of cells in the tumor tissues (i.e., the number of tumor cells). The number of cells in the tumor tissues can be calculated from the number of cell nuclei present in the tumor tissues. A numerical value corrected with the fluorescence intensity of a non-cancer portion may be used as the IQD intensity score or the IQD cell score, or an uncorrected numerical value may be used thereas.

In the calculation of the IQD cell score, the number of cell nuclei present in the tumor tissues in the selected region in the tissue preparation is calculated by measuring the number of cell nuclei visualized in advance by staining. Examples of the method for staining the cell nuclei can include, but are not particularly limited to, hematoxylin staining. The tissue preparation to be subjected to evaluation based on the IQD cell score may be reacted with an anti-GPC3 antibody, for example, after staining of cell nuclei, and the number of cell nuclei and the expression level of GPC3 can be measured at the same time using the virtual slide scanner described above. Alternatively, the tissue preparation may first be reacted with an anti-GPC3 antibody, for example, and the expression level of GPC3 can be measured using the virtual slide scanner, followed by the staining of cell nuclei and the measurement of the number of cell nuclei using the virtual slide scanner again. Thus, the immunofluorescent quantification digital slide permits long-term storage of data and also achieves more convenient and highly quantitative measurement of the expression level of GPC3 and the expression level of GPC3 per unit area and the expression level of GPC3 per tumor cell in tumor tissues.

Confirmation of Fcγ Receptor Gene Polymorphism

In a non-limiting aspect, the present invention also provides a method comprising the step of confirming whether the applicable patient has an Fcγ receptor gene polymorphism, in addition to the measurement of the expression level per tumor cell of GPC3 detected in the biological sample by the method described above. In the present invention, the method for confirming whether the applicable patient has an Fcγ receptor gene polymorphism is not particularly limited. For example, a biological sample is collected from the applicable patient, and the genomic gene is isolated from the collected sample. The nucleotide sequence of a gene corresponding to the Fcγ receptor can be determined to confirm the presence or absence of the polymorphism. Specifically, this assay can be conducted according to a method described in, for example, Journal of Clinical Oncology, vol. 21, No. 21 (2003) pp. 3940-3947. In this context, the biological sample to be collected is not particularly limited as long as the sample permits obtainment of the patient-derived genomic gene. Examples thereof include peripheral blood and skin sections.

Measurement of Free GPC3 Concentration

In a non-limiting aspect, the present invention also provides a method comprising the step of measuring a free GPC3 concentration in a biological sample isolated from a patient before the start of administration of a GPC3-targeting therapeutic agent and/or a patient treated with the GPC3-targeting therapeutic agent, in addition to the measurement of the expression level per tumor cell of GPC3 detected in the biological sample by the method described above. The "patient before the start of administration of a GPC3-targeting therapeutic agent" refers to a patient diagnosed with cancer, having no history of administration of the GPC3-targeting therapeutic agent. For this patient, it may be determined that the GPC3-targeting therapeutic agent is effective from the expression level of GPC3 per tumor cell in tissues as mentioned above. The "patient treated with the GPC3-targeting therapeutic agent" refers to a patient having a history of administration of the GPC3-targeting therapeutic agent.

The "free GPC3" refers to GPC3 unanchored to GPC3-expressing cells and includes fragments of secretory GPC3 that can be easily dissociated from GPC3 anchored to GPC3-expressing cells under particular conditions in vivo or in vitro. In a non-limiting aspect, examples of the "free GPC3" can include a polypeptide from the amino terminus to position 358 in GPC3 consisting of the polypeptide defined by SEQ ID NO: 1, a polypeptide from the amino terminus to position 374 in GPC3 consisting of the polypeptide defined by SEQ ID NO: 1, a GPC3 polypeptide liberated by the degradation of a GPI anchor present at the carboxy terminus, and their fragments (WO2004/038420). Those skilled in the art can appropriately select an approach known in the art for determining the structure of free GPC3. In a non-limiting aspect, for example, a method can be appropriately used, which involves directly detecting free GPC3 present in the plasma of a patient or an animal model by the method described in Patent Literature 7 or the like and analyzing its structure, or involves, for example, allowing an enzyme dissociating free GPC3, such as convertase, phospholipase D, or Notum, to act on GPC3 expressed in cells cultured in vitro, detecting the resulting free GPC3, and analyzing its structure (e.g., J. Cell. Biol. (2003) 163 (3), 625-635).

In a non-limiting aspect, the free GPC3 concentration in the biological sample isolated from a patient before the start of administration of a GPC3-targeting therapeutic agent and/or a patient treated with the GPC3-targeting therapeutic agent can be measured according to a method described in WO2014/097648.

GPC3-Targeting Therapeutic Agent

In the present invention, the term "GPC3-targeting therapeutic drug" refers to every molecule that blocks, suppresses, inhibits, or reduces the biological activity of GPC3 including a signal pathway mediated by GPC3 or is cytotoxic to cells expressing GPC3. The term "targeting treatment or "targeting therapy" does not suggest any particular mechanism having biological effects and conceptually includes every possible effect of the pharmacological, physiological, and biochemical interactions of GPC3. Examples of the GPC3-targeting therapeutic drug include: (1) antagonistic or non-antagonistic inhibitors of the binding of GPC3 to a GPC3-binding ligand, i.e., active substances that interfere with the binding of GPC3 to its ligand; (2) active substances that do not interfere with the binding of GPC3 to its ligand but instead inhibit or decrease activity brought about by the binding of GPC3 to its ligand; (3) active substances that decrease GPC3 expression; and (4) active substances capable of eliciting cytotoxic activity against cells expressing GPC3. In a non-limiting aspect, examples of the ligand can include wnt (Cancer Res. (2005) 65, 6245-6254), IGF-II (Carcinogenesis (2008) 29 (7), 1319-1326), and fibroblast growth factor 2 (Int. J. Cancer (2003) 103 (4), 455-465). In a non-limiting aspect, such active substances can include, for example, antibodies (including their antigen-binding domains or fragments), nucleic acid molecules (antisense or RNAi molecules, etc.), peptides, non-peptidic low-molecular-weight organic materials, and immunocytes.

In a non-limiting aspect, examples of the non-peptidic low-molecular-weight organic material that may be used as the GPC3-targeting therapeutic agent of the present invention include non-peptidic low-molecular-weight quinoline derivatives (WO2008/046085) which act on methylation suppressor genes. Further examples thereof can include HLA-A2-restricted GPC3 peptide 144-152 (SEQ ID NO: 2) and HLA-A24-restricted GPC3 peptide 298-306 (SEQ ID NO: 3) (Clin. Cancer Res. (2006) 12 (9), 2689-2697) which elicit the cytotoxic activity of cytotoxic T cells.

In a non-limiting aspect, examples of the immunocytes that may be used as the GPC3-targeting therapeutic agent of the present invention can also include GPC3 chimeric antigen receptor (CAR) gene-transfected T cells (WO2014/180306). Combined use of GPC3-targeting therapeutic agent with additional anticancer agent The GPC3-targeting therapeutic agent of the present invention may be used in combination with one or two or more anticancer agent(s) in the same preparation or separate preparations and administered concurrently with or separately from the anticancer agent(s). The anticancer agent appropriate for the combined use with the GPC3-targeting therapeutic agent of the present invention is a chemotherapeutic agent and is preferably a multikinase inhibitor, more preferably sorafenib or sunitinib. The anticancer agent for the combined use with the GPC3-targeting therapeutic agent is not conjugated with the GPC3-targeting therapeutic agent. The GPC3-targeting therapeutic agent and the anticancer agent may be provided in the form of a combination drug containing both of these agents, or may be separately provided and used concurrently, separately, or sequentially. Alternatively, the GPC3-targeting therapeutic agent and the anticancer agent may be provided as a kit constituted by these agents.

Anti-GPC3 Antibody

In a non-limiting aspect, examples of the anti-GPC3 antibody for use as the GPC3-targeting therapeutic agent of the present invention can include an antibody drug conjugate (ADC) (WO2007/137170) comprising a 1G12 antibody (WO2003/100429) (sold under catalog No. B0134R by BioMosaics Inc.) conjugated with a cytotoxic substance, and anti-GPC3 single chain variable fragment (scFv) (CN103833852).

In an alternative non-limiting aspect, examples of the anti-GPC3 antibody include a humanized anti-GPC3 antibody described in WO2006/006693 or WO2009/041062. Specifically, a humanized anti-GPC3 antibody comprising heavy chain CDR1, heavy chain CDR2, and heavy chain CDR3 represented by SEQ ID NO: 4, SEQ ID NO: 5, and SEQ ID NO: 6, respectively, and light chain CDR1, light chain CDR2, and light chain CDR3 represented by SEQ ID NO: 7, SEQ ID NO: 8, and SEQ ID NO: 9, respectively, can be used as the GPC3-targeting therapeutic agent of the present invention. For the preparation of the humanized anti-GPC3 antibody, human framework sequences having high sequence identity to a heavy chain framework sequence represented by SEQ ID NO: 10 or a light chain framework sequence represented by SEQ ID NO: 11 are appropriately selected and then used as templates for humanization.

In a further alternative non-limiting aspect, an anti-GPC3 chimeric antibody or a humanized anti-GPC3 antibody comprising heavy chain CDR1, heavy chain CDR2, and heavy chain CDR3 represented by SEQ ID NO: 12, SEQ ID NO: 13, and SEQ ID NO: 14, respectively, and light chain CDR1, light chain CDR2, and light chain CDR3 represented by SEQ ID NO: 15, SEQ ID NO: 16, and SEQ ID NO: 17, respectively, can be used as the GPC3-targeting therapeutic agent of the present invention. For the preparation of the humanized anti-GPC3 antibody, human framework sequences having high sequence identity to a heavy chain framework sequence represented by SEQ ID NO: 18 or a light chain framework sequence represented by SEQ ID NO: 19 are appropriately selected and then used as templates for humanization.

In an alternative non-limiting aspect, an anti-GPC3 chimeric antibody or a humanized anti-GPC3 antibody comprising heavy chain CDR1, heavy chain CDR2, and heavy chain CDR3 represented by SEQ ID NO: 20, SEQ ID NO: 21, and SEQ ID NO: 22, respectively, and light chain CDR1, light chain CDR2, and light chain CDR3 represented by SEQ ID NO: 23, SEQ ID NO: 24, and SEQ ID NO: 25, respectively, can be used as the GPC3-targeting therapeutic agent of the present invention. For the preparation of the humanized anti-GPC3 antibody, human framework sequences having high sequence identity to a heavy chain framework sequence represented by SEQ ID NO: 26 or a light chain framework sequence represented by SEQ ID NO: 27 are appropriately selected and then used as templates for humanization.

In a further alternative non-limiting aspect, an anti-GPC3 chimeric antibody or a humanized anti-GPC3 antibody comprising heavy chain CDR1, heavy chain CDR2, and heavy chain CDR3 represented by SEQ ID NO: 28, SEQ ID NO: 29, and SEQ ID NO: 30, respectively, and light chain CDR1, light chain CDR2, and light chain CDR3 represented by SEQ ID NO: 31, SEQ ID NO: 32, and SEQ ID NO: 33, respectively, can be used as the GPC3-targeting therapeutic agent of the present invention. For the preparation of the humanized anti-GPC3 antibody, human framework sequences having high sequence identity to a heavy chain framework sequence represented by SEQ ID NO: 34 or a light chain framework sequence represented by SEQ ID NO: 35 are appropriately selected and then used as templates for humanization.

In an alternative non-limiting aspect, an anti-GPC3 chimeric antibody or a humanized anti-GPC3 antibody comprising heavy chain CDR1, heavy chain CDR2, and heavy chain CDR3 represented by SEQ ID NO: 36, SEQ ID NO: 37, and SEQ ID NO: 38, respectively, and light chain CDR1, light chain CDR2, and light chain CDR3 represented by SEQ ID NO: 39, SEQ ID NO: 40, and SEQ ID NO: 41, respectively, can be used as the GPC3-targeting therapeutic agent of the present invention. For the preparation of the humanized anti-GPC3 antibody, human framework sequences having high sequence identity to a heavy chain framework sequence represented by SEQ ID NO: 42 or a light chain framework sequence represented by SEQ ID NO: 43 are appropriately selected and then used as templates for humanization.

In a further alternative non-limiting aspect, a humanized anti-GPC3 antibody comprising a heavy chain variable region selected from the group of heavy chain variable regions represented by SEQ ID NO: 44, SEQ ID NO: 45, SEQ ID NO: 46, SEQ ID NO: 47, SEQ ID NO: 48, SEQ ID NO: 49, and SEQ ID NO: 50 and a light chain variable region represented by SEQ ID NO: 51 can be used as the GPC3-targeting therapeutic agent of the present invention. In a further alternative non-limiting aspect, a humanized anti-GPC3 antibody comprising a heavy chain variable region selected from the group of heavy chain variable regions represented by SEQ ID NO: 44, SEQ ID NO: 45, SEQ ID NO: 46, SEQ ID NO: 47, SEQ ID NO: 48, SEQ ID NO: 49, and SEQ ID NO: 50 and a light chain variable region selected from the group of light chain variable regions represented by SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, and SEQ ID NO: 66 can be used as the GPC3-targeting therapeutic agent of the present invention.

In a further alternative non-limiting aspect, a humanized anti-GPC3 antibody comprising a heavy chain variable region represented by SEQ ID NO: 67 and a light chain variable region represented by SEQ ID NO: 68, a humanized anti-GPC3 antibody comprising a heavy chain variable region represented by SEQ ID NO: 69 and a light chain variable region represented by SEQ ID NO: 70, a humanized anti-GPC3 antibody comprising a heavy chain variable region represented by SEQ ID NO: 71 and a light chain variable region represented by SEQ ID NO: 72, or a humanized anti-GPC3 antibody comprising a heavy chain variable region represented by SEQ ID NO: 71 and a light chain variable region represented by SEQ ID NO: 73 can also be used as the GPC3-targeting therapeutic agent of the present invention.

Cytotoxic Activity

Examples of the anti-GPC3 antibody of the present invention include an anti-GPC3 antibody having cytotoxic activity. In the present invention, non-limiting examples of the cytotoxic activity include antibody-dependent cell-mediated cytotoxicity or antibody-dependent cellular cytotoxicity (ADCC) activity, complement-dependent cytotoxicity (CDC) activity, and cytotoxic activity based on T cells. In the present invention, the CDC activity means cytotoxic activity brought about by the complement system. On the other hand, the ADCC activity means the activity of damaging target cells by, for example, immunocytes, through the binding of the immunocytes via Fcγ receptors expressed on the immunocytes to the Fc regions of antigen-binding molecules comprising antigen-binding domains binding to membrane molecules expressed on the cell membranes of the target cells. Whether or not the antigen-binding molecule of interest has ADCC activity or has CDC activity can be determined by a method known in the art (e.g., Current protocols in Immunology, Chapter 7. Immunologic studies in humans, Coligan et al., ed. (1993)).

Specifically, effector cells, a complement solution, and target cells are first prepared.

(1) Preparation of Effector Cells

Spleen cells are separated in an RPMI1640 medium (Invitrogen Corp.) from the spleens harvested from CBA/N mice or the like. The spleen cells can be washed with the same medium as above containing 10% fetal bovine serum (FBS, HyClone Laboratories, Inc.) and then concentration-adjusted to $5 \times 10^6$ cells/mL to prepare the effector cells.

(2) Preparation of Complement Solution

Baby Rabbit Complement (CEDARLANE Laboratories Ltd.) can be diluted 10-fold with a medium (Invitrogen Corp.) containing 10% FBS to prepare the complement solution.

(3) Preparation of Target Cells

Antigen-expressing cells can be cultured at 37° C. for 1 hour, together with 0.2 mCi $^{51}$Cr-sodium chromate (GE Healthcare Bio-Sciences Corp.), in a DMEM medium containing 10% FBS to thereby radiolabel the target cells. The cells thus radiolabeled can be washed three times with an RPMI1640 medium containing 10% FBS and then concentration-adjusted to $2 \times 10^5$ cells/mL to prepare the target cells.

The ADCC activity or the CDC activity can be measured by a method described below. For the ADCC activity measurement, the target cells and the antigen-binding molecule (each 50 μl/well) are added to a U-bottom 96-well plate (Becton, Dickinson and Company) and reacted for 15 minutes on ice. Then, 100 μl of the effector cells is added to each well, and the plate is left standing for 4 hours in a $CO_2$ incubator. The final concentration of the antibody (antigen-binding molecule) can be set to, for example, 0 or 10 μg/ml. The radioactivity of 100 μl of the supernatant recovered from each well of the plate thus left standing is measured using a gamma counter (COBRA II AUTO-GAMMA, MODEL D5005, Packard Instrument Company). The cytotoxic activity (%) can be calculated on the basis of the calculation expression (A–C)/(B–C)×100 using the measurement value. In the expression, A represents radioactivity (cpm) from each sample; B represents radioactivity (cpm) from a sample supplemented with 1% NP-40 (Nacalai Tesque, Inc.); and C represents radioactivity (cpm) from a sample containing only the target cells.

For the CDC activity measurement, the target cells and the antigen-binding molecule (each 50 μl/well) are added to a flat-bottomed 96-well plate (Becton, Dickinson and Company) and reacted for 15 minutes on ice. Then, 100 μl of the complement solution is added to each well, and the plate is left standing for 4 hours in a $CO_2$ incubator. The final concentration of the antibody (antigen-binding molecule) can be set to, for example, 0 or 3 μg/ml. The radioactivity of 100 μl of the supernatant recovered from each well of the plate thus left standing is measured using a gamma counter. The cytotoxic activity can be calculated in the same way as in the ADCC activity measurement.

Cytotoxic Substance

In a non-limiting aspect, examples of the anti-GPC3 antibody of the present invention also include an anti-GPC3 antibody conjugated with a cytotoxic substance. Such an anti-GPC3 antibody drug conjugate (ADC) is specifically disclosed in, for example, WO2007/137170, though the conjugate of the present invention is not limited to those described therein. Specifically, the cytotoxic substance may be any of chemotherapeutic agents listed below or may be a compound disclosed in Alley et al. (Curr. Opin. Chem. Biol. (2010) 14, 529-537) or WO2009/140242. Antigen-binding molecules are conjugated with these compounds via appropriate linkers or the like.

Examples of the chemotherapeutic agents that may be conjugated to the anti-GPC3 antibody of the present invention can include the following: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, vincristine.

In the present invention, a preferred chemotherapeutic agent is a low-molecular-weight chemotherapeutic agent. The low-molecular-weight chemotherapeutic agent is unlikely to interfere with the functions of the anti-GPC3 antibody even after forming the anti-GPC3 antibody drug conjugate of the present invention. In the present invention, the low-molecular-weight chemotherapeutic agent has a molecular weight of usually 100 to 2000, preferably 200 to 1000. All of the chemotherapeutic agents listed herein are low-molecular-weight chemotherapeutic agents. These chemotherapeutic agents according to the present invention include prodrugs that are converted to active chemotherapeutic agents in vivo. The activation of the prodrugs may be enzymatic conversion or may be non-enzymatic conversion.

Examples of the cytotoxic substance to be conjugated in the anti-GPC3 antibody drug conjugate of the present invention can also include toxic peptides (toxins) such as *Pseudomonas* exotoxin A, saporin-s6, diphtheria toxin, and cnidarian toxin, radioiodine, and photosensitizers. Examples of the toxic peptides preferably include the following: Diphtheria toxin A Chain (Langone et al. (Methods in Enzymology (1983) 93, 307-308)); *Pseudomonas* Exotoxin (Nature Medicine (1996) 2, 350-353); Ricin A Chain (Fulton et al. (J. Biol. Chem. (1986) 261, 5314-5319), Sivam et al. (Cancer Res. (1987) 47, 3169-3173), Cumber et al., (J. Immunol. Methods (1990) 135, 15-24, Wawrzynczak et al. (Cancer Res. (1990) 50, 7519-7562), and Gheeite et al. (J. Immunol. Methods (1991) 142, 223-230)); Deglycosylated Ricin A Chain (Thorpe et al. (Cancer Res. (1987) 47, 5924-5931)); Abrin A Chain (Wawrzynczak et al. (Br. J. Cancer (1992) 66, 361-366), Wawrzynczak et al. (Cancer Res. (1990) 50, 7519-7562), Sivam et al. (Cancer Res. (1987) 47, 3169-3173), and Thorpe et al. (Cancer Res. (1987) 47, 5924-5931)); Gelonin (Sivam et al. (Cancer Res. (1987) 47, 3169-3173), Cumber et al. (J. Immunol. Methods (1990) 135, 15-24), Wawrzynczak et al. (Cancer Res. (1990) 50, 7519-7562), and Bolognesi et al. (Clin. exp. Immunol.

(1992) 89, 341-346)); PAP-s; Pokeweed anti-viral protein fromseeds (Bolognesi et al. (Clin. exp. Immunol. (1992) 89, 341-346)); Bryodin (Bolognesi et al. (Clin. exp. Immunol. (1992) 89, 341-346)); Saporin (Bolognesi et al. (Clin. exp. Immunol. (1992) 89, 341-346)); Momordin (Cumber et al. (J. Immunol. Methods (1990) 135, 15-24); Wawrzynczak et al. (Cancer Res. (1990) 50, 7519-7562), and Bolognesi et al. (Clin. exp. Immunol. (1992) 89, 341-346)); Momorcochin (Bolognesi et al. (Clin. exp. Immunol. (1992) 89, 341-346)); Dianthin 32 (Bolognesi et al. (Clin. exp. Immunol. (1992) 89, 341-346)); Dianthin 30 (Stirpe F., Barbieri L. (FEBS letter (1986) 195, 1-8)); Modeccin (Stirpe F., Barbieri L. (FEBS letter (1986) 195, 1-8)); Viscumin (Stirpe F., Barbieri L. (FEBS letter (1986) 195, 1-8)); Volkensin (Stirpe F., Barbieri L. (FEBS letter (1986) 195, 1-8)); Dodecandrin (Stirpe F., Barbieri L. (FEBS letter (1986) 195, 1-8)); Tritin (Stirpe F., Barbieri L. (FEBS letter (1986) 195, 1-8)); Luffin (Stirpe F., Barbieri L. (FEBS letter (1986) 195, 1-8)); and Trichokirin (Casellas et al. (Eur. J. Biochem. (1988) 176, 581-588), and Bolognesi et al. (Clin. exp. Immunol. (1992) 89, 341-346)).

In the case of measuring the cytotoxic activity of the anti-GPC3 antibody drug conjugate of the present invention, the target cells and the anti-GPC3 antibody drug conjugate (each 50 µl/well) are added to a flat-bottomed 96-well plate (Becton, Dickinson and Company) and reacted for 15 minutes on ice. The plate is incubated for 1 to 4 hours in a $CO_2$ incubator. The anti-GPC3 antibody drug conjugate can be appropriately used at a final concentration ranging from 0 to 3 µg/ml. After the culture, 100 µl of the supernatant is recovered from each well, and the radioactivity of the supernatant is measured using a gamma counter. The cytotoxic activity can be calculated in the same way as in the ADCC activity measurement.

Fc Region

An Fc region contained in a constant region contained in the anti-GPC3 antibody of the present invention can be obtained from human IgG, though the Fc region is not limited by a particular subclass of IgG. The Fc region refers to an antibody heavy chain constant region comprising a hinge region and CH2 and CH3 domains from the hinge region N terminus serving as a papain cleavage site, which is an amino acid at or around position 216 based on the EU numbering. Preferred examples of the Fc region include Fc regions having binding activity against Fcγ receptors as mentioned later. In a non-limiting aspect, examples of such Fc regions include Fc regions contained in constant regions represented by SEQ ID NO: 74 for human IgG1, SEQ ID NO: 75 for IgG2, SEQ ID NO: 76 for IgG3, and SEQ ID NO: 77 for IgG4.

Fcγ Receptor (FcγR)

The Fcγ receptor (also referred to as FcγR) refers to a receptor capable of binding to the Fc region of an IgG1, IgG2, IgG3, or IgG4 monoclonal antibody and substantially means even any member of a protein family encoded by Fcγ receptor genes. In humans, this family includes, but is not limited to: FcγRI (CD64) including isoforms FcγRIa, FcγRIb, and FcγRIc; FcγRII (CD32) including isoforms FcγRIIa (including allotypes H131 and R131; i.e., FcγRIIa (H) and FcγRIIa (R)), FcγRIIb (including FcγRIIb-1 and FcγRIIb-2), and FcγRIIc; FcγRIII (CD16) including isoforms FcγRIIIa (including allotypes V158 and F158; i.e., FcγRIIIa (V) and FcγRIIIa (F)) and FcγRIIIb (including allotypes FcγRIIIb-NA1 and FcγRIIIb-NA2); and even any unfound human FcγR or FcγR isoform or allotype. FcγR includes human, mouse, rat, rabbit, and monkey Fcγ receptors. The FcγR of the present invention is not limited to these receptors and may be derived from any organism. The mouse FcγR includes, but is not limited to, FcγRI (CD64), FcγRII (CD32), FcγRIII (CD16), and FcγRIII-2 (FcγRIV, CD16-2), and even any unfound mouse FcγR or FcγR isoform or allotype. Preferred examples of such Fcγ receptors include human FcγRI (CD64), FcγRIIa (CD32), FcγRIIb (CD32), FcγRIIIa (CD16), and/or FcγRIIIb (CD16). The polypeptide sequence of human FcγRI is described in SEQ ID NO: 78 (NP_000557.1); the polypeptide sequence of human FcγRIIa (allotype H131) is described in SEQ ID NO: 79 (AAH20823.1) (allotype R131 has a sequence having Arg replaced for an amino acid at position 166 in SEQ ID NO: 79); the polypeptide sequence of FcγRIIb is described in SEQ ID NO: 80 (AAI46679.1); the polypeptide sequence of FcγRIIIa is described in SEQ ID NO: 81 (AAH33678.1); and the polypeptide sequence of FcγRIIIb is described in SEQ ID NO: 82 (AAI28563.1) (registration numbers of a database such as RefSeq are shown within the parentheses). Whether or not the Fcγ receptor has binding activity against the Fc region of an IgG1, IgG2, IgG3, or IgG4 monoclonal antibody can be confirmed by a method known in the art such as FACS or ELISA formats as well as BIACORE method using amplified luminescent proximity homogeneous assay (ALPHA) screening or surface plasmon resonance (SPR) phenomena (Proc. Natl. Acad. Sci. U.S.A. (2006) 103 (11), 4005-4010).

In FcγRI (CD64) including isoforms FcγRIa, FcγRIb, and FcγRIc and FcγRIII (CD16) including isoforms FcγRIIIa (including allotypes V158 and F158) and FcγRIIIb (including allotypes FcγRIIIb-NA1 and FcγRIIIb-NA2), an α chain binding to the IgG Fc region associates with a common γ chain having ITAM that transduces activating signals into cells. On the other hand, FcγRII (CD32) including isoforms FcγRIIa (including allotypes H131 and R131) and FcγRIIc contains ITAM in its cytoplasmic domain. These receptors are expressed in many immunocytes, such as macrophages, mast cells, and antigen-presenting cells. These receptors bind to IgG Fc regions and thereby transduce activating signals, which in turn promote the phagocytic capacity of macrophages, the production of inflammatory cytokines, the degranulation of mast cells, and the increased function of antigen-presenting cells. In the present specification, the Fcγ receptors that are able to transduce activating signals as described above are referred to as active Fcγ receptors.

On the other hand, FcγRIIb (including FcγRIIb-1 and FcγRIIb-2) contains ITIM that transduces inhibitory signals, in its intracytoplasmic domain. In B cells, activating signals from B cell receptors (BCRs) are inhibited by the cross-linking of BCR with FcγRIIb, resulting in the suppressed antibody production of BCR. The phagocytic capacity of macrophages or their ability to produce inflammatory cytokines is suppressed by the cross-linking of FcγRIII and FcγRIIb. In the present specification, the Fcγ receptors that are able to transduce inhibitory signals as described above are referred to as inhibitory Fcγ receptors.

Binding Activity of Fc Region Against FcγR

As mentioned above, examples of the Fc region contained in the anti-GPC3 antibody of the present invention include Fc regions having binding activity against Fcγ receptors. In a non-limiting aspect, examples of such Fc regions include Fc regions contained in constant regions represented by SEQ ID NO: 74 for human IgG1, SEQ ID NO: 75 for IgG2, SEQ ID NO: 76 for IgG3, and SEQ ID NO: 77 for IgG4. Whether or not the Fcγ receptor has binding activity against the Fc region of an IgG1, IgG2, IgG3, or IgG4 monoclonal antibody can be confirmed by a method known in the art such as FACS or ELISA formats as well as BIACORE method using amplified luminescent proximity homogeneous assay (ALPHA) screening or surface plasmon resonance (SPR) phenomena (Proc. Natl. Acad. Sci. U.S.A. (2006) 103 (11), 4005-4010).

The ALPHA screening is carried out on the basis of the following principles according to ALPHA technology using two beads, a donor and an acceptor. Luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen in an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Therefore, no chemiluminescent reaction occurs.

For example, a biotin-labeled anti-GPC3 antibody comprising the Fc region is bound to the donor bead, while a glutathione S transferase (GST)-tagged Fcγ receptor is bound to the acceptor bead. In the absence of a competing anti-GPC3 antibody comprising a modified Fc region, the anti-GPC3 antibody having the native Fc region interacts with the Fcγ receptor to generate signals of 520 to 620 nm. An anti-GPC3 antibody comprising an untagged modified Fc region competes with the anti-GPC3 antibody having the native Fc region for the interaction with the Fcγ receptor. Decrease in fluorescence caused as a result of the competition can be quantified to thereby determine relative binding affinity. The antibody biotinylation using sulfo-NHS-biotin or the like is known in the art. For the tagging of the Fcγ receptor with GST, a method can be appropriately adopted, which involves, for example: fusing a polynucleotide encoding the Fcγ receptor in flame with a polynucleotide encoding GST; operably ligating the resulting fusion gene with a vector; and allowing cells or the like carrying the vector to express the GST-tagged Fcγ receptor, which is then purified using a glutathione column. The obtained signals are preferably analyzed using, for example, software GRAPHPAD PRISM (GraphPad Software, Inc., San Diego) adapted to a one-site competition model based on nonlinear regression analysis.

One (ligand) of the substances between which the interaction is to be observed is immobilized on a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is flowed on the surface of the sensor chip and bound to the ligand so that the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). Kinetics: an association rate constant (ka) and a dissociation rate constant (kd) are determined from the curve of the sensorgram, and affinity (KD) is determined from the ratio between these constants. Inhibition assay is also preferably used in the BIACORE method. Examples of the inhibition assay are described in Lazor et al. (Proc. Natl. Acad. Sci. U.S.A. (2006) 103 (11), 4005-4010).

Fcγ Receptor (FcγR)-Binding Modified Fc Region

Instead of the Fc regions contained in constant regions represented by SEQ ID NO: 74 for human IgG1, SEQ ID NO: 75 for IgG2, SEQ ID NO: 76 for IgG3, and SEQ ID NO: 77 for IgG4, an FcγR-binding modified Fc region having higher binding activity against Fcγ receptors than that of the Fc region of native human IgG against Fcγ receptors may be appropriately used as the Fc region contained in the anti-GPC3 antibody of the present invention. In the present specification, the "Fc region of native human IgG" means an Fc region having a fucose-containing sugar chain as a sugar chain bound to position 297 (EU numbering) of the Fc region contained in the human IgG1, IgG2, IgG3, or IgG4 constant region represented by SEQ ID NO: 74, 75, 76, or 77. Such an FcγR-binding modified Fc region can be prepared by the amino acid alteration of the native human IgG Fc region. Whether or not the FcγR-binding modified Fc region has higher binding activity against FcγR than that of the native human IgG Fc region against FcγR can be appropriately confirmed by a method known in the art such as FACS or ELISA formats as well as BIACORE method using amplified luminescent proximity homogeneous assay (ALPHA) screening or surface plasmon resonance (SPR) phenomena as described above.

In the present invention, the "alteration of amino acid(s)" or "amino acid alteration" of the Fc region includes alteration to an amino acid sequence different from the amino acid sequence of the starting Fc region. Any Fc region can be used as the starting Fc region as long as the modified form of the starting Fc region can bind to the human Fcγ receptor in a neutral region of pH. Alternatively, an Fc region further modified from an already modified Fc region as the starting Fc region may be preferably used as the Fc region of the present invention. The starting Fc region may mean the polypeptide itself, a composition containing the starting Fc region, or an amino acid sequence encoding the starting Fc region. The starting Fc region can include Fc regions known in the art produced by recombination reviewed in the paragraph about the antibody. The starting Fc region is not limited by its origin and can be obtained from an arbitrary nonhuman animal organism or a human. Preferred examples of the arbitrary organism include an organism selected from mice, rats, guinea pigs, hamsters, gerbils, cats, rabbits, dog, goats, sheep, cattle, horses, camels, and nonhuman primates. In another aspect, the starting Fc region can be obtained from a cynomolgus monkey, a marmoset, a rhesus monkey, a chimpanzee, or a human. Preferably, the starting Fc region can be obtained from human IgG1, though the starting Fc region is not limited by a particular class of IgG. This means that the Fc region of human IgG1, IgG2, IgG3, or IgG4 can be appropriately used as the starting Fc region. Likewise, in the present specification, this means that the Fc region of arbitrary IgG class or subclass from the arbitrary organism can be preferably used as the starting Fc region. Examples of variants of naturally occurring IgG or manipulated forms thereof are described in literatures known in the art (Curr. Opin. Biotechnol. (2009) 20 (6), 685-91, Curr. Opin. Immunol. (2008) 20 (4), 460-470, Protein Eng. Des. Sel. (2010) 23 (4), 195-202, International Publication Nos. WO2009/086320, WO2008/092117, WO2007/041635, and WO2006/105338) though the variants or the manipulated forms are not limited to those described therein.

Examples of the alteration include one or more variation(s), for example, a variation that substitutes amino acid(s) in the starting Fc region by amino acid residue(s) different therefrom, the insertion of one or more amino acid residue(s) into the amino acid sequence of the starting Fc region, and the deletion of one or more amino acid(s) from the amino acid sequence of the starting Fc region. Preferably, the amino acid sequence of the Fc region thus modified comprises an amino acid sequence containing at least a non-natural portion of the Fc region. Such a variant inevitably has less than 100% sequence identity or similarity to the starting Fc region. In a preferred embodiment, the variant has an amino acid sequence with approximately 75% to less than 100% sequence identity or similarity, more preferably approximately 80% to less than 100%, further preferably approximately 85% to less than 100%, still further preferably approximately 90% to less than 100%, most preferably approximately 95% to less than 100% sequence identity or similarity to the amino acid sequence of the starting Fc region. In a non-limiting aspect of the present invention, the starting Fc region and the FcγR-binding modified Fc region of the present invention differ by at least one amino acid. The difference in amino acid between the starting Fc region and the FcγR-binding modified Fc region of the present invention may be preferably determined by a difference in amino acid with the identified position of its amino acid residue defined particularly by the EU numbering mentioned above.

For the amino acid alteration of the Fc region, a method known in the art can be appropriately adopted, such as site-directed mutagenesis (Kunkel et al., Proc. Natl. Acad. Sci. USA (1985) 82, 488-492) or overlap extension PCR. Also, a plurality of methods known in the art can be adopted as methods for altering an amino acid to substitute the amino acid by an amino acid other than natural one (Annu. Rev. Biophys. Biomol. Struct. (2006) 35, 225-249; and Proc. Natl. Acad. Sci. U.S.A. (2003) 100 (11), 6353-6357). For example, a tRNA-containing cell-free translation system (Clover Direct (Protein Express, an R & D oriented company)) comprising a non-natural amino acid bound with an amber suppressor tRNA complementary to UAG codon (amber codon), which is a stop codon, is also preferably used.

The FcγR-binding modified Fc region (contained in the antigen-binding molecule of the present invention) having higher binding activity against Fcγ receptors than that of the native human IgG Fc region against Fcγ receptors can be obtained by any method. Specifically, the FcγR-binding modified Fc region can be obtained by the amino acid alteration of a human IgG immunoglobulin Fc region used as the starting Fc region. Examples of the IgG immunoglobulin Fc region preferred for the alteration include Fc regions contained in human IgG (IgG1, IgG2, IgG3, and IgG4, and modified forms thereof) constant regions represented by, for example, SEQ ID NOs: 74, 75, 76, and 77.

The alteration to other amino acids can be amino acid alteration at any position as long as the resulting Fc region has higher binding activity against Fcγ receptors than that of the native human IgG Fc region against Fcγ receptors. When the antigen-binding molecule contains a human IgG1 Fc region as a human Fc region, the alteration contained therein is preferably effective for producing higher binding activity against Fcγ receptors than that of the native human IgG Fc region having a fucose-containing sugar chain as a sugar chain bound to position 297 (EU numbering) against Fcγ receptors. Such amino acid alteration has been reported in, for example, International Publication Nos. WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260 and WO2006/023403.

Examples of the amino acid that may undergo such alteration include at least one or more amino acid(s) selected from the group of position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440 based on the EU numbering. The alteration of these amino acids can yield the Fc region (FcγR-binding modified Fc region) having higher binding activity against Fcγ receptors than that of the native human IgG Fc region against Fcγ receptors.

Particularly preferred examples of the alteration used in the present invention include at least one or more amino acid alteration(s) selected from the group of alterations of
an amino acid at position 221 to Lys or Tyr,
an amino acid at position 222 to Phe, Trp, Glu, or Tyr,
an amino acid at position 223 to Phe, Trp, Glu, or Lys,
an amino acid at position 224 to Phe, Trp, Glu, or Tyr,
an amino acid at position 225 to Glu, Lys, or Trp,
an amino acid at position 227 to Glu, Gly, Lys, or Tyr,
an amino acid at position 228 to Glu, Gly, Lys, or Tyr,
an amino acid at position 230 to Ala, Glu, Gly, or Tyr,
an amino acid at position 231 to Glu, Gly, Lys, Pro, or Tyr,
an amino acid at position 232 to Glu, Gly, Lys, or Tyr,
an amino acid at position 233 to Ala, Asp, Phe, Gly, His, Ile, Lys, Leu, Met, Asn, Gln, Arg, Ser, Thr, Val, Trp, or Tyr,
an amino acid at position 234 to Ala, Asp, Glu, Phe, Gly, His, Ile, Lys, Met, Asn, Pro, Gln, Arg, Ser, Thr, Val, Trp, or Tyr,
an amino acid at position 235 to Ala, Asp, Glu, Phe, Gly, His, Ile, Lys, Met, Asn, Pro, Gln, Arg, Ser, Thr, Val, Trp, or Tyr,
an amino acid at position 236 to Ala, Asp, Glu, Phe, His, Ile, Lys, Leu, Met, Asn, Pro, Gln, Arg, Ser, Thr, Val, Trp, or Tyr,
an amino acid at position 237 to Asp, Glu, Phe, His, Ile, Lys, Leu, Met, Asn, Pro, Gln, Arg, Ser, Thr, Val, Trp, or Tyr, an amino acid at position 238 to Asp, Glu, Phe, Gly, His, Ile, Lys, Leu, Met, Asn, Gln, Arg, Ser, Thr, Val, Trp, or Tyr,
an amino acid at position 239 to Asp, Glu, Phe, Gly, His, Ile, Lys, Leu, Met, Asn, Pro, Gln, Arg, Thr, Val, Trp, or Tyr,
an amino acid at position 240 to Ala, Ile, Met, or Thr,
an amino acid at position 241 to Asp, Glu, Leu, Arg, Trp, or Tyr,
an amino acid at position 243 to Leu, Glu, Leu, Gln, Arg, Trp, or Tyr,
an amino acid at position 244 to His,
an amino acid at position 245 to Ala,
an amino acid at position 246 to Asp, Glu, His, or Tyr,
an amino acid at position 247 to Ala, Phe, Gly, His, Ile, Leu, Met, Thr, Val, or Tyr,
an amino acid at position 249 to Glu, His, Gln, or Tyr,
an amino acid at position 250 to Glu or Gln,
an amino acid at position 251 to Phe,
an amino acid at position 254 to Phe, Met, or Tyr,
an amino acid at position 255 to Glu, Leu, or Tyr,
an amino acid at position 256 to Ala, Met, or Pro,
an amino acid at position 258 to Asp, Glu, His, Ser, or Tyr,
an amino acid at position 260 to Asp, Glu, His, or Tyr,
an amino acid at position 262 to Ala, Glu, Phe, Ile, or Thr,
an amino acid at position 263 to Ala, Ile, Met, or Thr,
an amino acid at position 264 to Asp, Glu, Phe, Gly, His, Ile, Lys, Leu, Met, Asn, Pro, Gln, Arg, Ser, Thr, Trp, or Tyr,
an amino acid at position 265 to Ala, Leu, Phe, Gly, His, Ile, Lys, Leu, Met, Asn, Pro, Gln, Arg, Ser, Thr, Val, Trp, or Tyr,
an amino acid at position 266 to Ala, Ile, Met, or Thr,
an amino acid at position 267 to Asp, Glu, Phe, His, Ile, Lys, Leu, Met, Asn, Pro, Gln, Arg, Thr, Val, Trp, or Tyr,
an amino acid at position 268 to Asp, Glu, Phe, Gly, Ile, Lys, Leu, Met, Pro, Gln, Arg, Thr, Val, or Trp,
an amino acid at position 269 to Phe, Gly, His, Ile, Lys, Leu, Met, Asn, Pro, Arg, Ser, Thr, Val, Trp, or Tyr,
an amino acid at position 270 to Glu, Phe, Gly, His, Ile, Leu, Met, Pro, Gln, Arg, Ser, Thr, Trp, or Tyr,
an amino acid at position 271 to Ala, Asp, Glu, Phe, Gly, His, Ile, Lys, Leu, Met, Asn, Gln, Arg, Ser, Thr, Val, Trp, or Tyr,
an amino acid at position 272 to Asp, Phe, Gly, His, Ile, Lys, Leu, Met, Pro, Arg, Ser, Thr, Val, Trp, or Tyr,
an amino acid at position 273 to Phe or Ile,
an amino acid at position 274 to Asp, Glu, Phe, Gly, His, Ile, Leu, Met, Asn, Pro, Arg, Ser, Thr, Val, Trp, or Tyr,
an amino acid at position 275 to Leu or Trp,
an amino acid at position 276 to Asp, Glu, Phe, Gly, His, Ile, Leu, Met, Pro, Arg, Ser, Thr, Val, Trp, or Tyr,
an amino acid at position 278 to Asp, Glu, Gly, His, Ile, Lys, Leu, Met, Asn, Pro, Gln, Arg, Ser, Thr, Val, or Trp,
an amino acid at position 279 to Ala,
an amino acid at position 280 to Ala, Gly, His, Lys, Leu, Pro, Gln, Trp, or Tyr,
an amino acid at position 281 to Asp, Lys, Pro, or Tyr,
an amino acid at position 282 to Glu, Gly, Lys, Pro, or Tyr,
an amino acid at position 283 to Ala, Gly, His, Ile, Lys, Leu, Met, Pro, Arg, or Tyr,
an amino acid at position 284 to Asp, Glu, Leu, Asn, Thr, or Tyr,
an amino acid at position 285 to Asp, Glu, Lys, Gln, Trp, or Tyr,
an amino acid at position 286 to Glu, Gly, Pro, or Tyr,
an amino acid at position 288 to Asn, Asp, Glu, or Tyr,
an amino acid at position 290 to Asp, Gly, His, Leu, Asn, Ser, Thr, Trp, or Tyr,
an amino acid at position 291 to Asp, Glu, Gly, His, Ile, Gln, or Thr,
an amino acid at position 292 to Ala, Asp, Glu, Pro, Thr, or Tyr,
an amino acid at position 293 to Phe, Gly, His, Ile, Leu, Met, Asn, Pro, Arg, Ser, Thr, Val, Trp, or Tyr,
an amino acid at position 294 to Phe, Gly, His, Ile, Lys, Leu, Met, Asn, Pro, Arg, Ser, Thr, Val, Trp, or Tyr,
an amino acid at position 295 to Asp, Glu, Phe, Gly, His, Ile, Lys, Met, Asn, Pro, Arg, Ser, Thr, Val, Trp, or Tyr,
an amino acid at position 296 to Ala, Asp, Glu, Gly, His, Ile, Lys, Leu, Met, Asn, Gln, Arg, Ser, Thr, or Val,
an amino acid at position 297 to Asp, Glu, Phe, Gly, His, Ile, Lys, Leu, Met, Pro, Gln, Arg, Ser, Thr, Val, Trp, or Tyr,
an amino acid at position 298 to Ala, Asp, Glu, Phe, His, Ile, Lys, Met, Asn, Gln, Arg, Thr, Val, Trp, or Tyr,
an amino acid at position 299 to Ala, Asp, Glu, Phe, Gly, His, Ile, Lys, Leu, Met, Asn, Pro, Gln, Arg, Ser, Val, Trp, or Tyr,
an amino acid at position 300 to Ala, Asp, Glu, Gly, His, Ile, Lys, Leu, Met, Asn, Pro, Gln, Arg, Ser, Thr, Val, or Trp,
an amino acid at position 301 to Asp, Glu, His, or Tyr,
an amino acid at position 302 to Ile,
an amino acid at position 303 to Asp, Gly, or Tyr,
an amino acid at position 304 to Asp, His, Leu, Asn, or Thr,
an amino acid at position 305 to Glu, Ile, Thr, or Tyr,
an amino acid at position 311 to Ala, Asp, Asn, Thr, Val, or Tyr,
an amino acid at position 313 to Phe,
an amino acid at position 315 to Leu,
an amino acid at position 317 to Glu or Gln,
an amino acid at position 318 to His, Leu, Asn, Pro, Gln, Arg, Thr, Val, or Tyr,
an amino acid at position 320 to Asp, Phe, Gly, His, Ile, Leu, Asn, Pro, Ser, Thr, Val, Trp, or Tyr,
an amino acid at position 322 to Ala, Asp, Phe, Gly, His, Ile, Pro, Ser, Thr, Val, Trp, or Tyr,
an amino acid at position 323 to Ile,
an amino acid at position 324 to Asp, Phe, Gly, His, Ile, Leu, Met, Pro, Arg, Thr, Val, Trp, or Tyr,
an amino acid at position 325 to Ala, Asp, Glu, Phe, Gly, His, Ile, Lys, Leu, Met, Pro, Gln, Arg, Ser, Thr, Val, Trp, or Tyr,
an amino acid at position 326 to Ala, Asp, Glu, Gly, Ile, Leu, Met, Asn, Pro, Gln, Ser, Thr, Val, Trp, or Tyr,
an amino acid at position 327 to Ala, Asp, Glu, Phe, Gly, His, Ile, Lys, Leu, Met, Asn, Pro, Arg, Thr, Val, Trp, or Tyr,
an amino acid at position 328 to Ala, Asp, Glu, Phe, Gly, His, Ile, Lys, Met, Asn, Pro, Gln, Arg, Ser, Thr, Val, Trp, or Tyr,
an amino acid at position 329 to Asp, Glu, Phe, Gly, His, Ile, Lys, Leu, Met, Asn, Gln, Arg, Ser, Thr, Val, Trp, or Tyr,
an amino acid at position 330 to Cys, Glu, Phe, Gly, His, Ile, Lys, Leu, Met, Asn, Pro, Arg, Ser, Thr, Val, Trp, or Tyr,
an amino acid at position 331 to Asp, Phe, His, Ile, Leu, Met, Gln, Arg, Thr, Val, Trp, or Tyr,
an amino acid at position 332 to Ala, Asp, Glu, Phe, Gly, His, Lys, Leu, Met, Asn, Pro, Gln, Arg, Ser, Thr, Val, Trp, or Tyr,
an amino acid at position 333 to Ala, Asp, Glu, Phe, Gly, His, Ile, Leu, Met, Pro, Ser, Thr, Val, or Tyr,
an amino acid at position 334 to Ala, Glu, Phe, Ile, Leu, Pro, or Thr,
an amino acid at position 335 to Asp, Phe, Gly, His, Ile, Leu, Met, Asn, Pro, Arg, Ser, Val, Trp, or Tyr,
an amino acid at position 336 to Glu, Lys, or Tyr, an amino acid at position 337 to Glu, His, or Asn,
an amino acid at position 339 to Asp, Phe, Gly, Ile, Lys, Met, Asn, Gln, Arg, Ser, or Thr,
   an amino acid at position 376 to Ala, or Val,
   an amino acid at position 377 to Gly, or Lys,
   an amino acid at position 378 to Asp,
   an amino acid at position 379 to Asn,
   an amino acid at position 380 to Ala, Asn, or Ser,
   an amino acid at position 382 to Ala, or Ile,
   an amino acid at position 385 to Glu,
   an amino acid at position 392 to Thr,
   an amino acid at position 396 to Leu,
   an amino acid at position 421 to Lys,
   an amino acid at position 427 to Asn,
   an amino acid at position 428 to Phe, or Leu,
   an amino acid at position 429 to Met,
   an amino acid at position 434 to Trp,
   an amino acid at position 436 to Ile, or
   an amino acid at position 440 to Gly, His, Ile, Leu, or Tyr, based on the EU numbering in the Fc region. The number of amino acids to be altered is not particularly limited. Only one amino acid may be altered, or two or more amino acids may be altered. Examples of combinations of amino acid alterations at two or more positions include combinations as described in Table 3 (Tables 3-1 to 3-3). Also, WO2007/047291 discloses specific examples of the anti-GPC3 antibody comprising the FcγR-binding modified Fc region having higher binding activity against Fcγ receptors than that of the native human IgG Fc region against Fcγ receptors.

TABLE 3-1

| Combination of amino acids | Combination of amino acids |
| --- | --- |
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327I/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |
| TABLE 3-2 | |
| F243L/V264I | S239D/N297D/I332E |
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |
| L234E/I332E | S239N/A330L/I332E |

TABLE 3-1-continued

| Combination of amino acids | Combination of amino acids |
| --- | --- |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |
| TABLE 3-3 | |
| L328Y/I332E | S239D/A330Y/I332E/V240I |
| N297D/I332E | S239D/A330Y/I332E/V264T |
| N297E/I332E | S239D/A330Y/I332E/V266I |
| N297S/I332E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239D/D265G | S239D/I332E/H268E/A330Y |
| S239D/D265N | S239D/N297D/I332E/A330Y |
| S239D/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239E/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |
| S267E/L328F | G236D/S267E |
| S239D/S267E | |

Acidic to neutral regions of pH can be appropriately used as pH conditions under which the Fcγ receptor-binding domain contained in the anti-GPC3 antibody of the present invention is assayed for its binding activity against the Fcγ receptor. The acidic to neutral regions of pH as the conditions under which the Fcγ receptor-binding domain contained in the antigen-binding molecule of the present invention is assayed for its binding activity against the Fcγ receptor usually mean pH 5.8 to pH 8.0. The pH range is preferably indicated by arbitrary pH values from pH 6.0 to pH 7.4 and is preferably selected from pH 6.0, 6.1, 6.2, 6.3, 6.4, 6.5, 6.6, 6.7, 6.8, 6.9, 7.0, 7.1, 7.2, 7.3, and 7.4. Particularly, a pH range of 6.15 to 7.4, which is close to the pH of cancer tissues, is preferred (Vaupel et al., Cancer Res. (1989) 49, 6449-6665). The binding affinity of the Fc region for the human Fcγ receptor can be evaluated under assay conditions involving an arbitrary temperature of 10° C. to 50° C. Preferably, a temperature of 15° C. to 40° C. is used for determining the binding affinity of the Fc region for the human Fcγ receptor. More preferably, an arbitrary temperature of 20° C. to 35° C., for example, any one temperature of 20, 21, 22, 23, 24, 25, 26, 27, 28, 29, 30, 31, 32, 33, 34, and 35° C., is also used for determining the binding affinity of the Fc region for the Fcγ receptor. The temperature 25° C. is one non-limiting example in an aspect of the present invention.

In the present specification, the higher binding activity of the FcγR-binding modified Fc region against Fcγ receptors than that of the native Fc region against Fcγ receptors means that the binding activity of the FcγR-binding modified Fc region against any of the human Fcγ receptors FcγRI, FcγRIIa, FcγRIIb, FcγRIIIa, and/or FcγRIIIb is higher than that of the native Fc region against the human Fcγ receptor. This means that, for example, on the basis of the analysis method described above, the anti-GPC3 antibody comprising the FcγR-binding modified Fc region exhibits binding activity of 105% or more, preferably 110% or more, 115% or more, 120% or more, or 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, 2 or more times, 2.5 or more times, 3 or more times, 3.5 or more times, 4 or more times, 4.5 or more times, 5 or more times, 7.5 or more times, 10 or more times, 20 or more times, 30 or more times, 40 or more times, 50 or more times, 60 or more times, 70 or more times, 80 or more times, 90 or more times, or 100 or more times, as compared with the binding activity of an anti-GPC3 antibody comprising the native Fc region of human IgG serving as a control. The native Fc region used may be the starting Fc region or may be the native Fc region of an antibody of the same subclass as the anti-GPC3 antibody concerned.

In the present invention, a native human IgG Fc region having a fucose-containing sugar chain as a sugar chain bound to an amino acid at position 297 (EU numbering) is preferably used as the native Fc region of human IgG serving as a control. Whether or not the sugar chain bound to an amino acid at position 297 (EU numbering) is a fucose-containing sugar chain can be confirmed using an approach known in the art. Whether or not the sugar chain bound to the native human IgG Fc region is a fucose-containing sugar chain can be determined by, for example, a method as given below. The native human IgG to be tested liberates a sugar chain through its reaction with N-Glycosidase F (Roche Diagnostics K.K.) (Weitzhandler et al., J. Pharma. Sciences (1994) 83, 12, 1670-1675). Next, proteins are removed through reaction with ethanol, and the resulting reaction solution (Schenk et al., J. Clin. Investigation (2001) 108 (11) 1687-1695) is concentrated to dryness and then fluorescently labeled with 2-aminobenzamide (Bigge et al., Anal. Biochem. (1995) 230 (2) 229-238). After removal of the reagent by solid-phase extraction using a cellulose cartridge, the 2-AB-fluorescently labeled sugar chain is analyzed by normal-phase chromatography. The detected peak in the chromatogram can be observed to thereby determine whether or not the sugar chain bound to the native Fc region of human IgG is a fucose-containing sugar chain.

An anti-GPC3 antibody having an IgG monoclonal antibody Fc region can be appropriately used as the anti-GPC3 antibody comprising the native Fc region of an antibody of the same subclass serving as a control. Structural examples of the Fc region include Fc regions contained in constant regions represented by SEQ ID NOs: 74 (having A added to the N terminus of the sequence of database registration No. AAC82527.1), 75 (having A added to the N terminus of the sequence of database registration No. AAB59393.1), 76 (database registration No. CAA27268.1), and 77 (having A added to the N terminus of the sequence of database registration No. AAB59394.1). In the case of using a certain isotype of anti-GPC3 antibody as a test substance, the anti-GPC3 antibody comprising the Fc region to be tested is studied for its effect of binding activity against Fcγ receptors by using an anti-GPC3 antibody of the certain isotype as a control. The anti-GPC3 antibody comprising the Fc region thus confirmed to have higher binding activity against Fcγ receptors is appropriately selected.

Fc Region Having Higher Binding Activity Against Active Fcγ Receptor than its Binding Activity Against Inhibitory Fcγ Receptor As described above, preferred examples of the active Fcγ receptors include FcγRI (CD64) including FcγRIa, FcγRIb, and FcγRIc, FcγRIIa, and FcγRIII (CD16) including isoforms FcγRIIIa (including allotypes V158 and F158) and FcγRIIIb (including allotypes FcγRIIIb-NA1 and FcγRIIIb-NA2). Preferred examples of the inhibitory Fcγ receptors include FcγRIIb (including FcγRIIb-1 and FcγRIIb-2).

In a non-limiting aspect, examples of the anti-GPC3 antibody of the present invention include an anti-GPC3 antibody comprising an Fc region having higher binding activity against active Fcγ receptors than its binding activity against inhibitory Fcγ receptors. In this case, the higher binding activity against active Fcγ receptors than its binding activity against inhibitory Fcγ receptors means that the binding activity of the Fc region against any of the human Fcγ receptors FcγRIa, FcγRIIa, FcγRIIIa, and/or FcγRIIIb is higher than its binding activity against FcγRIIb. This means that, for example, on the basis of the analysis method described above, the antigen-binding molecule comprising the Fc region exhibits binding activity of 105% or more, preferably 110% or more, 120% or more, 130% or more, or 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10 or more times, 20 or more times, 30 or more times, 40 or more times, 50 times, 60 times, 70 times, 80 times, 90 times, or 100 or more times against any of the human Fcγ receptors FcγRIa, FcγRIIa, FcγRIIIa, and/or FcγRIIIb, as compared with its binding activity against FcγRIIb. An IgG antibody comprising such an Fc region is known to have enhancement in the ADCC activity mentioned above. Thus, the anti-GPC3 antibody comprising the Fc region is useful as the GPC3-targeting therapeutic agent of the present invention.

In a non-limiting aspect of the present invention, examples of the Fc region having higher binding activity against active Fcγ receptors than its binding activity against inhibitory Fcγ receptors (having selective binding activity against active Fcγ receptors) preferably include Fc regions in which at least one or more amino acid(s) selected from the group of position 221, position 222, position 223, position 224, position 225, position 227, position 228, position 230, position 231, position 232, position 233, position 234, position 235, position 236, position 237, position 238, position 239, position 240, position 241, position 243, position 244, position 245, position 246, position 247, position 249, position 250, position 251, position 254, position 255, position 256, position 258, position 260, position 262, position 263, position 264, position 265, position 266, position 267, position 268, position 269, position 270, position 271, position 272, position 273, position 274, position 275, position 276, position 278, position 279, position 280, position 281, position 282, position 283, position 284, position 285, position 286, position 288, position 290, position 291, position 292, position 293, position 294, position 295, position 296, position 297, position 298, position 299, position 300, position 301, position 302, position 303, position 304, position 305, position 311, position 313, position 315, position 317, position 318, position 320, position 322, position 323, position 324, position 325, position 326, position 327, position 328, position 329, position 330, position 331, position 332, position 333, position 334, position 335, position 336, position 337, position 339, position 376, position 377, position 378, position 379, position 380, position 382, position 385, position 392, position 396, position 421, position 427, position 428, position 429, position 434, position 436 and position 440 (EU numbering) mentioned above is altered to an amino acid different from that in the native Fc region.

In a non-limiting aspect of the present invention, examples of the Fc region having higher binding activity against active Fcγ receptors than its binding activity against inhibitory Fcγ receptors (having selective binding activity against active Fcγ receptors) preferably include Fc regions in which a plurality of amino acids described in Tables 3-1 to 3-3 are altered to amino acids different from those in the native Fc region.

Fc Region Having Modified Sugar Chain

The Fc region contained in the anti-GPC3 antibody provided by the present invention can also include an Fc region modified such that a higher proportion of fucose-deficient sugar chains is bound to the Fc region or a higher proportion of bisecting N-acetylglucosamine is added to the Fc region in the composition of sugar chains bound to the Fc region. The removal of a fucose residue from N-acetylglucosamine at the reducing end of a N-glycoside-linked complex sugar chain bound to an antibody Fc region is known to enhance its affinity for FcγRIIIa (Sato et al., Expert Opin. Biol. Ther. (2006) 6 (11), 1161-1173). An IgG1 antibody comprising such an Fc region is known to have enhancement in the ADCC activity. Thus, the antigen-binding molecule comprising the Fc region is also useful as the antigen-binding molecule contained in the pharmaceutical composition of the present invention. Examples of the antibody that lacks a fucose residue in N-acetylglucosamine at the reducing end of a N-glycoside-linked complex sugar chain bound to the antibody Fc region include the following antibodies: glycosylated antibodies (e.g., International Publication No. WO1999/054342); and antibodies deficient in fucose added to the sugar chain (e.g., International Publication Nos. WO2000/061739, WO2002/031140, and WO2006/067913). Also, WO2006/046751 and WO2009/041062 describe specific examples of the anti-GPC3 antibody comprising the Fc region modified such that a higher proportion of fucose-deficient sugar chains is bound to the Fc region or a higher proportion of bisecting N-acetylglucosamine is added to the Fc region in the composition of sugar chains bound to the Fc region.

More specifically, in an alternative non-limiting aspect, in order to prepare the antibody deficient in fucose added to the sugar chain (e.g., International Publication Nos. WO2000/061739, WO2002/031140, and WO2006/067913) as the antibody that lacks a fucose residue in N-acetylglucosamine at the reducing end of a N-glycoside-linked complex sugar chain bound to the antibody Fc region, host cells less able to add fucose to sugar chains are prepared as a result of altering the activity of forming the sugar chain structures of polypeptides that undergo sugar chain modification. The host cells are allowed to express the desired antibody gene, and the antibody deficient in fucose in its sugar chain can be recovered from the culture solution of the host cells. Non-limiting preferred examples of the activity of forming the sugar chain structures of polypeptides can include the activity of an enzyme or a transporter selected from the group consisting of fucosyltransferase (EC 2.4.1.152), fucose transporter (SLC35C1), GMD (GDP-mannose 4,6-dehydratase) (EC 4.2.1.47), Fx (GDP-keto-6-deoxymannose 3,5-epimerase/4-reductase) (EC 1.1.1.271), and GFPP (GDP-β-L-fucose pyrophosphorylase) (EC 2.7.7.30). These enzymes or transporters are not necessarily limited by their structures as long as the enzymes or the transporters can exert their activity. In the present specification, these proteins capable of exerting such activity are referred to as functional proteins. In a non-limiting aspect, examples of methods for altering the activity include the deletion of the activity. For the preparation of host cells that lack the activity, a method known in the art can be appropriately adopted, such as a method which involves disrupting the genes of these functional proteins to render the genes unfunctional (e.g., International Publication Nos. WO2000/061739, WO2002/031140, and WO2006/067913). Such host cells that lack the activity can be prepared by, for example, a method which involves disrupting the endogenous genes of these functional proteins in cells such as CHO cells, BHK cells, NS0 cells, SP2/0 cells, YO myeloma cells, P3X63 mouse myeloma cells, PER cells, PER C6 cells, HEK293 cells, or hybridoma cells to render the genes unfunctional.

Antibodies containing sugar chains having bisecting GlcNAc (e.g., International Publication No. WO2002/079255) are known in the art. In a non-limiting aspect, host cells expressing genes encoding functional proteins having GnTIII (β-1,4-mannosyl-glycoprotein 4-β-N-acetylglucosaminyltransferase) (EC 2.4.1.144) activity or GalT (β-1,4-galactosyltransferase) (EC 2.4.1.38) activity are prepared in order to prepare such an antibody containing sugar chains having bisecting GlcNAc. In another non-limiting preferred aspect, host cells coexpressing a gene encoding a functional protein having human ManII (mannosidase II) (3.2.1.114) activity, a gene encoding a functional protein having GnTI (β-1,2-acetylglucosaminyltransferase I) (EC 2.4.1.94) activity, a gene encoding a functional protein having GnTII (β-1,2-acetylglucosaminyltransferase II) (EC 2.4.1.143) activity, a gene encoding a functional protein having ManI (mannosidase I) (EC 3.2.1.113) activity, and an α-1,6-fucosyltransferase (EC 2.4.1.68) gene, in addition to the functional proteins described above, are prepared (International Publication Nos. WO2004/065540).

The host cells less able to add fucose to sugar chains and the host cells having the activity of forming sugar chains having bisecting GlcNAc structures as described above can be transduced with antibody gene-containing expression vectors to respectively prepare the antibody that lacks a fucose residue in N-acetylglucosamine at the reducing end of a N-glycoside-linked complex sugar chain bound to the antibody Fc region and the antibody having sugar chains having bisecting GlcNAc. The methods for producing these antibodies are also applicable to a method for producing the antigen-binding molecule comprising the Fc region modified such that a higher proportion of fucose-deficient sugar chains is bound to the Fc region or a higher proportion of bisecting N-acetylglucosamine is added to the Fc region in the composition of sugar chains bound to the Fc region of the present invention. The composition of sugar chains bound to the Fc region contained in the antigen-binding molecule of the present invention prepared by such a production method can be confirmed by the method described in the paragraph "Fcγ receptor (FcγR)-binding modified Fc region".

Anti-GPC3 Antibody Having Altered Isoelectric Point

In a non-limiting aspect, examples of the anti-GPC3 antibody used in the present invention also include an anti-GPC3 antibody having an amino acid residue altered to change its isoelectric point (pI). Preferred examples of the "alteration of the electric charge of an amino acid residue" in the anti-GPC3 antibody provided by the present invention are as follows: alteration to increase the pI value can be performed by, for example, at least one substitution selected from the substitution of Q by K at position 43, the substitution of D by N at position 52, and the substitution of Q by R at position 105 based on the Kabat numbering in the anti-GPC3 antibody heavy chain variable region represented by SEQ ID NO: 50, which is consequently altered to, for example, the amino acid sequence represented by SEQ ID NO: 67. Also, this alteration can be performed by, for example, at least one substitution selected from the substitution of E by Q at position 17, the substitution of Q by R at position 27, and the substitution of Q by R at position 105 based on the Kabat numbering in the anti-GPC3 antibody light chain variable region represented by SEQ ID NO: 51 or SEQ ID NO: 66, which is consequently altered to, for example, the amino acid sequence represented by SEQ ID NO: 68. On the other hand, alteration to decrease the pI value can be performed by at least one substitution selected from the substitution of K by T at position 19, the substitution of Q by E at position 43, the substitution of G by E at position 61, the substitution of K by S at position 62, the substitution of K by Q at position 64, and the substitution of G by D at position 65 based on the Kabat numbering in the anti-GPC3 antibody heavy chain variable region represented by SEQ ID NO: 50, which is consequently altered to, for example, the amino acid sequence represented by SEQ ID NO: 69 or SEQ ID NO: 71. Also, this alteration can be performed by, for example, at least one substitution selected from the substitution of R by Q at position 24, the substitution of Q by E at position 27, the substitution of K by T at position 74, the substitution of R by S at position 77, and the substitution of K by E at position 107 based on the Kabat numbering in the anti-GPC3 antibody light chain variable region represented by SEQ ID NO: 51 or SEQ ID NO: 66, which is consequently altered to, for example, the amino acid sequence represented by SEQ ID NO: 70, SEQ ID NO: 72, or SEQ ID NO: 73. Further examples of the alteration to decrease the pI value include the substitution of at least one amino acid selected from amino acids at positions 268, 274, 355, 356, 358, and 419 based on the EU numbering in the heavy chain constant region represented by SEQ ID NO: 74. Preferred examples of these substitutions can include at least one substitution selected from the substitution of H by Q at position 268, the substitution of K by Q at position 274, the substitution of R by Q at position 355, the substitution of D by E at position 356, the substitution of L by M at position 358, and the substitution of Q by E at position 419 based on the EU numbering in the heavy chain constant region represented by SEQ ID NO: 31. As a result of these substitutions, a chimera having human antibody IgG1 and IgG4 constant regions is constructed. Specifically, these substitutions can yield an antibody having the desired pI without influencing the immunogenicity of the modified antibody.

Alteration to Reduce Heterogeneity

An IgG constant region deficient in Gly at position 446 and Lys at position 447 based on the EU numbering in the IgG constant region represented by SEQ ID NO: 74, 75, 76, or 77 can also be used as the constant region contained in the anti-GPC3 antibody of the present invention. Deficiency in both of these amino acids can reduce heterogeneity derived from the terminus of the heavy chain constant region of the antibody.

Antibody Modification

The posttranslational modification of a polypeptide refers to chemical modification given to the polypeptide translated during polypeptide biosynthesis. Since the primary structure of an antibody is composed of a polypeptide, the anti-GPC3 antibody of the present invention also includes a modified form that has received the posttranslational modification of the polypeptide constituting the primary structure of the anti-GPC3 antibody. The posttranslational modification of a polypeptide can be broadly classified into the addition of a functional group, the addition of a polypeptide or a peptide (ISGylation, SUMOylation, or ubiquitination), the conversion of the chemical properties of an amino acid (silylation, deamination, or deamidation), and structural conversion (disulfidation or protease degradation). In a non-limiting aspect, examples of the posttranslational modification according to the present invention include the addition of a peptide or a functional group to an amino acid residue as a unit constituting the polypeptide. Examples of such modification can specifically include phosphorylation (serine, threonine, tyrosine, aspartic acid, etc.), glucosylation (serine, threonine, aspartic acid, etc.), acylation (lysine), acetylation (lysine), hydroxylation (lysine and proline), prenylation (cysteine), palmitoylation (cysteine), alkylation (lysine and arginine), polyglutamylation (glutamic acid), carboxylation (glutamic acid), polyglycylation (glutamic acid), citrullination (arginine), and succinimide formation (aspartic acid). For example, an anti-GPC3 antibody that has received the modification of N-terminal glutamine to pyroglutamic acid by pyroglutamylation is also included in the anti-GPC3 antibody of the present invention, as a matter of course. Also, for example, a posttranslationally modified anti-GPC3 antibody comprising heavy and light chains or heavy chains linked via a "disulfide bond", which means a covalent bond formed between two sulfur atoms is included in the anti-GPC3 antibody of the present invention. A thiol group contained in an amino acid cysteine can form a disulfide bond or crosslink with a second thiol group. In general IgG molecules, CH1 and CL regions are linked via a disulfide bond, and two polypeptides constituting heavy chains are linked via a disulfide bond between cysteine residues at positions 226 and 229 based on the EU numbering. A posttranslationally modified anti-GPC3 antibody having such a linkage via a disulfide bond is also included in the anti-GPC3 antibody of the present invention.

Efficacy of GPC3-Targeting Therapeutic Agent for Cancer

The phrase "efficacy of a GPC3-targeting therapeutic agent for cancer" or "GPC3-targeting therapeutic agent for cancer is effective" means that the GPC3-targeting therapeutic agent produces desired or beneficial effects on a patient diagnosed with cancer. The desired or beneficial effects can include: (1) the inhibition of the further growth or diffusion of cancer cells; (2) the killing of cancer cells; (3) the inhibition of cancer recurrence; (4) the alleviation, reduction, mitigation, or inhibition of cancer-related symptoms (pain, etc.) or reduction in the frequency of the symptoms; and (5) improvement in the survival rate of the patient. The inhibition of cancer recurrence includes the inhibition of the growth of tumor at the primary site and its neighboring tissues, of cancer already treated by radiation, chemotherapy, surgical operation, or other techniques, and the absence of the growth of tumor at a new distal site. The desired or beneficial effects may be subjectively perceived by the patient or may be objectively found. In the case of, for example, a human patient, the human is able to recognize improvement in energy or vitality or reduction in pain as improvement or a therapy-responsive sign perceived by the patient. Alternatively, a clinician is able to notice decrease in tumor size or the amount of tumor tissues on the basis of findings gained by physical examination, experimental parameters, tumor markers, or X-ray photography. Some experimental signs that can be observed by the clinician in response to treatment include normalized test results of, for example, leukocyte counts, erythrocyte counts, platelet counts, erythrocyte sedimentation rates, and levels of various enzymes. The clinician is further able to observe decrease in detectable tumor marker level. Alternatively, other tests, such as sonography, nuclear magnetic resonance test, and positron emission test, may be used for evaluating objective improvement.

Any cancer highly expressing the targeted GPC3 corresponds to the cancer to be treated by the GPC3-targeting therapeutic agent of the present invention. One example of such cancer include cancer selected from breast cancer, uterine cervix cancer, colorectal cancer, uterine body cancer, head and neck cancer, liver cancer, lung cancer, malignant carcinoid, malignant glioma, malignant lymphoma, malignant melanoma, ovary cancer, pancreatic cancer, prostatic cancer, kidney cancer, skin cancer, stomach cancer, testicle cancer, thyroid cancer, urothelial cancer, and the like.

Method for Determining Efficacy of GPC3-Targeting Therapeutic Agent

In a non-limiting aspect, the present invention provides a method comprising measuring an expression level of GPC3 per tumor cell in a biological sample isolated from a patient before the start of administration of a GPC3-targeting therapeutic agent, and determining that the GPC3-targeting therapeutic agent is effective when the expression level is a predetermined value. The "patient before the start of administration of a GPC3-targeting therapeutic agent" refers to a patient diagnosed with cancer, having no history of administration of the GPC3-targeting therapeutic agent mentioned above. For this patient, it may be determined that the GPC3-targeting therapeutic agent is effective from the total expression level of GPC3 in tumor tissues or the expression level thereof per unit area as mentioned above, or it may be determined that the GPC3-targeting therapeutic agent is not effective from the total expression level of GPC3 in tumor tissues or the expression level thereof per unit area as mentioned above. In a certain aspect of the present invention, for example, a patient for whom the GPC3-targeting therapeutic agent is really effective can be extracted, by also taking the GPC3 expression level per tumor cell into consideration, from patients for whom it has been determined that the GPC3-targeting therapeutic agent is not effective. The administration route of the GPC3-targeting therapeutic agent can be appropriately selected from administration routes suitable for the properties, etc., of the GPC3-targeting therapeutic agent to be administered. Examples of the administration route include parenteral administration. Further examples of the parenteral administration include injection, transnasal administration, transpulmonary administration, and percutaneous administration. Further examples of the injection include systemic or local administration based on intravenous injection, intramuscular injection, intraperitoneal injection, and subcutaneous injection.

In a non-limiting aspect, the method of the present invention comprises measuring an expression level of GPC3, per tumor cell, expressed in the biological sample isolated from the patient, wherein it is predicted, expected, or determined that the GPC3-targeting therapeutic agent for cancer in the patient is effective when the expression level is a predetermined value.

In a non-limiting aspect of the present invention, the phrase "the expression level of GPC3 per tumor cell is a predetermined value" means that the expression level of GPC3 per tumor cell is high. The phrase "the expression level of GPC3 is high" means that the expression level of GPC3 per tumor cell is higher than a particular set value. The predetermined value can be set to a median value (50-percentile value), a 55-percentile value, a 60-percentile value, a 65-percentile value, a 70-percentile value, a 75-percentile value, or an 80-percentile value in a patient group, or a value higher than any of these values. The predetermined value may be any predetermined value at which the effects of the GPC3-targeting therapeutic agent can be expected, as long as the value falls within a range higher than the average expression level of GPC3 per tumor cell in biological samples of, for example, a patient group for which the effects of the GPC3-targeting therapeutic agent on cancer cannot be confirmed by the administration of the GPC3-targeting therapeutic agent to a plurality of cancer patients. Also, the predetermined value can be determined on the basis of the average expression level of GPC3 per tumor cell of, for example, a patient group for which a tendency to significantly extend PFS (progression free survival) or significantly extend OS (overall survival) is confirmed by the administration of the GPC3-targeting therapeutic agent to a plurality of cancer patients. For example, the expression levels of GPC3 per tumor cell of a plurality of cancer patients are measured, and a median value (50-percentile value), a 55-percentile value, a 60-percentile value, a 65-percentile value, a 70-percentile value, a 75-percentile value, or an 80-percentile value thereof, or a value higher than any of these values can be used as a predetermined value for selecting, with a high probability, a patient for which a tendency to significantly extend PFS or significantly extend OS with the GPC3-targeting therapeutic agent is confirmed. In this context, the plurality of cancer patients can be any number at which the predetermined value for the expression level of GPC3 per tumor cell serving as a criterion for determining the efficacy of the GPC3-targeting therapeutic agent can be calculated as a significant value, and is preferably 100 or more people, more preferably 150 or more people. Specifically, the predetermined value can be determined from, for example, values higher than a particular value such as 10000, 11000, 12000, 13000, 14000, 15000, 16000, 16100, 16200, 16300, 16400, 16500, 16600, 16700, 16800, 16900, 17000, 17100, 17200, 17300, 17400, 17500, 17600, 17700, 17800, 17900, 18000, 18100, 18200, 18300, 18400, 18500, 18600, 18700, 18800, 18900, 19000, 19100, 19200, 19300, 19400, 19500, 19600, 19700, 19800, 19900, 20000, 20100, 20200, 20300, 20400, 20500, 20600, 20700, 20800, 20900, 21000, 21100, 21200, 21300, 21400, 21500, 21600, 21700, 21800, 21900, 22000, 22100, 22200, 22300, 22400, 22500, 22600, 22700, 22800, 22900, or 23000 in terms of the IQD cell score mentioned above. The particular value can be appropriately selected from a numerical range of, for example, 11000 to 22000. Preferred examples of the numerical range include 13000 to 22000. More preferred examples of the numerical range include, but are not limited to, 15000 to 22000, further preferably 16000 to 22000, 17000 to 22000, 18000 to 22000, 19000 to 22000, 20000 to 22000, and 21000 to 22000. A value higher than the particular value selected from the numerical range can be used as the predetermined value.

In a non-limiting aspect of the present invention, patients that have any low immunohistochemical staining score (e.g., IHC total score of lower than 7 or composite score 2 of 2+ or lower, 1+ or lower, or 0) of GPC3 and are thereby usually judged as having no or low efficacy of the GPC3-targeting therapeutic agent can be used as subjects to evaluate that the GPC3-targeting therapeutic agent is effective for a patient having a predetermined value of a GPC3 expression level per tumor cell. In this context, the predetermined value is a value that is higher than the average of the patient group having any low immunohistochemical staining score and is, for example, 1 or more times, 1.05 or more times, 1.1 or more times, 1.15 or more times, 1.2 or more times, 1.25 or more times, 1.3 or more times, 1.35 or more times, 1.4 or more times, 1.45 or more times, 1.5 or more times, 1.55 or more times, 1.6 or more times, 1.65 or more times, 1.7 or more times, 1.75 or more times, 1.8 or more times, 1.85 or more times, 1.9 or more times, 1.95 or more times, 2 or more times, 2.1 or more times, 2.2 or more times, 2.3 or more times, 2.4 or more times, 2.5 or more times, 2.6 or more times, 2.7 or more times, 2.8 or more times, 2.9 or more times, 3 or more times, 3.1 or more times, 3.2 or more times, 3.3 or more times, 3.4 or more times, 3.5 or more times, 3.6 or more times, 3.7 or more times, 3.8 or more times, 3.9 or more times, 4 or more times, 4.1 or more times, 4.2 or more times, 4.3 or more times, 4.5 or more times, 4.6 or more times, 4.7 or more times, 4.8 or more times, 4.9 or more times, 5 or more times, 6 or more times, 7 or more times, 8 or more times, 9 or more times, 10 or more times, 11 or more times, 12 or more times, 13 or more times, 14 or more times, 15 or more times, 20 or more times, 30 or more times, 40 or more times, 50 or more times, 60 or more times, 70 or more times, 80 or more times, 90 or more times, 100 or more times, 200 or more times, 300 or more times, 400 or more times, 500 or more times, 600 or more times, 700 or more times, 800 or more times, 900 or more times, or 1000 or more times the average. In this aspect, the subjects can be patients untreated with the GPC3-targeting therapeutic agent.

In a non-limiting aspect, the method of the present invention comprises measuring a size of tumor cells in a tissue preparation of each patient in a group having a GPC3-IHC membrane H score, a GPC3-IHC cytoplasm H score, a GPC3-IQD intensity score, or an IQD cell score of a predetermined value (I), wherein it is predicted, expected, or determined that the GPC3-targeting therapeutic agent for cancer in the patient is effective when the size of tumor cells is a predetermined value (II). The predetermined values (I) and (II) can each individually be set to a median value (50-percentile value), a 55-percentile value, a 60-percentile value, a 65-percentile value, a 70-percentile value, a 75-percentile value, or an 80-percentile value in the patient group, or a value higher than any of these values. The predetermined value (II) can be determined on the basis of tumor cell sizes in biological samples of, for example, a patient group for which the effects of the GPC3-targeting therapeutic agent on cancer cannot be confirmed by the administration of the GPC3-targeting therapeutic agent to a plurality of cancer patients. Also, the predetermined value (II) can be determined on the basis of the tumor cell sizes of, for example, a patient group for which a tendency to significantly extend PFS (progression free survival) or significantly extend OS (overall survival) is confirmed by the administration of the GPC3-targeting therapeutic agent to a plurality of cancer patients. The predetermined value (II) can be determined on the basis of tumor cell sizes in tissue preparations of, for example, a plurality of cancer patients having a GPC3-IHC membrane H score, a GPC3-IHC cytoplasm H score, a GPC3-IQD intensity score, or an IQD cell score of a predetermined value (I). In any of these cases, a median value (50-percentile value), a 55-percentile value, a 60-percentile value, a 65-percentile value, a 70-percentile value, a 75-percentile value, or an 80-percentile value of the tumor cell sizes in the patient group or a value higher than any of these values can be used as the predetermined value (II) for expecting, predicting, or determining that the GPC3-targeting therapeutic agent for cancer in the patient is effective, and, preferably, can be used as the predetermined value (II) for selecting, with a high probability, a patient for which a tendency to significantly extend PFS or significantly extend OS with the GPC3-targeting therapeutic agent is confirmed.

The predetermined value of the expression level of GPC3 per tumor cell can slightly vary depending on many factors, for example, the assay method used, the type of a sample for the assay of GPC3 per tumor cell, storage conditions (e.g., temperature and duration) of the sample, and the ethnic identity of the patient. In the method for predicting, expecting, or determining the efficacy, the expression level of GPC3 per tumor cell is measured in a biological sample, particularly, a liver cancer tissue sample, isolated from the patient.

As described above, it is determined that the GPC3-targeting therapeutic agent is effective when the expression level of GPC3 per tumor cell is a predetermined value. In this procedure, whether the patient has, in the Fcγ receptor type IIA and/or type IIIA genes, a polymorphism that results in homozygous or heterozygous Val at amino acid residue 158 of FcγRIIIA and/or a polymorphism that results in homozygous or heterozygous His at amino acid residue 131 of FcγRIIA may be taken into consideration. Specifically, the method of the present invention also comprises determining that the GPC3-targeting therapeutic agent is effective when the expression level of GPC3 per tumor cell in the applicable patient is a predetermined value and the applicable patient has a polymorphism that results in homozygous or heterozygous Val at amino acid residue 158 of FcγRIIIA and/or a polymorphism that results in homozygous or heterozygous His at amino acid residue 131 of FcγRIIA.

In this context, the phrase "having a polymorphism that results in homozygous or heterozygous Val at amino acid residue 158 of FcγRIIIA" corresponds to the case where the patient has a nucleotide sequence of Val homozygote (V/V) or heterozygote (V/F) when a nucleotide sequence encoding amino acid residue 158 of FcγRIIIA is confirmed according to the method described in the aforementioned paragraph "Confirmation of Fcγ receptor gene polymorphism". Also, the phrase "having a polymorphism that results in homozygous or heterozygous His at amino acid residue 131 of FcγRIIA" corresponds to the case where the patient has a nucleotide sequence of His homozygote (H/H) or heterozygote (H/R) when a nucleotide sequence encoding amino acid residue 131 of FcγRIIA is confirmed in the same way as above.

Method for Determining Efficacy of GPC3-Targeting Therapeutic Agent in Consideration of Free GPC3 Concentration As described above, it is determined that the GPC3-targeting therapeutic agent is effective when the expression level of GPC3 per tumor cell is a predetermined value. In this procedure, a free GPC3 concentration may be further taken into consideration. Specifically, the method of the present invention also comprises measuring a free GPC3 concentration in a biological sample isolated from a patient before the start of administration of a GPC3-targeting therapeutic agent, and determining that the GPC3-targeting therapeutic agent is effective when the free GPC3 concentration is a predetermined value.

As described above, it is determined that the GPC3-targeting therapeutic agent is effective when the expression level of GPC3 per tumor cell is a predetermined value. After the start of administration, the continuation of the administration of the GPC3-targeting therapeutic agent may be determined by also taking a free GPC3 concentration into consideration. Specifically, the method of the present invention also comprises monitoring a free GPC3 concentration in a biological sample isolated from a patient before the start of administration of a GPC3-targeting therapeutic agent and/or a patient treated with the GPC3-targeting therapeutic agent, and determining the continuation of the administration of the GPC3-targeting therapeutic agent when the free GPC3 concentration is predetermined value.

In a non-limiting aspect, the predetermined value of the free GPC3 concentration can be determined from particular values such as 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1.0 ng/mL, 2.0 ng/mL, 3.0 ng/mL, 4.0 ng/mL, 5.0 ng/mL, 6.0 ng/mL, 7.0 ng/mL, 8.0 ng/mL, 9.0 ng/mL, 10.0 ng/mL, 15.0 ng/mL, 20.0 ng/mL, 25.0 ng/mL, 30.0 ng/mL, 35.0 ng/mL, 40.0 ng/mL, 45.0 ng/mL, 50.0 ng/mL, 55.0 ng/mL, 60.0 ng/mL, 65.0 ng/mL, 70.0 ng/mL, 75.0 ng/mL, 80.0 ng/mL, 85.0 ng/mL, 90.0 ng/mL, and 100.0 ng/mL, and can be determined as a numerical range containing particular values arbitrarily selected as the upper and lower limits from the group of particular values described above. Examples of the numerical range include, but are not limited to, 0.1 to 100 ng/mL, 0.5 to 80 ng/mL, 1.0 to 60 ng/mL, 2.0 to 55 ng/mL, 3.0 to 50 ng/mL, 4.0 to 45 ng/mL, 5.0 to 40 ng/mL, 6.0 to 35 ng/mL, 7.0 to 30 ng/mL, 8.0 to 25 ng/mL, 9.0 to 20 ng/mL, and 10 to 20 ng/mL. The predetermined value of the free GPC3 concentration can slightly vary depending on many factors, for example, the assay method used, the type of a biological sample for free GPC3 assay, storage conditions (e.g., temperature and duration) of the biological sample, and the ethnic identity of the patient. In the method for predicting, expecting, or the method for determining the efficacy or determining the continuation of the administration of the GPC3-targeting therapeutic agent, a concentration in a biological sample of blood, plasma, or serum isolated from the patient is measured as the concentration of free GPC3.

The free GPC3 concentration can be measured in a biological sample isolated after the start of administration of the GPC3-targeting therapeutic agent and may be measured in a plurality of biological samples collected at predetermined time intervals. When the free GPC3 concentration in any one of the plurality of biological samples collected at predetermined time intervals is the predetermined concentration mentioned above, it is predicted, expected, or determined that the GPC3-targeting therapeutic agent for cancer in the patient is effective or the continuation of the administration of the GPC3-targeting therapeutic agent is determined. The predetermined time intervals are appropriately set. In a non-limiting aspect of the intervals, the samples can be collected at intervals of 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months after the initial administration of the GPC3-targeting therapeutic agent, or at any point in time between the start and completion of administration of the GPC3-targeting therapeutic agent, for example, after 1, 2, 3, 4 or more treatment cycles. The dosing intervals, i.e., the treatment cycles, can be appropriately set. One non-limiting example thereof includes 1 day, 2 days, 3 days, 4 days, 5 days, 6 days, 7 days (i.e., 1 week), 8 days, 9 days, 10 days, 11 days, 12 days, 13 days, 14 days (i.e., 2 weeks), 15 days, 16 days, 17 days, 18 days, 19 days, 20 days, 21 days (i.e., 3 weeks), 22 days, 23 days, 24 days, 25 days, 26 days, 27 days, 28 days (i.e., 4 weeks), 29 days, 30 days, 1 month, 5 weeks, 6 weeks, 7 weeks, 8 weeks, 9 weeks, 10 weeks, 2 months, 3 months, 4 months, 5 months, or 6 months.

In a non-limiting aspect, the monitoring of the free GPC3 concentration in the biological sample isolated from the patient involves monitoring a free GPC3 concentration in blood, plasma, or serum isolated 30 days or 1 month after the start of administration of the GPC3-targeting therapeutic agent from the patient treated with the GPC3-targeting therapeutic agent. In a non-limiting aspect, examples of the case where the free GPC3 concentration is a predetermined value include the case where the monitored free GPC3 concentration ranges from 0.1 ng/mL to 100 ng/mL. In another non-limiting aspect, the monitoring of the free GPC3 concentration in the biological sample isolated from the patient involves monitoring a free GPC3 concentration in blood, plasma, or serum isolated 2 months, 3 months, 4 months, 5 months, or 6 months after the start of administration of the GPC3-targeting therapeutic agent from the patient treated with the GPC3-targeting therapeutic agent. In a non-limiting aspect, examples of the case where the free GPC3 concentration is a predetermined value include the case where the monitored free GPC3 concentration ranges from 0.1 ng/mL to 100 ng/mL.

In another non-limiting aspect, the free GPC3 concentration in a biological sample isolated from a patient treated with the GPC3-targeting therapeutic agent can be compared with a free GPC3 concentration ("baseline concentration") measured in a biological sample of blood, plasma, or serum isolated before the start of administration of the GPC3-targeting therapeutic agent from the patient. In this aspect, the "predetermined value" of the free GPC3 concentration means that the free GPC3 concentration in a biological sample isolated from a patient treated with the GPC3-targeting therapeutic agent is equal to or higher than the baseline concentration. Specifically, when the free GPC3 concentration after the start of administration of the GPC3-targeting therapeutic agent is equal to or larger than that before the start of administration of the GPC3-targeting therapeutic agent in one patient, it is predicted, expected, or determined that the GPC3-targeting therapeutic agent for cancer in the patient is effective or the continuation of the administration of the GPC3-targeting therapeutic agent is determined. The rate at which the free GPC3 concentration after the start of administration of the GPC3-targeting therapeutic agent is equal to or larger than that before the start of administration of the GPC3-targeting therapeutic agent can be appropriately selected by those skilled in the art and is not limited to a particular value. Such a rate can be appropriately selected from a numerical range of 1 time to $10^6$ times. In a non-limiting aspect, examples of the case where the free GPC3 concentration is a predetermined value include the case where the rate is, for example, 1 or more times, 1.05 or more times, 1.1 or more times, 1.2 or more times, 1.3 or more times, 1.4 or more times, 1.5 or more times, 1.6 or more times, 1.7 or more times, 1.8 or more times, 1.9 or more times, 2 or more times, 2.1 or more times, 2.2 or more times, 2.3 or more times, 2.4 or more times, 2.5 or more times, 2.6 or more times, 2.7 or more times, 2.8 or more times, 2.9 or more times, 3 or more times, 3.1 or more times, 3.2 or more times, 3.3 or more times, 3.4 or more times, 3.5 or more times, 3.6 or more times, 3.7 or more times, 3.8 or more times, 3.9 or more times, 4 or more times, 4.1 or more times, 4.2 or more times, 4.3 or more times, 4.4 or more times, 4.5 or more times, 4.6 or more times, 4.7 or more times, 4.8 or more times, 4.9 or more times, 5 or more times, 5.1 or more times, 5.2 or more times, 5.3 or more times, 5.4 or more times, 5.5 or more times, 5.6 or more times, 5.7 or more times, 5.8 or more times, 5.9 or more times, 6 or more times, 6.1 or more times, 6.2 or more times, 6.3 or more times, 6.4 or more times, 6.5 or more times, 6.6 or more times, 6.7 or more times, 6.8 or more times, 6.9 or more times, 7 or more times, 7.1 or more times, 7.2 or more times, 7.3 or more times, 7.4 or more times, 7.5 or more times, 7.6 or more times, 7.7 or more times, 7.8 or more times, 7.9 or more times, 8 or more times, 8.1 or more times, 8.2 or more times, 8.3 or more times, 8.4 or more times, 8.5 or more times, 8.6 or more times, 8.7 or more times, 8.8 or more times, 8.9 or more times, 9 or more times, 9.1 or more times, 9.2 or more times, 9.3 or more times, 9.4 or more times, 9.5 or more times, 9.6 or more times, 9.7 or more times, 9.8 or more times, 9.9 or more times, 10 or more times, 11 or more times, 12 or more times, 13 or more times, 14 or more times, 15 or more times, 16 or more times, 17 or more times, 18 or more times, 19 or more times, 20 or more times, 21 or more times, 22 or more times, 23 or more times, 24 or more times, 25 or more times, 26 or more times, 27 or more times, 28 or more times, 29 or more times, 30 or more times, 31 or more times, 32 or more times, 33 or more times, 34 or more times, 35 or more times, 36 or more times, 37 or more times, 38 or more times, 39 or more times, 40 or more times, 41 or more times, 42 or more times, 43 or more times, 44 or more times, 45 or more times, 46 or more times, 47 or more times, 48 or more times, 49 or more times, 50 or more times, 55 or more times, 60 or more times, 65 or more times, 70 or more times, 75 or more times, 80 or more times, 85 or more times, 90 or more times, 95 or more times, 100 or more times, 105 or more times, 110 or more times, 120 or more times, 130 or more times, 140 or more times, 150 or more times, 160 or more times, 170 or more times, 180 or more times, 190 or more times, 200 or more times, 220 or more times, 240 or more times, 260 or more times, 280 or more times, 300 or more times, 320 or more times, 340 or more times, 360 or more times, 380 or more times, 400 or more times, 420 or more times, 440 or more times, 460 or more times, 480 or more times, 500 or more times, 550 or more times, 600 or more times, 650 or more times, 700 or more times, 750 or more times, 800 or more times, 850 or more times, 900 or more times, 950 or more times, 1000 or more times, 2000 or more times, 3000 or more times, 4000 or more times, 5000 or more times, 6000 or more times, 7000 or more times, 8000 or more times, 9000 or more times, $10^4$ or more times, $2 \times 10^4$ or more times, $4 \times 10^4$ or more times, $6 \times 10^4$ or more times, $8 \times 10^4$ or more times, $10^5$ or more times, $2 \times 10^5$ or more times, $4 \times 10^5$ or more times, $6 \times 10^5$ or more times, $8 \times 10^5$ or more times, or $10^6$ or more times.

In a non-limiting aspect, the monitoring of the free GPC3 concentration in the biological sample isolated from the patient involves monitoring a free GPC3 concentration in blood, plasma, or serum isolated 30 days or 1 month after the start of administration of the GPC3-targeting therapeutic agent from the patient treated with the GPC3-targeting therapeutic agent. In a non-limiting aspect, examples of the case where the free GPC3 concentration is a predetermined value include the case where the monitored free GPC3 concentration is equal to or larger than the baseline concentration. In another non-limiting aspect, the monitoring of the free GPC3 concentration in the biological sample isolated from the patient involves monitoring a free GPC3 concentration in blood, plasma, or serum isolated 2 months, 3 months, 4 months, 5 months, or 6 months after the start of administration of the GPC3-targeting therapeutic agent from the patient treated with the GPC3-targeting therapeutic agent. In a non-limiting aspect, examples of the case where the free GPC3 concentration is a predetermined value include the case where the monitored free GPC3 concentration is 1 or more times to $10^6$ or more times the baseline concentration.

Method for Selecting Patient

The method for selecting a patient according to the present invention comprises the step of determining that the GPC3-targeting therapeutic agent is effective for a patient when the expression level of GPC3 per tumor cell in a biological sample isolated from the patient is a predetermined value in the method mentioned above. In a non-limiting aspect, the method for selecting a patient according to the present invention may further comprise the step of determining that the GPC3-targeting therapeutic agent is effective for a patient when a free GPC3 concentration in a biological sample isolated from the patient is a predetermined value. In an alternative non-limiting aspect, the method for selecting a patient may further comprise the step of monitoring a free GPC3 concentration in a biological sample isolated from a patient before the start of administration of a GPC3-targeting therapeutic agent and/or a patient treated with the GPC3-targeting therapeutic agent, and determining the continuation of the administration of the GPC3-targeting therapeutic agent when the free GPC3 concentration is a predetermined value.

Therapeutic Agent

In the present invention, the therapeutic agent usually refers to a drug for the treatment or prevention of a disease or for examination or diagnosis. In the present invention, the phrase "GPC3-targeting therapeutic agent which is to be administered to (only) a cancer patient having a predetermined value of an expression level of GPC3 per tumor cell in a biological sample isolated from the cancer patient before the start of administration of the GPC3-targeting therapeutic agent" may be translated into a "method for treating cancer, comprising administering a GPC3-targeting therapeutic agent to (only) a cancer patient having a predetermined value of an expression level of GPC3 per tumor cell in a biological sample isolated from the cancer patient before the start of administration of the GPC3-targeting therapeutic agent", or may be translated into "use of a GPC3-targeting therapeutic agent which is to be administered to (only) a cancer patient having a predetermined value of an expression level of GPC3 per tumor cell in a biological sample isolated from the cancer patient before the start of administration of the GPC3-targeting therapeutic agent, for production of a medicament for the treatment of cancer". In this context, the phrase "only a patient" means that the GPC3-targeting therapeutic agent is administered to a patient having a predetermined value of an expression level of GPC3 per tumor cell in the biological sample, but is not administered to a patient having no such predetermined value. In a certain preferred aspect of the present invention, for example, the GPC3-targeting therapeutic agent can be administered to a cancer patient having a predetermined value of a GPC3 expression level per tumor cell in a biological sample isolated from the cancer patient before the start of administration of the GPC3-targeting therapeutic agent, but cannot be administered to a patient having no such predetermined value (e.g., the GPC3-targeting therapeutic agent is administered when the GPC3 expression level per tumor cell in the biological sample is equal to or higher than a given value, but is not administered when the GPC3 expression level per tumor cell in the biological sample is lower than the given value).

The therapeutic agent of the present invention can be formulated by use of a method known to those skilled in the art. For example, the therapeutic agent of the present invention can be parenterally used in the form of an injection in a sterile solution or suspension with water or any other pharmaceutically acceptable solution. For example, the active ingredient can be appropriately combined with pharmacologically acceptable carriers or media, specifically, sterile water or saline, a plant oil, an emulsifier, a suspending agent, a surfactant, a stabilizer, a flavor, an excipient, a vehicle, an antiseptic, a binder, and the like and mixed therewith in a unit dosage form required for generally accepted pharmaceutical practice to produce preparations. The amount of the active ingredient in these preparations is set to give an appropriate volume within a prescribed range.

Sterile compositions for injection can be formulated according to usual pharmaceutical practice using a vehicle such as injectable distilled water. Examples of injectable aqueous solutions include saline and isotonic solutions containing glucose or other adjuvants (e.g., D-sorbitol, D-mannose, D-mannitol, and sodium chloride). An appropriate solubilizer, for example, an alcohol (ethanol, etc.), a polyalcohol (propylene glycol, polyethylene glycol, etc.), or a nonionic surfactant (Polysorbate 80™, HCO-50, etc.) may be used in combination therewith.

Examples of oil solutions include sesame oil and soybean oil. Benzyl benzoate and/or benzyl alcohol may be used as a solubilizer in combination therewith. These injectable solutions may be mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The prepared injections are usually charged into appropriate ampules.

The therapeutic agent of the present invention is preferably administered by parenteral administration. For example, the therapeutic agent is administered in a dosage form of an injection, a transnasal agent, a transpulmonary agent, or a percutaneous agent. The therapeutic agent can be administered systemically or locally by, for example, intravenous injection, intramuscular injection, intraperitoneal injection, or subcutaneous injection.

The administration method can be appropriately selected according to the age and symptoms of the patient. The single dose of a pharmaceutical preparation containing the therapeutic agent can be set within the range of, for example, 0.0001 mg to 1000 mg per kg body weight. Alternatively, the dose can be set to, for example, 0.001 to 100000 mg per patient, though the dose of the present invention is not necessarily limited to these numerical values. The dose and the administration method vary depending on the body weight, age, symptoms, etc. of the patient. Those skilled in the art can set an appropriate dose and administration method in consideration of these conditions. As a preferred example of the dose and the administration method of the present invention, the therapeutic agent can be administered to achieve a blood trough level equal to or higher than a given level in the patient. Preferred examples of the blood trough level can include 150 µg/mL or higher, 160 µg/mL or higher, 170 µg/mL or higher, 180 µg/mL or higher, 190 µg/mL or higher, 200 µg/mL or higher, 210 µg/mL or higher, 220 µg/mL or higher, 230 µg/mL or higher, 240 µg/mL or higher, 250 µg/mL or higher, 260 µg/mL or higher, 270 µg/mL or higher, 280 µg/mL or higher, 290 µg/mL or higher, 300 µg/mL or higher, and 400 µg/mL or higher. More preferred examples thereof can include 200 µg/mL or higher.

Instruction

The preparation of the present invention comprises an instruction stating that a GPC3-targeting therapeutic agent is administered to (only) a cancer patient having a predetermined value of an expression level of GPC3 per tumor cell in a biological sample isolated from the cancer patient before the start of administration of the GPC3-targeting therapeutic agent. The kit for the treatment of liver cancer according to the present invention comprises a GPC3-targeting therapeutic agent and an instruction stating that the GPC3-targeting therapeutic agent is administered to (only) a cancer patient having a predetermined value of an expression level of GPC3 per tumor cell in a biological sample isolated from the cancer patient before the start of administration of the GPC3-targeting therapeutic agent. In this context, the phrase "only a patient" means that the GPC3-targeting therapeutic agent is administered to a patient having a predetermined value of an expression level of GPC3 per tumor cell in the biological sample, but is not administered to a patient having no such predetermined value. In a certain preferred aspect of the present invention, the instruction can be, for example, an instruction stating the effect that the GPC3-targeting therapeutic agent is administered to a cancer patient having a predetermined value of a GPC3 expression level per tumor cell in a biological sample isolated from the cancer patient before the start of administration of the GPC3-targeting therapeutic agent, but is not administered to a patient having no such predetermined value (e.g., the instruction may state the effect that the GPC3-targeting therapeutic agent is administered when the GPC3 expression level per tumor cell is equal to or higher than a given value, but is not administered when the GPC3 expression level per tumor cell is lower than the given value).

In a non-limiting aspect, the present invention provides a preparation or a kit for the treatment of liver cancer, comprising an instruction stating that the preparation or the kit involves measuring an expression level of GPC3 per tumor cell in a biological sample isolated from a patient before the start of administration of a GPC3-targeting therapeutic agent, wherein it is determined that the GPC3-targeting therapeutic agent is effective when the expression level of GPC3 per tumor cell is a predetermined value.

In a non-limiting aspect, the present invention provides a preparation or a kit for the treatment of liver cancer, comprising an instruction stating that the preparation or the kit involves measuring an expression level of GPC3 per tumor cell in a biological sample isolated from the patient, wherein it is predicted, expected, or determined that the GPC3-targeting therapeutic agent for cancer in the patient is effective when the expression level is a predetermined value. In this context, examples of the predetermined value described in the instruction include the predetermined value described in the aforementioned paragraph "Method for determining efficacy of GPC3-targeting therapeutic agent".

The predetermined value of the expression level of GPC3 per tumor cell can slightly vary depending on many factors, for example, the assay method used, the type of a sample for the measurement of the GPC3 expression level per tumor cell, storage conditions (e.g., temperature and duration) of the sample, and the ethnic identity of the patient. In the method for predicting, expecting, or determining the efficacy, a value in a biological sample, particularly, a liver cancer tissue sample, isolated from the patient is measured as the predetermined value of the expression level of GPC3 per tumor cell.

The instruction as described above stating that the GPC3-targeting therapeutic agent is effective when the expression level of GPC3 per tumor cell is a predetermined value may state that even whether the patient has, in the Fcγ receptor type IIA and/or type IIIA genes, a polymorphism that results in homozygous or heterozygous Val at amino acid residue 158 of FcγRIIIA and/or a polymorphism that results in homozygous or heterozygous His at amino acid residue 131 of FcγRIIA is also taken into consideration. Specifically, the instruction may also state that it is determined that the GPC3-targeting therapeutic agent is effective when the expression level of GPC3 per tumor cell in the applicable patient is a predetermined value and the applicable patient has a polymorphism that results in homozygous or heterozygous Val at amino acid residue 158 of FcγRIIIA and/or a polymorphism that results in homozygous or heterozygous His at amino acid residue 131 of FcγRIIA.

In this context, the phrase "having a polymorphism that results in homozygous or heterozygous Val at amino acid residue 158 of FcγRIIIA" corresponds to the case where the patient has a nucleotide sequence of Val homozygote (V/V) or heterozygote (V/F) when a nucleotide sequence encoding amino acid residue 158 of FcγRIIIA is confirmed according to the method described in the aforementioned paragraph "Confirmation of Fcγ receptor gene polymorphism". Also, the phrase "having a polymorphism that results in homozygous or heterozygous His at amino acid residue 131 of FcγRIIA" corresponds to the case where the patient has a nucleotide sequence of His homozygote (H/H) or heterozygote (H/R) when a nucleotide sequence encoding amino acid residue 131 of FcγRIIA is confirmed in the same way as above.

The instruction as described above stating that it is determined that the GPC3-targeting therapeutic agent is effective when the expression level of GPC3 per tumor cell is a predetermined value may further state that a free GPC3 concentration in a biological sample isolated from the patient is also taken into consideration. Specifically, the instruction may also state that a free GPC3 concentration in a biological sample isolated from the applicable patient is measured, and it is determined that the GPC3-targeting therapeutic agent is effective when the free GPC3 concentration is a predetermined value.

The instruction as described above stating that it is determined that the GPC3-targeting therapeutic agent is effective when the expression level of GPC3 per tumor cell is a predetermined value may further state that the continuation of the administration of the GPC3-targeting therapeutic agent is determined by also taking a free GPC3 concentration into consideration. Specifically, the instruction may also state that a free GPC3 concentration in a biological sample isolated from a patient before the start of administration of a GPC3-targeting therapeutic agent and/or a patient treated with the GPC3-targeting therapeutic agent is monitored, and the continuation of the administration of the GPC3-targeting therapeutic agent is determined when the free GPC3 concentration is a predetermined value. In this context, examples of the predetermined value described in the instruction include the predetermined value described in the aforementioned paragraph "Method for determining efficacy of GPC3-targeting therapeutic agent in consideration of free GPC3 concentration".

Diagnostic Kit

The diagnostic kit of the present invention comprises a reagent for measuring an expression level of GPC3 per tumor cell in a biological sample isolated from a cancer patient before the start of administration of a GPC3-targeting therapeutic agent.

In a non-limiting aspect, the present invention provides a diagnostic kit comprising a reagent for measuring an expression level of GPC3 per tumor cell in a biological sample isolated from a cancer patient before the start of administration of a GPC3-targeting therapeutic agent, and an instruction stating that it is determined that the GPC3-targeting therapeutic agent is effective when the expression level of GPC3 per tumor cell measured using the reagent is a predetermined value. In a non-limiting aspect, the diagnostic kit of the present invention may further comprise a GPC3-targeting therapeutic agent which is to be administered to only a patient for whom it has been determined that the GPC3-targeting therapeutic agent is effective on the ground that the expression level of GPC3 per tumor cell measured using the reagent is a predetermined value.

EXAMPLES

Example 1

GC33 is a recombinant humanized IgG1 monoclonal antibody binding to human GPC3 with high affinity (WO2006/006693). Effects brought about by combined use of GC33 with a kinase inhibitor sorafenib have been found in a non-clinical study using a human liver cancer cell line (Ishiguro T et al., Anti-Glypican 3 antibody as a potential antitumor agent for human liver cancer. Cancer Res. (2008) 68, 9832-9838; and WO2009/122667).

According to the method of Ishiguro et al., the antitumor effect of GC33, ag-GC33 (a modified form of GC33 lacking ADCC activity by the substitution of asparagine at residue 297 serving as a N-linked glycosylation site in a heavy chain Fc region by an alanine residue for aglycosylation; Ishiguro T et al., Anti-Glypican 3 antibody as a potential antitumor agent for human liver cancer. Cancer Res. (2008) 68, 9832-9838), or sorafenib alone or combined use of GC33 or ag-GC33 with sorafenib as well as change in the level of a soluble form of GPC3 in mouse plasma was studied in mouse graft models using a human cell line HepG2 strongly expressing GPC3.

GC33 or ag-GC33 was administered at 5 mg/kg to the tail vein of each mouse once a week a total of three times from 18 days after HepG2 transplantation. Sorafenib was orally administered at 5 mg/kg to each mouse five times a week for 3 weeks from 18 days after HepG2 transplantation. Change in tumor volume in each administration group is shown in FIG. 1.

In the GC33 administration group, an antitumor effect was exerted so that tumor enlargement was inhibited as compared with the control group. On the other hand, no tumor enlargement inhibitory effect was seen in ag-GC33 lacking ADCC activity. In the sorafenib administration group, the tumor enlargement inhibitory effect was weaker than that of GC33. In the GC33/sorafenib combined use group, the tumor enlargement inhibitory effect was highest.

At the completion of the antitumor effect evaluation, plasma was collected from each mouse. Fragments of a soluble form of GPC3 were assayed by two types of ELISA methods differing in the combination of anti-GPC3 antibodies. In order to detect the fragments of a soluble form of GPC3 in ELISA, mouse monoclonal antibodies binding to the N-terminal subunit of human GPC3 were prepared as described in WO2004/022739. Hereinafter, the obtained antibodies are referred to as GT30 and GT607 for the sake of convenience. Also, mouse monoclonal antibodies binding to the C-terminal subunit of human GPC3 were prepared as described in WO2004/022739. Hereinafter, the obtained antibodies are referred to as GT96 and M3C11 for the sake of convenience. The combination of anti-GPC3 antibodies used was a combination of GT30 and GT607 or a combination of GT96 and M3C11. The fragments of a soluble form of GPC3 were assayed. The fragment of soluble GPC3 assayed with the former combination was defined as "sGPC3-N", and the fragment of soluble GPC3 assayed with the latter combination was defined as "sGPC3-C". sGPC3-N is GPC3 that is not anchored to GPC3-expressing cells, and is detected as a polypeptide comprising a polypeptide from the amino terminus to position 358 in GPC3 consisting of the polypeptide defined by SEQ ID NO: 1, or a polypeptide comprising a polypeptide known as a polypeptide from the amino terminus to position 374 in GPC3 consisting of the polypeptide defined by SEQ ID NO: 1. sGPC3-C is GPC3 that is not anchored to GPC3-expressing cells, and can be detected as a polypeptide comprising a polypeptide from the carboxy terminus to position 359 in GPC3 consisting of the polypeptide defined by SEQ ID NO: 1, or a polypeptide comprising a polypeptide known as a polypeptide from the carboxy terminus to position 375 in GPC3 consisting of the polypeptide defined by SEQ ID NO: 1.

Specifically, the detection of sGPC3-N and the detection of sGPC3-C by ELISA were performed as follows: first, the GT30 antibody diluted to 1 µg/mL with a carbonatebicarbonate buffer (manufactured by Sigma-Aldrich Co., LLC) or the M3C11 antibody adjusted to 128 µg/mL in the same way thereas was added at 50 µL/well to a 96-well microplate (manufactured by Meso Scale Discovery (MSD), Multi-array 96-well plate) and stirred at room temperature for 1 hour. Subsequently, the microplate was washed five times with a washing solution (manufactured by Sigma-Aldrich Co., LLC, PBS Buffered Saline with TWEEN® 20, pH 7.4). Then, a blocking solution (PBS Buffered Saline with TWEEN® 20 (pH 7.4) containing 2.5 or 5.0% Bovine Serum Albumin Fraction V manufactured by F. Hoffmann-La Roche, Ltd.) was added thereto at 100 µL/well and stirred at room temperature for 1 hour. The microplate was further washed three times with a washing solution. Then, a standard for calibration curve was serially diluted with a diluent (PBS Buffered Saline with TWEEN® 20 (pH 7.4) containing 0.05 or 1.0% Bovine Serum Albumin Fraction V) and then further mixed with an equivalent dose of control mouse plasma diluted five-fold with a diluent. The resulting standard solution for calibration curve or mouse plasma diluted 10-fold with a diluent was added thereto at 50 µL/well and stirred at room temperature for 1 hour. After washing five times with a washing solution, an antibody solution for detection containing a biotin-labeled GT607 antibody (1 µg/mL) or a biotin-labeled GT96 antibody (8 µg/mL) was added thereto at 50 µL/well and stirred at room temperature for 1 hour. After washing five times with a washing solution, SULFO-TAG Streptavidin (manufactured by Meso Scale Discovery (MSD)) diluted 500-fold with a diluent was added thereto at 25 µL/well and stirred at room temperature for 1 hour. After washing five times with a washing solution, a substrate solution (manufactured by Meso Scale Discovery (MSD), MSD Read Buffer T (4×) with Surfactant) was added thereto at 100 µL/well. Signals were measured using an electrochemiluminescence immunoassay apparatus (ECL; manufactured by Meso Scale Discovery (MSD), SECTOR imager 2400). On the basis of the measurement results, the concentration of sGPC3-N or sGPC3-C in the mouse plasma was calculated from the calibration curve. The standard for calibration curve used was recombinant GPC3 having alanine residues replaced for serine at residues 495 and 509 so as not to bind to heparan sulfate sugar chains (Hippo et al., Cancer Res. (2004) 64, 2418-2423).

Figure 2:
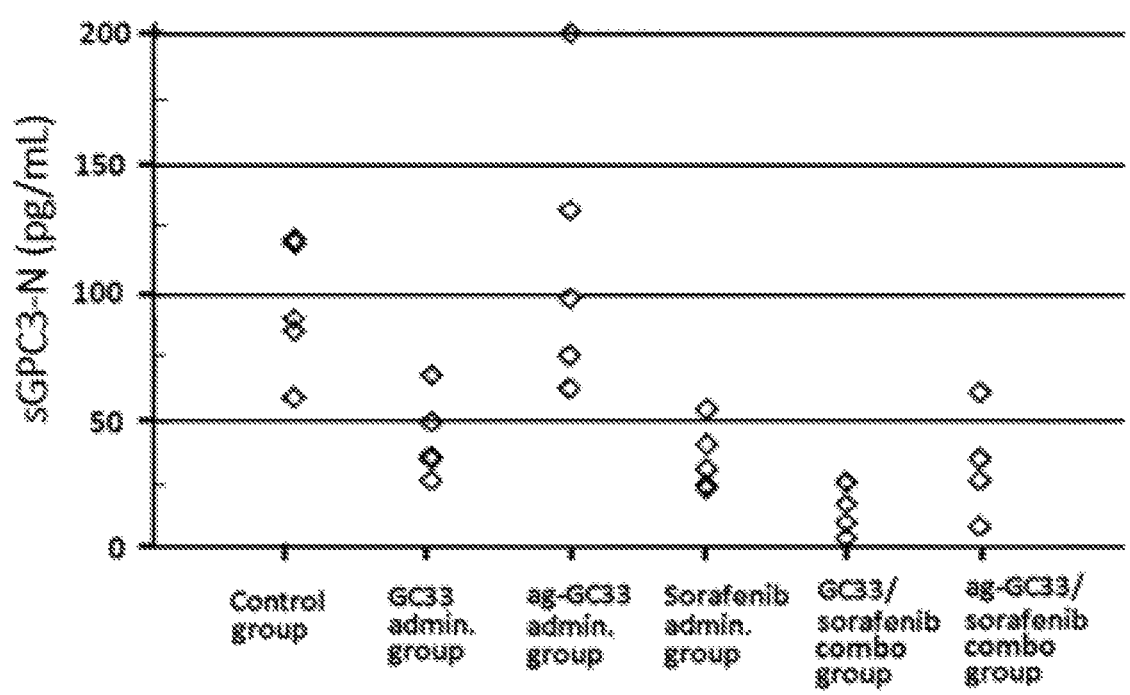
FIG. 2 shows the abundance of sGPC3-N, a fragment of a soluble form of GPC3, in the plasma of each administration group at the completion of antitumor effect evaluation.
Figure 3:
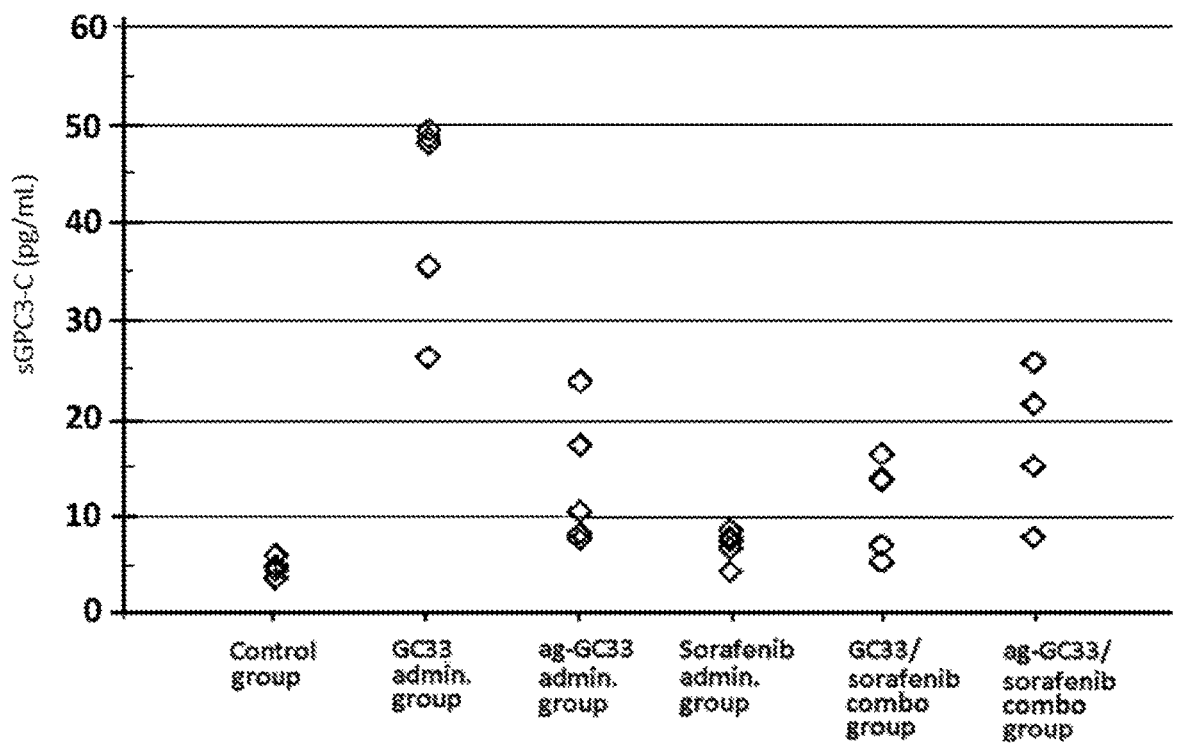
FIG. 3 shows the abundance of sGPC3-C, a fragment of a soluble form of GPC3, in the plasma of each administration group at the completion of antitumor effect evaluation.

A plot of the results of assaying sGPC3-N in each mouse is shown in FIG. 2, and a plot of the results of assaying sGPC3-C is shown in FIG. 3.

In the GC33 administration group, a lower level of sGPC3-N was found as compared with the control group. On the other hand, the sGPC3-N level in the group given ag-GC33 lacking ADCC activity was equivalent to that in the control group. The sGPC3-N level in the sorafenib administration group was equivalent to the GC33 administration group.

Unlike sGPC3-N, the sGPC3-C level was higher in the GC33 administration group compared with the control group, the ag-GC33 group, and the sorafenib group, suggesting that the antitumor effect based on the ADCC activity of GC33 brings about a rise in sGPC-3 level.

Example 2

In order to confirm the dose limiting toxicity (DLT) of combined use of GC33 and sorafenib in patients with advanced and/or recurrent hepatocellular carcinoma (HCC), a phase I multicenter clinical trial was carried out (GC-002US study). In this study aimed at confirming safety and/or tolerability in the patients with advanced and/or recurrent HCC, the pharmacokinetic profiles of GC33, and its antitumor effects, and exploring for biomarkers, GC33 was administered by injection through an intravenous infusion to each HCC patient once a week (2.5 mg/kg body weight, 5 mg/kg body weight, 10 mg/kg body weight, or 1,600 mg) or once per two weeks (1,600 mg). The administration of sorafenib was started from the day following the initial administration of GC33, and a dose of 400 mg was administered to each patient twice a day every day and decreased or withdrawn according to the package insert.

The HCC patients subjected to the administration had no history of treatment with sorafenib and had histologically or cytologically confirmed advanced or metastatic HCC unsuitable for surgical resection and/or curative treatment. Eligible patients were at least 18-year-old persons who had a chance to survive for 3 months or longer and exhibited Eastern Cooperative Oncology Group Performance Status of 0 or 1 and Child-Pugh class A or B (which was changed to Child-Pugh class A alone during the course of the study). The patients also had at least one lesion that was evaluable according to the response evaluation criteria in solid tumors (RECIST). In addition to the capability of providing HCC tumor tissues (needle biopsy preparations) for use in GPC3 immunohistochemical staining (GPC3-IHC), appropriate hematopoietic functions (absolute neutrophil count≥1500/µl, platelet≥75,000/µl (which was changed to 100,000/µL during the course of the test)), appropriate hepatic functions (total bilirubin≤3 times the normal level (which was changed to ≤1.5 times the normal level during the course of the test), aspartate aminotransferase and alanine aminotransferase≤5 times the normal level, PT-INR≤2.0), and appropriate renal functions (serum creatinine≤twice the normal level) were established as other criteria. The registered subjects excluded patients having difficulty in taking oral medication, pregnant, nursing, or pregnancy test-positive (women who underwent menstruation within 12 months from the registration date were subjected to the pregnancy test) patients, patients who did not plan to use appropriate fertility control, HIV antibody-positive patients, patients having active infection requiring treatment except for HBV or HCV, patients having other active malignant tumors with a disease-free interval shorter than 5 years, patients having a past history of transplantation, patients having an uncontrollable comorbidity, patients confirmed to have brain metastasis with symptoms, patients having central nervous system disorder or other mental disorders that interfered with consent or understanding of the protocol, patients having uncontrollable hypertension, patients having a past history of cancer-unrelated thromboembolism, severe pulmonary hemorrhage or any other life-threatening hemorrhage within 4 weeks before GPC3-targeting therapeutic agent administration, patients who still suffered the influence of severe unhealed wound or ulcer, bone fracture, or needle biopsy, patients who received an anticoagulant, a thrombolytic agent, a systemic antivirus drug, or blood transfusion within 2 weeks before GPC3-targeting therapeutic agent administration, patients who manifested known hypersensitivity to other antibody drugs or medicaments produced with CHO cells, and patients under treatment with a drug inducing CYP3A4. Alternatively, patients who received treatment including major surgical operation, radiation therapy, and other chemotherapies within 4 weeks before GPC3-targeting therapeutic agent administration were excluded from the subjects registered about the GPC3-targeting therapeutic agent, but were subjected to the GPC3-targeting treatment after a predetermined wash-out period. The protocol was carried out according to the guideline of the Good Clinical Practice (GCP) and approved by each participating ethical committee on clinical trials. All patients signed their names on written informed consent before registration. The administration of GC33 to the patients was performed by each cycle involving four doses for the once-weekly administration or each cycle involving two doses for the once-per-two week administration, and the administration of GC33 and sorafenib was continued unless the disease progressed or unacceptable toxicity appeared. Tumor was evaluated on the basis of a baseline and repetitively evaluated every two cycles until the disease progressed. The state of the disease was evaluated by principal investigators.

Safety and tolerability were evaluated as primary objectives, and PK analysis, effect evaluation, biomarker search, and optimum dose study intended for phase II clinical trials were conducted as secondary objectives. In the effect evaluation, change in the level of α fetoprotein (AFP), a known hepatocellular carcinoma marker, from a baseline, progression free survival (PFS), and time-to-progression (TTP) were determined.

Example 3

Figure 4:
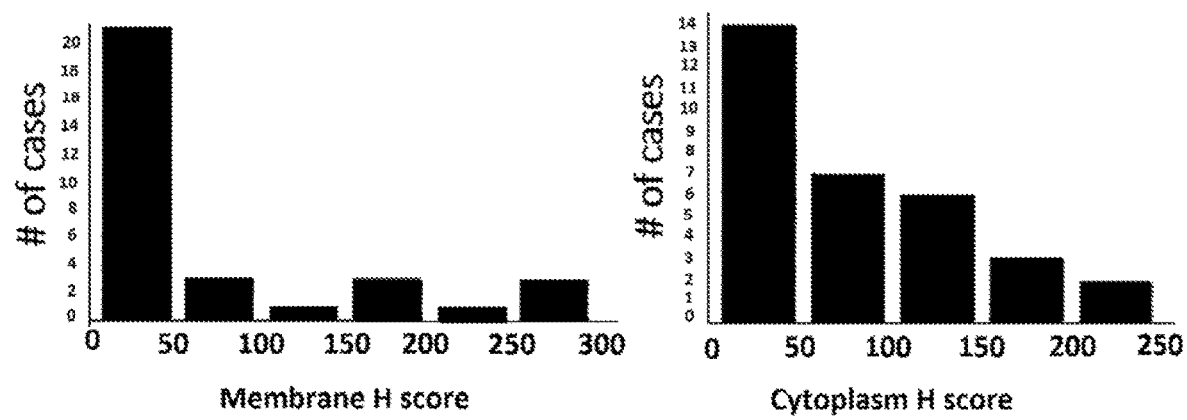
FIG. 4 shows a histogram of cell membrane or intracellular staining intensity (H score) in progressive and/or recurrent hepatocellular carcinoma (HCC) tissues that were harvested before the start of administration of GC33 and sorafenib, followed by the immunohistochemical staining of GPC3.

The expression of the GPC3 protein in HCC tumor tissues was evaluated by GPC3 immunohistochemical staining (GPC3-IHC). Before the start of administration of GC33 and sorafenib to HCC patients, HCC tumor tissues were obtained from the HCC patients by needle biopsy in each hospital, and formalin-fixed and paraffin-embedded to prepare tumor blocks. Unstained slides of HCC tumor tissues prepared from the tumor blocks were subjected to GPC3-IHC using BenchMark automatic staining apparatus (manufactured by Ventana Medical Systems, Inc.), and central measurement was conducted according to the instruction attached to anti-glypican 3 Mouse GC33 Monoclonal Primary Antibody (Ventana Medical Systems, Inc.). The staining intensity of cell membrane or cytoplasm of the tumor cells thus stained by GPC3-IHC (Ventana Medical Systems, Inc.) was classified into scores of 0 to 3. H scores (literature: K S. McCarty Jr. et al., Use of a monoclonal anti-Estrogen receptor antibody in the immunohistochemical evaluation of human tumors. Cancer Res. Suppl. (1986) 46, 4244s-4248s) to be calculated on the basis of the proportion of cells that exhibited each staining intensity were calculated according to the following calculation expression to obtain the distribution shown in FIG. 4.

$H$ Score=1×(Proportion (%) of Cells Having Weakly Positive Staining Intensity)+2×(Proportion (%) of Cells Having Moderately Positive Staining Intensity)+3×(Proportion (%) of Cells Having Strongly Positive Staining Intensity)

Some of the tumor samples thus evaluated were used in the additional evaluation of GPC3 expression by the immunofluorescent quantification digital slide technology (IQD) (GPC3-IQD). GPC3-IQD was carried out using a mouse GC33 antibody according to the method of Hashiguchi et al. (Hashiguchi A. et al., Using immunofluorescent digital slide technology to quantify protein expression in archival paraffin-embedded tissue sections. Pathol. Int. (2010) 60, 720-725).

Figure 5:
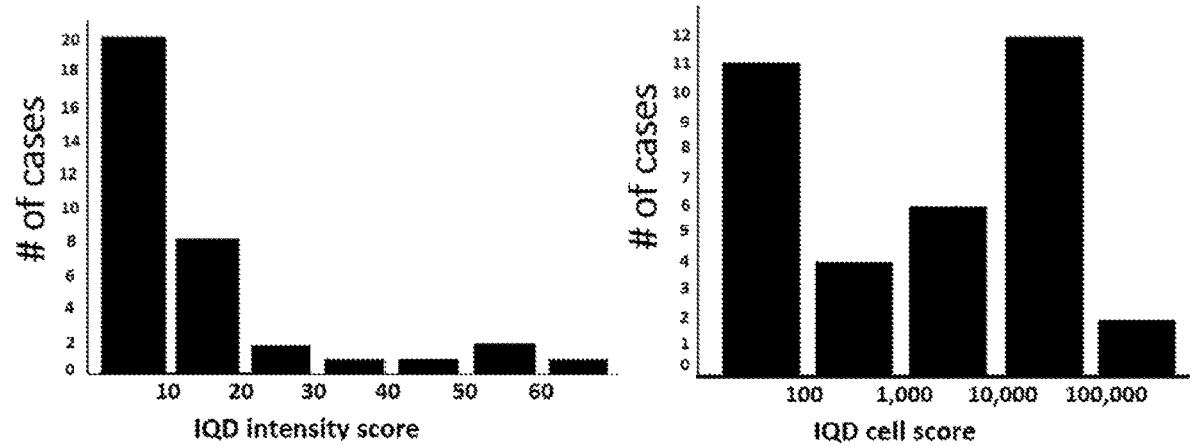
FIG. 5 shows fluorescence intensity per unit area (IQD intensity score) and fluorescence intensity per tumor cell (IQD cell score) in HCC tumor tissues that were obtained before the start of administration of GC33 and sorafenib, followed by immunofluorescent staining.

For IQD scores, an intensity score (IQD intensity score of GPC3) as total fluorescence intensity at a tumor site from which the fluorescence intensity of a non-cancer portion was subtracted, or a cell score (IQD cell score of GPC3) exhibiting fluorescence intensity per tumor cell was calculated as the average of samples to obtain the distribution shown in FIG. 5.

Table 4 shows respective GC33 doses and the number of cases evaluated by GPC3-IHC or GPC3-IQD.

TABLE 4

Table 4: Relationship between GC33 dose and the number of cases evaluated by GPC3-IHC or GPC3-IQD

| Cohort | GC33 dose | | | | |
| --- | --- | --- | --- | --- | --- |
| | 2.5 mg/kg/ week | 5 mg/kg/ week | 10 mg/kg/ week | 1,600 mg/ 2 weeks | 1,600 mg/ week |
| Administration case (Total number of cases = 40) | 12 cases | 12 cases | 3 cases | 6 cases | 7 cases |
| GPC3-IHC evaluation case (Total number of cases = 34) | 9 cases | 11 cases | 2 cases | 5 cases | 7 cases |

TABLE 4-continued

Table 4: Relationship between GC33 dose and the
number of cases evaluated by GPC3-IHC or GPC3-IQD

| Cohort | GC33 dose | | | | |
|---|---|---|---|---|---|
| | 2.5 mg/kg/ week | 5 mg/kg/ week | 10 mg/kg/ week | 1,600 mg/ 2 weeks | 1,600 mg/ week |
| GPC3-IQD evaluation case (Total number of cases = 34) | 10 cases | 10 cases | 3 cases | 5 cases | 6 cases |

Example 4

The concentration of free GPC3 in the serum of each patient treated with GC33 was measured. In the same way as in Example 1, the concentration of sGPC3-N was measured using the combination of GT30 and GT607, and the concentration of sGPC3-C was measured using the combination of GT96 and M3C11. The combination of GT30 and GT607 abided by the method of Haruyama et al. (Haruyama Y et al., High preoperative levels of serum glypican-3 containing N-terminal subunit are associated with poor prognosis in patients with hepatocellular carcinoma after partial hepatectomy. (2015) in press) to measure the concentration of free GPC3. The combination of GT96 and M3C11 also abided by the method of Haruyama et al. to measure the concentration of free GPC3 except that M3C11 bound with antibody-bound magnetic particles and GT96 bound with alkaline phosphatase were used.

Measurement values in the serum of the patients before the start of administration of GC33 and sorafenib were used as baseline values. Change from the baselines in measurement values in serum collected after the start of administration was calculated to determine the best rates of change, i.e., the minimum rate of change in sGPC3-N level and the maximum rate of change in sGPC3-C level.

Example 5

The relationship between an antitumor effect brought about by the administration of GC33 and sorafenib and GPC3 expression in tumor tissues was examined using each of the minimum rate of change in sGPC3-N level, the maximum rate of change in sGPC3-C level, the minimum rate of change in AFP level, TTP, and PFS as mentioned above. In the GPC3 expression evaluation, a GPC3-IHC membrane H score and cytoplasm H score, a GPC3-IQD cell score and IQD intensity score were each used. The relationship between each of these scores and the minimum rate of change in sGPC3-N level, the maximum rate of change in sGPC3-C level, or the minimum rate of change in AFP level was studied using the t test as to the parameter estimator of regression analysis, or Spearman's correlation coefficient. As a result, as shown in Table 5, the GPC3-IQD cell score exhibited a significant relation to the maximum rate of change in sGPC3-C level. Hazard ratio of TTP or PFS was studied per change in each GPC3 score, i.e., change by 10 in GPC3-IHC membrane H score or cytoplasm H score, or GPC3-IQD intensity score or change by 100,000 in GPC3-IQD cell score. As a result, as shown in Table 5, no high correlation with PFS was seen in the conventional approaches (e.g., GPC3-IHC or fluorescence intensity per unit area (IQD intensity score)), whereas, surprisingly, unexpected high correlation with PFS was found only in the abundance of GPC3 per tumor cell (IQD cell score).

Table 5

TABLE 5

Relationship between AFP, TTP, or PFS and GPC3-IHC or GPC3-IQD score, and relationship between free GPC3 and GPC3-IHC or GPC3-IQD score

| | | GPC3-IHC | | GPC3-IQD | |
|---|---|---|---|---|---|
| | | Membrane H score | Cytoplasm H score | Intensity score | Cell score |
| Minimum rate of change in sGPC3-N | P value (Logistic) | 0.084 | 0.058 | 0.250 | 0.615 |
| | Parameter estimator | −0.170 | −0.233 | −0.656 | −0.000 |
| | Spearman's correlation coefficient | −0.41129 | −0.38306 | −0.11928 | 0.15615 |
| | The number of cases | 21 | 21 | 22 | 22 |
| Maximum rate of change in sGPC3-C | P value (Logistic) | 0.505 | 0.344 | 0.191 | 0.032 |
| | Parameter estimator | 1.579 | 2.781 | 16.666 | 0.011 |
| | Spearman's correlation coefficient | 0.285 | 0.285 | 0.351 | 0.205 |
| | The number of cases | 21 | 21 | 22 | 22 |
| Minimum rate of change in AFP | P value (Logistic) | 0.262 | 0.297 | 0.391 | 0.571 |
| | Parameter estimator | −0.098 | −0.117 | −0.414 | −0.000 |
| | Spearman's correlation coefficient | −0.087 | −0.148 | 0.032 | 0.076 |
| | The number of cases | 31 | 31 | 33 | 33 |
| TTP | P value (Wald) | 0.559 | 0.592 | 0.497 | 0.239 |
| | Hazard ratio | 0.986[§] | 1.014[§] | 0.920[§] | 0.494[ᴵ] |
| | The number of cases | 31 | 31 | 33 | 33 |
| PFS | P value (Wald) | 0.476 | 0.587 | 0.338 | 0.063 |
| | Hazard ratio | 0.983[§] | 1.015[§] | 0.885[§] | 0.328[ᴵ] |
| | The number of cases | 31 | 31 | 33 | 33 |

[§]HR per 10 score,
[ᴵ]HR per 100000 score

Figure 6:
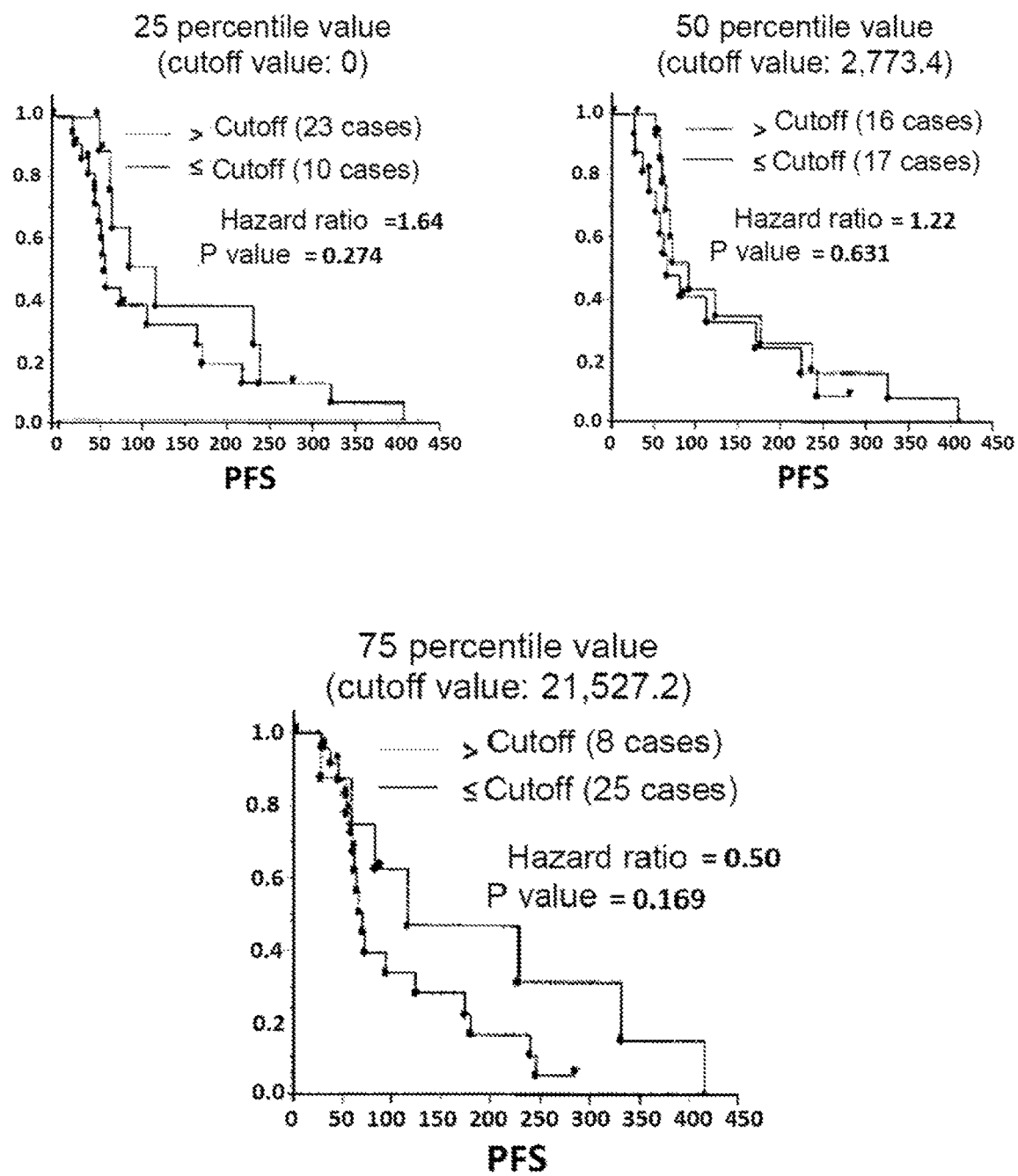
FIG. 6 shows a Kaplan-Meier curve of PFS in each of a low-value group and a high-value group at varying cutoff values for the IQD cell score of GPC3.

Subsequently, PFS in each of a low-value group and a high-value group at varying cutoff values for the IQD cell score of GPC3 was evaluated by the Kaplan-Meier method. As a result, as shown in FIG. 6, the high-value group was found to have longer PFS than that of the low-value group with increase in the cutoff value of the GPC3-IQD cell score. The hazard ratio of the cutoff value (66,183) at which the P value of the log-rank test was lowest was 0.24 with p=0.038 (cell score, 4 cases). Similar results were shown in a numerical value uncorrected with the fluorescence intensity of a non-cancer portion, or the largest value among samples. The hazard ratio of the cutoff value (60,790.3) at which the p value was lowest for the GPC3-IQD cell score uncorrected with the fluorescence intensity of a non-cancer portion was 0.21 with p=0.019 (cell score high-value group, 5 cases). The hazard ratio of the cutoff value (89,052.5) at which the p value was lowest for the largest value was 0.28 with p=0.032 (cell score high-value group, 6 cases). These results demonstrated that the sole therapy of GC33 and/or the combination therapy of GC33 and sorafenib are effective for patients having a large GPC3 expression level per tumor cell in HCC cells.

Example 6

Subsequently, various GPC3 evaluation methods that did not show high correlation with PFS in this evaluation, i.e., the evaluation methods using a GPC3-IHC membrane H score or cytoplasm H score or a GPC3-IQD intensity score, were restricted to only cases that exhibited a higher value of each score than the median value of the score. The median value was calculated on the basis of the average tumor cell size per unit area (µm²) in tumor tissues, and two groups were established: a group having a tumor cell size smaller than the median value and a group having a tumor cell size larger than the median value. For each score, the average GPC3 level rarely varied between the 2 groups based on the tumor cell sizes, with no significant difference (Table 6).

TABLE 6

Table 6: Relationship between cell size and each GPC3 score

| Cell size | The number of cases | Mean | SD (standard deviation) | P value |
|---|---|---|---|---|
| GPC3-IHC membrane H score (≥10) | | | | |
| Large | 8 | 132.90 | 104.60 | 0.720 |
| Small | 9 | 115.60 | 90.95 | |
| GPC3 IHC cytoplasm H score (≥85) | | | | |
| Large | 7 | 154.30 | 49.60 | 0.662 |
| Small | 6 | 143.50 | 33.90 | |
| GPC3 IQD intensity score (≥10) | | | | |
| Large | 8 | 23.60 | 15.01 | 0.256 |
| Small | 7 | 33.99 | 18.85 | |

Figure 7A:
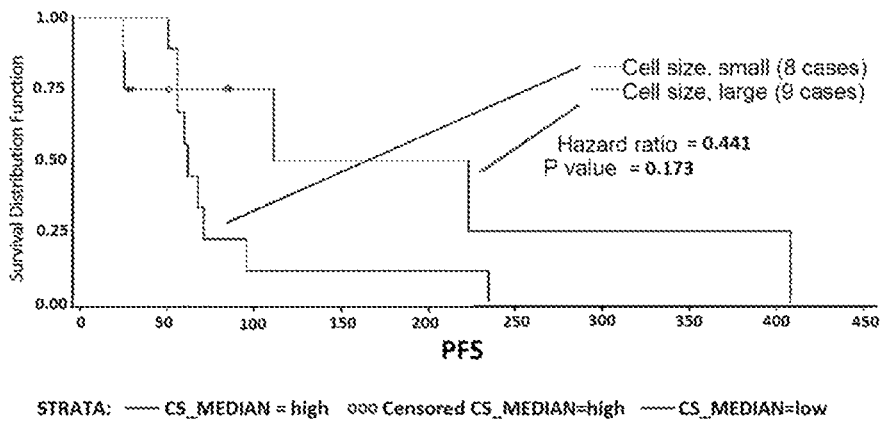
FIGS. 7A-C show a Kaplan-Meier curve in each group, wherein a group having a GPC3 score equal to or higher than a median value was classified into a group in which the tumor cell size of each individual was larger than the median value of tumor cell sizes in the group, and a group in which the tumor cell size of each individual was smaller than the median value of tumor cell sizes in the group.
Figure 7B:
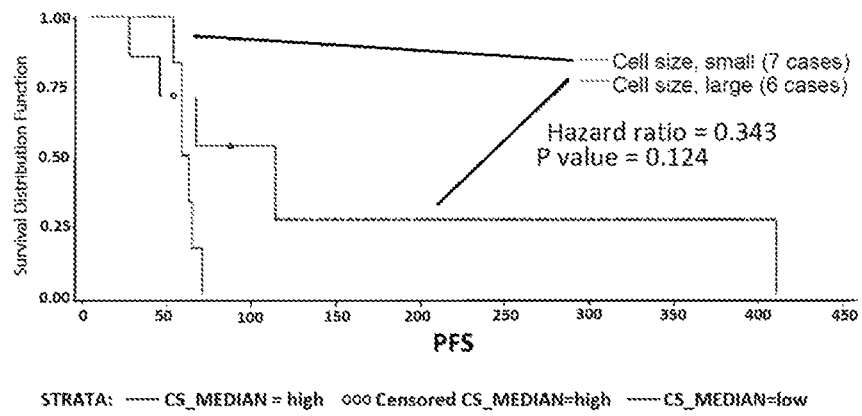
Figure 7C:
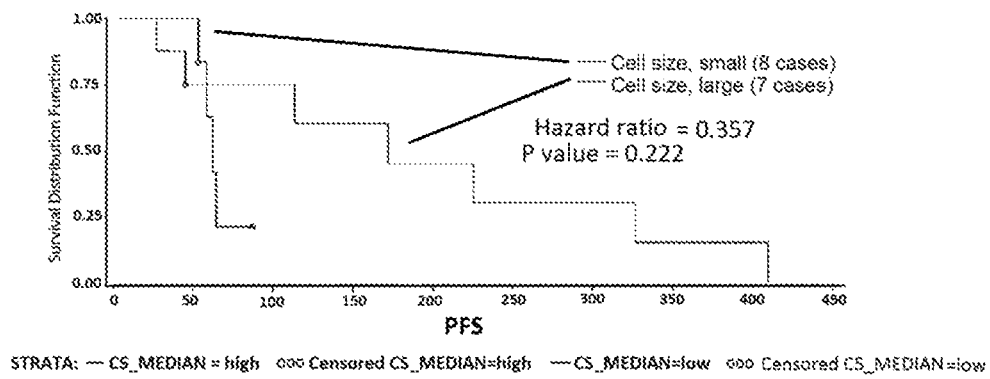

Meanwhile, PFS was compared between the group having a larger tumor cell size and the group having a smaller tumor cell size by the Kaplan-Meier method. As a result, for all of the scores, a tendency to prolong PFS was seen in the group having a larger tumor cell size with hazard ratios of 0.343 to 0.441 (Table 7 and FIG. 7). These results demonstrated that cell size evaluation is effective for predicting that the sole therapy of GC33 and/or the combination therapy of GC33 and sorafenib are effective for a group having a GPC3 expression level equal to or higher than a median value.
Table 7
Table 7: Relationship between cell size and PFS in group having each GPC3 score equal to or higher than median value All publications, patents, and patent applications cited herein are incorporated herein by reference in their entirety.

INDUSTRIAL APPLICABILITY

The present invention contributes to improvement in the efficacy of a GPC3-targeting therapeutic agent and improvement in the QOL of a patient to be treated and is useful in the treatment of cancer including liver cancer.

The invention claimed is:

1. A method for determining the efficacy of an anti-GPC3 antibody for liver cancer in a patient, the method comprising measuring an expression level of GPC3 indicated by immunofluorescent quantification digital slide (IQD) cell score in a biological sample isolated from the patient, wherein the anti-GPC3 antibody is determined to be effective when the expression level of GPC3 indicated by IQD cell score in the biological sample is higher than 22000.

2. The method according to claim 1, wherein the biological sample is a liver cancer tissue sample.

3. The method according to claim 1, wherein the anti-GPC3 antibody is administered to achieve a blood trough level of 200 μg/ml or higher in the patient.

4. The method according to claim 1, wherein the anti-GPC3 antibody is an antibody having antibody-dependent cellular cytotoxicity (ADCC) activity and/or complement-dependent cytotoxicity (CDC) activity.

5. The method according to claim 4, wherein the anti-GPC3 antibody is an antibody conjugated with a cytotoxic substance.

6. The method according to claim 1, wherein the anti-GPC3 antibody is administered concurrently with or separately from one or two or more anticancer agent(s).

7. The method according to claim 6, wherein the anticancer agent is sorafenib.

8. A method for selecting a patient for which an anti-GPC3 antibody is effective from a patient group with liver cancer, the method comprising the step of determining that the anti-GPC3 antibody is effective for a patient when the expression level of GPC3 indicated by IQD cell score in a biological sample isolated from the patient is higher than 22000 in IQD cell score.

9. A method for treating liver cancer, comprising administering an anti-GPC3 antibody to a patient having an expression level of GPC3 per tumor cell indicated by IQD cell score in a biological sample isolated from the patient is higher than 22000 in IQD cell score.

10. The method according to claim 2, wherein the anti-GPC3 antibody is an antibody comprising a heavy chain variable region comprising SEQ ID NO: 50 and a light chain variable region comprising SEQ ID NO: 66.

11. The method according to claim 8, wherein the anti-GPC3 antibody is an antibody comprising a heavy chain variable region comprising SEQ ID NO: 50 and a light chain variable region comprising SEQ ID NO: 66.

12. The method according to claim 9, wherein the biological sample is a liver cancer tissue sample.

13. The method according to claim 9, wherein the anti-GPC3 antibody is administered to achieve a blood trough level of 200 μg/ml or higher in the patient.

14. The method according to claim 9, wherein the anti-GPC3 antibody is an antibody having antibody-dependent cellular cytotoxicity (ADCC) activity and/or complement-dependent cytotoxicity (CDC) activity.

15. The method according to claim 9, wherein the anti-GPC3 antibody is an antibody conjugated with a cytotoxic substance.

16. The method according to claim 9, wherein the anti-GPC3 antibody is an antibody comprising a heavy chain variable region comprising SEQ ID NO: 50 and a light chain variable region comprising SEQ ID NO: 66.

* * * * *